(12) United States Patent
De Baetselier et al.

(10) Patent No.: US 9,617,339 B2
(45) Date of Patent: Apr. 11, 2017

(54) METHOD OF IMAGING A CARDIOVASCULAR DISEASE WITH AN ANTI-MACROPHAGE MANNOSE RECEPTOR IMMUNOGLOBULIN SINGLE VARIABLE DOMAIN

(71) Applicants: VIB VZW, Ghent (BE); Vrije Universiteit Brussel, Brussels (BE)

(72) Inventors: Patrick De Baetselier, Berchem (BE); Geert Raes, Sint-Genesius-Rode (BE); Steve Schoonooghe, Kessel-Lo (BE); Jens De Vos, Grimbergen (BE); Tony Lahoutte, Ganshoren (BE); Nick Devoogdt, Zemst (BE); Sophie Hernot, Machelen (BE); Gezim Bala, Brussels (BE); Simon Tierens, Londerzeel (BE)

(73) Assignees: VIB VZW, Ghent (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 14/775,510

(22) PCT Filed: Mar. 17, 2014

(86) PCT No.: PCT/EP2014/055336
§ 371 (c)(1),
(2) Date: Sep. 11, 2015

(87) PCT Pub. No.: WO2014/140376
PCT Pub. Date: Sep. 18, 2014

(65) Prior Publication Data
US 2016/0024213 A1    Jan. 28, 2016

Related U.S. Application Data

(60) Provisional application No. 61/798,071, filed on Mar. 15, 2013.

(51) Int. Cl.
| | | |
|---|---|---|
| A61B 5/00 | (2006.01) |
| A61K 39/395 | (2006.01) |
| A61K 51/10 | (2006.01) |
| A61P 9/10 | (2006.01) |
| C07K 16/28 | (2006.01) |
| A61K 49/04 | (2006.01) |
| C07K 14/705 | (2006.01) |

(52) U.S. Cl.
CPC ........ *C07K 16/2851* (2013.01); *A61B 5/0033* (2013.01); *A61B 5/0044* (2013.01); *A61B 5/0073* (2013.01); *A61K 39/3955* (2013.01); *A61K 49/04* (2013.01); *A61K 51/1027* (2013.01); *A61K 51/1096* (2013.01); *C07K 14/70596* (2013.01); *C07K 16/2896* (2013.01); *C07K 2317/22* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2009/0263387 A1    10/2009    Bebbington et al.
2011/0262348 A1    10/2011    Movahedi et al.

FOREIGN PATENT DOCUMENTS

| EP | 1134231 A1 | 9/2001 |
|---|---|---|
| WO | 9404678 A1 | 3/1994 |
| WO | 9425591 A1 | 11/1994 |
| WO | 9504079 A1 | 2/1995 |
| WO | 9634103 A1 | 10/1996 |
| WO | 9749805 A2 | 12/1997 |
| WO | 9937681 A2 | 7/1999 |
| WO | 0040968 A1 | 7/2000 |
| WO | 0043507 A1 | 7/2000 |
| WO | 0065057 A1 | 11/2000 |
| WO | 0121817 A1 | 3/2001 |
| WO | 0140310 A2 | 6/2001 |
| WO | 0144301 A1 | 6/2001 |
| WO | 0190190 A2 | 11/2001 |
| WO | 0248193 A2 | 6/2002 |
| WO | 02085945 A2 | 10/2002 |
| WO | 03025020 A1 | 3/2003 |
| WO | 03035694 A2 | 5/2003 |

(Continued)

OTHER PUBLICATIONS

Bala et al, 2015, European Heart Journal Cardiovascular Imaging. 16(2):ii238-ii239; 2 pages as printed).*
Movahedi et al., Nanobody-based targeting of the macrophage mannose receptor for effective in vivo imaging of tumor-associated macrophages, Cancer Research, Aug. 15, 2012, pp. 4165-4177, vol. 72, No. 16.
Broisat et al., Nanobodies targeting mouse/human VCAM1 for the nuclear imaging of atherosclerotic lesions, Circulation Research, Mar. 30, 2012, pp. 927-937, vol. 110, No. 7.

(Continued)

*Primary Examiner* — Zachary Howard
(74) *Attorney, Agent, or Firm* — TraskBritt P.C.

(57) ABSTRACT

The disclosure relates to the field of cardiovascular diseases. In particular, immunoglobulin single variable domains directed against macrophage mannose receptor (MMR) are provided that can be used in the diagnosis, prognosis and/or monitoring of cardiovascular diseases or as therapeutics. Also, the anti-macrophage mannose receptor (MMR) immunoglobulin single variable domains of the disclosure are useful at different stages of cardiovascular diseases, including post-infarction cardiovascular events. Further, the anti-macrophage mannose receptor (MMR) immunoglobulin single variable domains of the disclosure are particularly useful for the in vivo targeting and/or imaging of vulnerable atherosclerotic plaques.

12 Claims, 13 Drawing Sheets
(11 of 13 Drawing Sheet(s) Filed in Color)

(56) References Cited

FOREIGN PATENT DOCUMENTS

| WO | 03054016 | A2 | 7/2003 |
| WO | 03055527 | A2 | 7/2003 |
| WO | 2004041862 | A2 | 5/2004 |
| WO | 2004041863 | A2 | 5/2004 |
| WO | 2004041865 | A2 | 5/2004 |
| WO | 2004041867 | A2 | 5/2004 |
| WO | 2004049794 | A2 | 6/2004 |
| WO | 2004060965 | A2 | 7/2004 |
| WO | 2004062551 | A2 | 7/2004 |
| WO | 2005044858 | A1 | 5/2005 |
| WO | 2006040153 | A2 | 4/2006 |
| WO | 2006079372 | A1 | 8/2006 |
| WO | 2006092209 | A1 | 9/2006 |
| WO | 2006122786 | A2 | 11/2006 |
| WO | 2006122787 | A1 | 11/2006 |
| WO | 2006122825 | A2 | 11/2006 |
| WO | 2008020079 | A1 | 2/2008 |
| WO | 2008101985 | A2 | 8/2008 |
| WO | 2008142164 | A2 | 11/2008 |
| WO | 2009126659 | A1 | 10/2009 |
| WO | 2014140376 | A1 | 9/2014 |

OTHER PUBLICATIONS

Li et al., Differential Macrophage Polarization in Male and Female BALB/c Mice Infected with Coxsackievirus B3 Defines Susceptibility to Viral Myocarditis, Circulation Research, Aug. 2009, pp. 353-364, vol. 105, No. 4.

Williams et al., Macrophage Differentiation and Function in Atherosclerosis: Opportunities for Therapeutic Intervention? Journal of innate Immunity, 2012, pp. 498-508, vol. 4, No. 5-6.

Boytard et al., Role of Proinflammatory CD68(+) Mannose Receptor (−) Macrophages in Peroxidredoxin-1 Expression and in Abdominal Aortic Aneurysms in Humans, Arteriosclerosis Thrombosis and Vascular Biology, Feb. 2013, pp. 431, vol. 33, No. 2.

PCT International Search Report, PCT/EP2014055336, dated Jul. 21, 2014.

PCT International Written Opinion, PCT/EP2014055336, dated Jul. 21, 2014.

* cited by examiner $^{18}$F-anti-MMR3.49 vs $^{18}$F-cAbBCII10

PET  PET/CT  PET  PET/CT

METHOD OF IMAGING A CARDIOVASCULAR DISEASE WITH AN ANTI-MACROPHAGE MANNOSE RECEPTOR IMMUNOGLOBULIN SINGLE VARIABLE DOMAIN

CROSS-REFERENCE TO RELATED APPLICATIONS

This application is a national phase entry under 35 U.S.C. §371 of International Patent Application PCT/EP2014/055336, filed Mar. 17, 2014, designating the United States of America and published in English as International Patent Publication WO 2014/140376 A1 on Sep. 18, 2014, which claims the benefit under Article 8 of the Patent Cooperation Treaty and under 35 U.S.C. §119(e) to U.S. Provisional Patent Application Ser. No. 61/798,071, filed Mar. 15, 2013.

STATEMENT ACCORDING TO 37 C.F.R. §1.821(c) or (e)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference.

TECHNICAL FIELD

The disclosure relates to the field of medicine and cardiovascular diseases. In particular, immunoglobulin single variable domains directed against macrophage mannose receptor (MMR) are provided that can be used in the diagnosis, prognosis and/or monitoring of cardiovascular diseases or as therapeutics. Also, the anti-macrophage mannose receptor (MMR) immunoglobulin single variable domains of the disclosure are useful at different stages of cardiovascular diseases, including post-infarction cardiovascular events. Further, the anti-macrophage mannose receptor (MMR) immunoglobulin single variable domains of the disclosure are particularly useful for the in vivo targeting and/or imaging of vulnerable atherosclerotic plaques.

BACKGROUND

Cardiovascular disease is the leading cause of mortality and coronary heart disease alone is responsible for more than half of these deaths. The occurrence of a coronary event is due, in the vast majority of cases, to the rupture of a vulnerable or unstable coronary plaque, resulting in a sudden block of blood flow in critical arteries in the brain, the lungs or the heart. Several of these patients die suddenly of a first myocardial infarction or cardiac arrest without any symptoms or diagnosis of coronary artery disease (Naghavi et al., 2003, Circulation 108:1664-1672). Today, no general diagnostic method is available for detection or characterization of vulnerable plaques. Coronography, the reference method for the diagnosis of coronary artery disease, allows visualization of abnormal reductions of the internal diameter of an artery, called "stenoses," but does not allow the identification of non-stenotic plaques. Nuclear imaging holds potential for molecular imaging of vulnerable atherosclerotic plaques. Many tracers of various chemical nature, including lipoproteins, peptides, oligopeptides, antibodies, sugars, antisense nucleotides and nanoparticles were evaluated experimentally for molecular imaging of atherosclerosis (Riou et al., 2009, Curr. Med. Chem. 16:1499-1511). The main evaluated targets were oxidized LDLs and their receptors, the inflammatory process via macrophage cell imaging, or imaging of receptors or enzymes expressed by this cell type, apoptotic phenomena and the phenomenon of neoangiogenesis. Among tracers targeting the inflammatory process, 99m Tc-MCP-1 for nuclear imaging via SPECT (Single Photon Emission Computed Tomography) and [18F]-FDG for PET (Positron Emission Tomography) imaging have been used for in vivo noninvasive imaging of macrophage accumulation in experimental atherosclerotic lesions. On a clinical level, [18F]-FDG and 99mTc-Annexin A5 allowed noninvasive imaging of the accumulation of macrophages and apoptotic cells, respectively, in carotid atherosclerotic plaques of symptomatic patients. However, none of these radiotracers is currently used in routine clinical practice, mainly because of their inability to reach sufficient ratios of lesion versus background noise level in the coronary lesions. Indeed, nuclear imaging of vulnerable plaques in the coronary arteries is particularly difficult because of the low volume of the lesions and their proximity to blood that contains circulating unbound tracer.

An ideal tracer should combine high affinity and specificity, good solubility and stability and efficient radiolabeling with small size and fast blood clearance, so that high contrast images can be obtained shortly after administration. Nanobodies constitute a promising new class of radiotracers that might adhere to these conditions. They are derived from unique heavy-chain-only antibodies that are by nature present in camelids and represent the smallest possible (10-15 kDa) functional immunoglobulin-like antigen-binding fragment. Nanobody-based tracers targeting cancer antigens epidermal growth factor receptor, carcinoembryonic antigen, or human epidermal growth factor receptor 2 (HER2) with (sub)nanomolar affinities have already proven their ability to generate highly specific contrast images for noninvasive bio-imaging of cancer cells in mouse tumor models (Huang et al., 2008, Mol. Imaging Biol. 10:167-175; Vaneycken et al., 2010, J. Nucl. Med. 51:1099-1106; Vaneycken et al., 2011, FASEB J. 25:2433-2446). Recently, in hypercholesterolemic ApoE-deficient mice, representing a mouse model of atherosclerosis, it was documented that high contrast images and high lesion-to-heart and lesion-to-blood ratios could be obtained via SPECT imaging using Nanobodies targeting vascular cell adhesion molecule-1 (VCAM-1). (Broisat et al., 2012, Circ. Res. 110:927).

BRIEF SUMMARY

An ideal radiotracer for molecular imaging is characterized by a high affinity and specificity for its target, efficient radiolabeling, and a small size as well as a rapid blood clearance, so that images with high contrast can be rapidly obtained after administration of the tracer. The latter is particularly crucial in the case of the plaque because of its small size and its intravascular location. The disclosure is based on the inventors' surprising findings that a set of immunoglobulin single variable domains, in particular Nanobodies, recognizing the macrophage mannose receptor (MMR or CD206) exhibited all the characteristics of an ideal molecular imaging tracer defined above and that they can be used for targeting and in vivo imaging of vulnerable atherosclerotic plaques. In particular, anti-MMR immunoglobulin single variable domains can be used as tools for detecting vulnerable atherosclerotic plaques, for determining the degree of vulnerability of atherosclerotic plaques and/or for monitoring the evolution in function of time of the degree of vulnerability of atherosclerotic plaques. The inventors have also found that the anti-MMR immunoglobulin single variable domains can be used as molecular imaging tracer at different stages of cardiovascular events, including post-infarction events.

The disclosure thus envisages applications making use of specific immunoglobulin single variable domains, including Nanobodies, against MMR, as tracers for molecular imaging in the context of diagnosis or prognosis of cardiovascular diseases or disease manifestations associated therewith, including myocardial infarction and ischemic stroke, as well as post-infarction events such as cardiac remodeling and cardiac failure. The anti-MMR immunoglobulin single variable domains can thus be important clinical tools for predicting disease outcome and to guide treatment decisions.

The specific anti-MMR immunoglobulin single variable domains, including Nanobodies, may also have perspectives to be used as a vector for targeted delivery of therapeutics.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
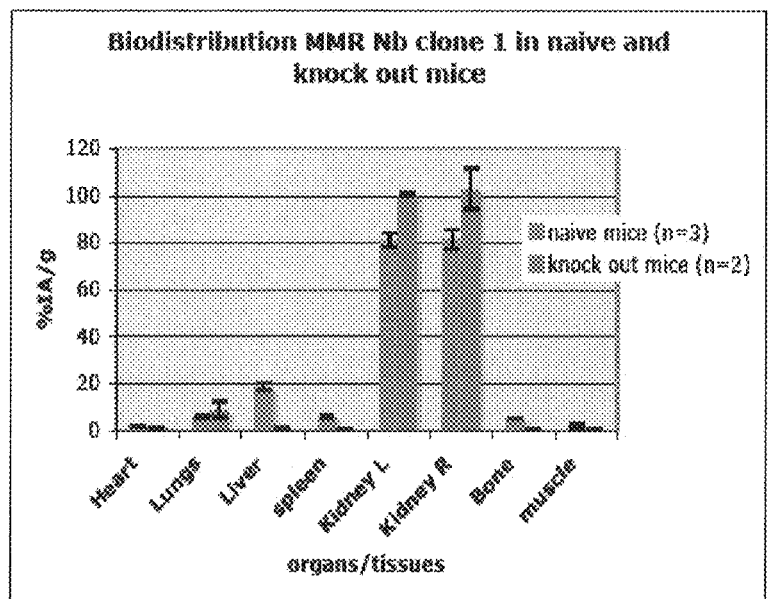
FIG. 1: Biodistribution of Nb MMR Cl1 in wild-type and MMR knockout C57bl/6 mice. Tracer uptake is expressed as injected activity per gram (% IA/g).

The disclosure will be described with respect to particular embodiments and with reference to certain drawings but the disclosure is not limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an," "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, structural biology, biophysics, pharmacology, genetics and protein and nucleic acid chemistry described herein are those well-known and commonly used in the art. The methods and techniques of the disclosure are generally performed according to conventional methods well known in the art and as described in various general and more specific references that are cited and discussed throughout the present specification unless otherwise indicated. See, for example, Sambrook et al., Molecular Cloning: A Laboratory Manual, $3^{rd}$ ed., Cold Spring Harbor Laboratory Press, Cold Spring Harbor, N.Y. (2001); Ausubel et al., Current Protocols in Molecular Biology, Greene Publishing Associates (1992, and Supplements to 2002); Rup, Biomolecular crystallography: principles, Practice and Applications to Structural Biology, $1^{st}$ edition, Garland Science, Taylor & Francis Group, LLC, an informa Business, N.Y. (2009); Limbird, Cell Surface Receptors, 3d ed., Springer (2004).

As used herein, the terms "polypeptide," "protein," "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "nucleic acid molecule," "polynucleotide," "polynucleic acid," "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "sequence identity," as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art. Examples of useful algorithms are PILEUP (Higgins & Sharp, CABIOS 5:151 (1989), BLAST and BLAST 2.0 (Altschul et al., J. Mol. Biol. 215: 403 (1990). Software for performing BLAST analyses is publicly available through the National Center for Biotechnology Information (located on the World Wide Web at ncbi.nlm.nih.gov/).

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about 2, about 5, about 10, up to about 20, up to about 30 or up to about 50 or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

As used herein, the terms "determining," "measuring," "assessing," and "assaying" are used interchangeably and include both quantitative and qualitative determinations.

DETAILED DESCRIPTION

One aspect hereof relates to an immunoglobulin single variable domain directed against and/or specifically binding to a macrophage mannose receptor, for use in the diagnosis, prognosis, prevention and/or treatment of a cardiovascular disease, including atherosclerosis as well as post-infarction events such as cardiac remodeling and cardiac failure. More particularly, it is envisaged within this context to use an anti-macrophage mannose receptor (anti-MMR) immunoglobulin single variable domain as contrast agent in methods of medical imaging in order to visualize atherosclerotic plaques in a subject, preferably aortic atherosclerotic plaques, including coronary and carotid atherosclerotic plaques, and if appropriate, to use these anti-MMR immunoglobulin single variable domain for targeted delivery of therapeutics. Further, it is also envisaged within this context to use an anti-macrophage mannose receptor (anti-MMR) immunoglobulin single variable domain as contrast agent in methods of medical imaging in order to predict the development of a cardiovascular event after the occurrence of a myocardial infarction (thus at post-infarction stage), such as cardiac remodeling and cardiac failure.

As used herein, the term "medical imaging" refers to the technique and process that is used to visualize the inside of an organism's body (or parts and/or functions thereof), for clinical purposes (e.g., disease diagnosis, prognosis or therapy monitoring) or medical science (e.g., study of anatomy and physiology). Examples of medical imaging methods include invasive techniques, such as intravascular ultrasound (IVUS), as well as non-invasive techniques, such as magnetic resonance imaging (MRI), ultrasound (US) and nuclear imaging. Examples of nuclear imaging include positron emission tomography (PET) and single photon emission computed tomography (SPECT).

The application, thus, provides for a novel class of radiotracers specifically targeting a macrophage mannose receptor in view of medical applications in the field of cardiovascular diseases. In the following part, detailed description on the anti-macrophage mannose receptor (anti-MMR) immunoglobulin single variable domain as radiotracers will first be provided.

Anti-Macrophage Mannose Receptor (Anti-MMR) Immunoglobulin Single Variable Domains Within the context hereof, it is envisaged to specifically target a macrophage mannose receptor expressed on a cell surface by making use of immunoglobulin single variable domains. The nature of the macrophage mannose receptor is not critical to the disclosure. According to a specific embodiment, the targeted macrophage mannose receptor is of mammalian origin. Preferably, the targeted macrophage mannose receptor is a human macrophage mannose receptor (SEQ ID NO:141). Alternatively, the targeted macrophage mannose receptor is a mouse macrophage mannose receptor (SEQ ID NO:143). The targeted macrophage mannose receptor may also be a rat macrophage mannose receptor (SEQ ID NO:147), or a rabbit macrophage mannose receptor (SEQ ID NO:148). The present application is in its broadest sense not particularly limited to or defined by a specific antigenic determinant, epitope, part, domain, subunit or conformation of the macrophage mannose receptor, and in particular the human macrophage mannose receptor (SEQ ID NO:141), or mouse macrophage mannose receptor (SEQ ID NO:143), or rat macrophage mannose receptor (SEQ ID NO:147), or rabbit macrophage mannose receptor (SEQ ID NO:148) against which the immunoglobulin single variable domains are directed or to which the immunoglobulin single variable domains will specifically bind.

As used herein, the term "macrophage mannose receptor" (MMR) refers to a type I transmembrane protein, first identified in mammalian tissue macrophages and later in dendritic cells and a variety of endothelial and epithelial cells, and is well-known in the art. Macrophages are central actors of the innate and adaptive immune responses. They are disseminated throughout most organs to protect against entry of infectious agents by internalizing and most of the time, killing them. Among the surface receptors present on macrophages, the mannose receptor recognizes a variety of molecular patterns generic to microorganisms. The MMR is composed of a single subunit with N- and O-linked glycosylations and consists of five domains: an N-terminal cysteine-rich region, which recognizes terminal sulfated sugar residues; a fibronectin type II domain with unclear function; a series of eight C-type, lectin-like carbohydrate recognition domains (CRDs) involved in $Ca^{2+}$-dependent recognition of mannose, fucose, or N-acetylglucosamine residues on the envelop of pathogens or on endogenous glycoproteins with CRDs 4-8 showing affinity for ligands comparable with that of intact MMR; a single transmembrane domain; and a 45 residue-long cytoplasmic tail that contains motifs critical for MMR-mediated endocytosis and sorting in endosomes (Chieppa et al., 2003, J. Immunol. 171:4552-60). The macrophage mannose receptor as referred to in the present application includes cross-species variants of the MMR protein (e.g., from mouse, rat, rabbit, human, etc.) which are referred to herein as "homologs" of the macrophage mannose receptor. Thus, the macrophage mannose receptor as referred to in the present application includes homologues of a full length MMR protein. Non-limiting examples of homologs of MMRs include the human MMR (synonyms: Mrc1 or CD206; accession number nucleotide sequence: NM_002438.2; accession number protein sequence: NP_002429.1 and as in SEQ ID NO:141), the mouse MMR (synonyms: MRC1 or CD206; accession number nucleotide sequence: NM_008625.2; accession number protein sequence: NP_032651.2 and as in SEQ ID NO:143), the rat MMR (synonym: MRC1; accession number nucleotide sequence: NM_001106123.1; accession number protein sequence: NP_001099593.1 and as in SEQ ID NO:147), the rabbit MMR (synonyms: MRC1; accession number nucleotide sequence: NC_013684.1; accession number protein sequence: XP_002717402.1 and as in SEQ ID NO:148). As an illustrative example, the deduced amino acid sequence of mouse mannose receptor has an overall 82% homology with the human mannose receptor, as can be easily measured in a BLASTp alignment (Altschul et al., 1990, Mol. Biol. 215:403-10). The macrophage mannose receptor as referred to in the disclosure also includes fragments of the full length MMR protein. A non-limiting example of a fragment of a full length MMR protein includes the ectodomain of a particular MMR. The "ectodomain," as used herein, refers to a fragment of a MMR containing the N-terminus that is cysteine-rich, followed by the fibronectin type II domain and eight carbohydrate recognition domains (CRDs). All of the eight CRDs are particularly well conserved, especially CRD4. For example, mouse CRD4 shows 92% homology with the equivalent region of the human protein. In particular, the ectodomain of the mouse macrophage mannose receptor is defined as the AA 19-AA 1388 fragment (SEQ ID NO:146) of the corresponding full length mouse MMR amino acid sequence as defined in NP_032651.2 (SEQ ID NO:143). Or, the ectodomain of the human macrophage mannose receptor is defined as the AA 19-AA 1383 fragment (SEQ ID NO:145) of the corresponding full length human MMR amino acid sequence as defined in NP_002429.1 (SEQ ID NO:141). For the sake of clarity, the ectodomain of a particular MMR does not comprise the single transmembrane domain nor the cytoplasmice tail of an MMR.

As used herein, the phrasing "anti-macrophage mannose receptor (anti-MMR) immunoglobulin single variable domain" refers to an immunoglobulin single variable domain (as defined further herein) that specifically recognizes a macrophage mannose receptor of choice. As used herein, the term "specifically recognizing" or "specifically binding to" or simply "specific for" refers to the ability of an immunoglobulin single variable domain to preferentially bind to one antigen (in this case the macrophage mannose receptor), versus a different antigen, and does not necessarily imply high affinity. In certain embodiments, a specific binding interaction will discriminate between desirable and undesirable antigens in a sample, in some embodiments more than about 10 to 100-fold or more (e.g., more than about 1000- or 10,000-fold). The terms "specifically bind," "selectively bind," "preferentially bind," and grammatical equivalents thereof, are used interchangeably herein. The term "affinity," as used herein, refers to the degree to which an immunoglobulin single variable domain binds to an antigen so as to shift the equilibrium of antigen and immunoglobulin single variable domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the antibody (fragment) and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M. An immunoglobulin single variable domain that can specifically bind to and/or that has affinity for a specific antigen or antigenic determinant (e.g., epitope) is said to be "against" or "directed against" the antigen or antigenic determinant. An immunoglobulin single variable domain, according to the disclosure, is said to be "cross-reactive" for two or more different antigens or antigenic determinants (such as macrophage mannose receptor from two different species of mammal, such as human MMR and mouse MMR) if it is specific for both these different antigens or antigenic determinants. It will thus be appreciated that, according to the disclosure, immunoglobulin single variable domains that are directed against a macrophage mannose receptor from one species may or may not show cross-reactivity with a macrophage mannose receptor from another species. For example, immunoglobulin single variable domains directed against MMR, in particular human MMR (SEQ ID NO:141) may or may not show cross-reactivity with a MMR from one or more other species of animals that are often used in animal models for diseases (for example, mouse, rat, rabbit, pig or dog). It will be clear to the skilled person that such cross-reactivity, when present, may have advantages for diagnostic and/or therapeutic development, since it allows the immunoglobulin single variable domains to be tested in such disease models. It is expected that the immunoglobulin single variable domains, according to the disclosure, will generally bind to all naturally occurring or synthetic analogs, variants, mutants, alleles of the MMRs mentioned herein.

According to a specific embodiment, the immunoglobulin single variable domain specifically binds to the ectodomain of a macrophage mannose receptor, and in particular the ectodomain of the mouse macrophage mannose receptor, the ectodomain of the rat macrophage mannose receptor, the ectodomain of the rabbit macrophage mannose receptor and/or the ectodomain of the human macrophage mannose receptor (see Table 11).

As used herein, the term "immunoglobulin single variable domain" defines molecules wherein the antigen binding site is present on, and formed by, a single immunoglobulin domain (which is different from conventional immunoglobulins or their fragments, wherein typically two immunoglobulin variable domains interact to form an antigen binding site). It should, however, be clear that the term "immunoglobulin single variable domain" does comprise fragments of conventional immunoglobulins wherein the antigen binding site is formed by a single variable domain. Generally, an immunoglobulin single variable domain will be an amino acid sequence comprising 4 framework regions (FR1 to FR4) and 3 complementary determining regions (CDR1 to CDR3), preferably according to the following formula (1): FR1-CDR1-FR2-CDR2-FR3-CDR3-FR4 (1), or any suitable fragment thereof (which will then usually contain at least some of the amino acid residues that form at least one of the complementarity determining regions). Immunoglobulin single variable domains comprising 4 FRs and 3 CDRs are known to the person skilled in the art and have been described, as a non-limiting example, in Wesolowski et al., 2009, Med. Microbiol. Immunol. 198:157-174.

Typical, but non-limiting, examples of immunoglobulin single variable domains include light chain variable domain sequences (e.g., a VL domain sequence) or a suitable fragment thereof, or heavy chain variable domain sequences (e.g., a VH domain sequence or VHH domain sequence) or a suitable fragment thereof, as long as it is capable of forming a single antigen binding unit. Thus, according to a preferred embodiment, the binding domain moiety is an immunoglobulin single variable domain that is a light chain variable domain sequence (e.g., a VL domain sequence) or a heavy chain variable domain sequence (e.g., a VH domain sequence); more specifically, the immunoglobulin single variable domain is a heavy chain variable domain sequence that is derived from a conventional four-chain antibody or a heavy chain variable domain sequence that is derived from a heavy chain antibody. The immunoglobulin single variable domain may be a domain antibody, or a single domain antibody, or a "dAB" or dAb, or a Nanobody, as defined herein, or another immunoglobulin single variable domain, or any suitable fragment of any one thereof. For a general description of single-domain antibodies, reference is made to the following book: "Single domain antibodies," Methods in Molecular Biology, Eds. Saerens and Muyldermans, 2012, Vol. 911. The immunoglobulin single variable domains, generally comprise a single amino acid chain that can be considered to comprise 4 "framework sequences" or FRs and 3 "complementary determining regions" or CDRs, as defined hereinbefore. It should be clear that framework regions of immunoglobulin single variable domains may also contribute to the binding of their antigens (Desmyter et al., 2002, J. Biol. Chem. 277:23645-50; Korotkov et al., 2009, Structure 17:255-65). The delineation of the CDR sequences (and thus also the FR sequences) can be based on the IMGT unique numbering system for V-domains and V-like domains (Lefranc et al., 2003, Develop. Comparat. Immunol. 27:55-77). Alternatively, the delineation of the FR and CDR sequences can be done by using the Kabat numbering system as applied to VHH domains from Camelids in the article of Riechmann and Muyldermans 2000, J. Immunol. Methods 240:185-195.

It should be noted that the immunoglobulin single variable domains in their broadest sense are not limited to a specific biological source or to a specific method of preparation. The term "immunoglobulin single variable domain" encompasses variable domains of different origin, comprising mouse, rat, rabbit, donkey, human, shark, camelid variable domains. According to specific embodiments, the immunoglobulin single variable domains are derived from shark antibodies (the so-called immunoglobulin new antigen receptors or IgNARs), more specifically from naturally occurring heavy chain shark antibodies, devoid of light chains, and are known as VNAR domain sequences. Preferably, the immunoglobulin single variable domains are derived from camelid antibodies. More preferably, the immunoglobulin single variable domains are derived from naturally occurring heavy chain camelid antibodies, devoid of light chains, and are known as VHH domain sequences or Nanobodies.

A preferred immunoglobulin single variable domain within the scope hereof is a Nanobody (as defined further herein, and including, but not limited to, a VHH). The term "Nanobody" (Nb), as used herein, is a single-domain antigen binding fragment. It particularly refers to a single variable domain derived from naturally occurring heavy chain antibodies and is known to the person skilled in the art. Nanobodies are usually derived from heavy chain only antibodies (devoid of light chains) seen in camelids (Hamers-Casterman et al., 1993, Nature 363: 446-448; Desmyter et al., 1996, Nat. Struct. Biol. 803-811) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). NANOBODY® and NANOBODIES® are registered trademarks of Ablynx NV (Belgium). For a further description of VHH's or Nanobodies, reference is made to the book "Single domain antibodies," Methods in Molecular Biology, Eds. Saerens and Muyldermans, 2012, Vol. 911, in particular to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As will be known by the person skilled in the art, the Nanobodies are particularly characterized by the presence of one or more Camelidae "hallmark residues" in one or more of the framework sequences (according to Kabat numbering), as described, for example, in WO 08/020079, on page 75, Table A-3, incorporated herein by reference. It should be noted that the Nanobodies, of the disclosure in their broadest sense are not limited to a specific biological source or to a specific method of preparation. For example, Nanobodies, can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab," as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. A further description of Nanobodies, including humanization and/or camelization of Nanobodies, can be found, e.g., in WO 08/101985 and WO 08/142164, as well as further herein.

Within the scope hereof, the term "immunoglobulin single variable domain" also encompasses variable domains that are "humanized" or "camelized," in particular Nanobodies that are "humanized" or "camelized." For example, both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" immunoglobulin single variable domains of the disclosure, respectively. This nucleic acid can then be expressed in a manner known per se, so as to provide the desired immunoglobulin single variable domains of the disclosure. Alternatively, based on the amino acid sequence of a naturally occurring $V_HH$ domain or VH domain, respectively, the amino acid sequence of the desired humanized or camelized immunoglobulin single variable domains of the disclosure, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized immunoglobulin single variable domains of the disclosure, respectively, can be designed and then synthesized de novo using techniques for nucleic acid synthesis known per se, after which the nucleic acid thus obtained can be expressed in a manner known per se, so as to provide the desired immunoglobulin single variable domains of the disclosure. Other suitable methods and techniques for obtaining the immunoglobulin single variable domains of the disclosure and/or nucleic acids encoding the same, starting from naturally occurring VH sequences or preferably $V_HH$ sequences, will be clear from the skilled person, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a Nanobody of the disclosure or a nucleotide sequence or nucleic acid encoding the same.

Non-limiting examples of Nanobodies within the scope hereof are as described herein and include anti-human, anti-mouse and cross-reactive anti-human/anti-mouse MMR Nanobodies. For example, in Table 1, in particular SEQ ID NOS:1-7; in Table 10, in particular SEQ ID NOS:8-37). In a specific embodiment, the Nanobodies of the disclosure may comprise at least one of the complementarity determining regions (CDRs), as described herein, for example, CDRs with an amino acid sequence selected from SEQ ID NOS: 38-69 (CDR1), SEQ ID NOS:70-101 (CDR2), SEQ ID NOS:102-133 (CDR3) (see Tables 1, 10). Preferably, the Nanobodies of the disclosure comprise a CDR1, a CDR2 and a CDR3 selected from the group consisting of SEQ ID NOS:38-133, according to the above described formula (1). More specifically, the Nanobodies can be selected from the group comprising SEQ ID NOS:1-37, or a functional fragment thereof. A "functional fragment" or a "suitable fragment," as used herein, may, for example, comprise one of the CDR loops. Preferably, the functional fragment comprises CDR3. More specifically, the Nanobodies consist of any of SEQ ID NOS:1-37.

Also within the scope hereof are natural or synthetic analogs, mutants, variants, alleles, parts or fragments (herein collectively referred to as "variants") of the immunoglobulin single variable domains, in particular the Nanobodies, as defined herein, and in particular variants of the immunoglobulin single variable domains of SEQ ID NOS:1-37 (see, Tables 1, 10). Thus, according to one embodiment of the disclosure, the term "immunoglobulin single variable domain of the disclosure" or "Nanobody of the disclosure" in its broadest sense also covers such variants. Generally, in such variants, one or more amino acid residues may have been replaced, deleted and/or added, compared to the immunoglobulin single variable domains of the disclosure, as defined herein. Such substitutions, insertions or deletions may be made in one or more of the FRs and/or in one or more of the CDRs, and in particular variants of the FRs and CDRs of the immunoglobulin single variable domains of SEQ ID NOS:1-37 (see Tables 1, 10). Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST (50, 51). Software for performing BLAST analyses is publicly available through the National Center for Biotechnology Information (located on the World Wide Web at ncbi.nlm.nih.gov/). It will be understood that for determining the degree of amino acid identity of the amino acid sequences of the CDRs of one or more sequences of the immunoglobulin single variable domains, the amino acid residues that form the framework regions are disregarded. Similarly, for determining the degree of amino acid identity of the amino acid sequences of the FRs of one or more sequences of the immunoglobulin single variable domains of the disclosure, the amino acid residues that form the complementarity regions are disregarded. Such variants of immunoglobulin single variable domains may be of particular advantage since they may have improved potency/affinity.

By means of non-limiting examples, a substitution may, for example, be a conservative substitution, as described herein, and/or an amino acid residue may be replaced by another amino acid residue that naturally occurs at the same position in another $V_HH$ domain. Thus, any one or more substitutions, deletions or insertions, or any combination thereof, that either improve the properties of the Nanobody of the disclosure or that at least do not detract too much from the desired properties or from the balance or combination of desired properties of the Nanobody of the disclosure (i.e., to the extent that the Nanobody is no longer suited for its intended use) are included within the scope of the disclosure. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the Nanobodies thus obtained.

According to particularly preferred embodiments, variants of the immunoglobulin single variable domains, in particular the Nanobodies hereof may have a substitution, deletion or insertion, of 1, 2 or 3 amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 10. More preferably, variants of the immunoglobulin single variable domains, in particular the Nanobodies, of the disclosure may have a conservative substitution, as defined herein, of 1, 2 or 3 amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 10.

Also encompassed within the scope hereof are immunoglobulin single variable domains that are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains of the disclosure are in a "multispecific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific, as defined herein, immunoglobulin single variable domain of the disclosure may be suitably directed against two or more different epitopes on the same antigen, for example, against two or more different epitopes of the MMR; or may be directed against two or more different antigens, for example, against an epitope of the MMR and an epitope of vascular cell adhesion molecule 1 (VCAM-1). In particular, a monovalent immunoglobulin single variable domain of the disclosure is such that it will bind to the target with an affinity less than 500 nM, preferably less than 200 nM, more preferably less than 10 nM, such as less than 500 pM. Multivalent or multispecific immunoglobulin single variable domains of the disclosure may also have (or be engineered and/or selected for) increased avidity and/or improved selectivity for the desired MMR, and/or for any other desired property or combination of desired properties that may be obtained by the use of such multivalent or multispecific immunoglobulin single variable domains.

Further, and depending on the host organism used to express the immunoglobulin single variable domain, deletions and/or substitutions within the immunoglobulin single variable domain may be designed in such a way that, e.g., one or more sites for post-translational modification (such as one or more glycosylation sites) are removed, as will be within the ability of the person skilled in the art. Alternatively, substitutions or insertions may be designed so as to introduce one or more sites for attachment of functional groups, as described further herein.

Screening and Selection of Suitable Immunoglobulin Single Variable Domains

A preferred class of immunoglobulin single variable domains is directed against and/or specifically binds to an MMR, as described hereinbefore. Immunoglobulin single variable domains can be identified in several ways, and will be illustrated hereafter in a non-limiting way for VHHs. VHH sequences can generally be generated or obtained by suitably immunizing a species of Camelid with a MMR, (i.e., so as to raise an immune response and/or heavy chain antibodies directed against a MMR), by obtaining a suitable biological sample from the Camelid (such as a blood sample, or any sample of B-cells), and by generating $V_HH$ sequences directed against a MMR, starting from the sample, using any suitable technique known per se. Such techniques will be clear to the skilled person. Alternatively, such naturally occurring $V_HH$ domains against MMR can be obtained from naive libraries of Camelid $V_HH$ sequences, for example, by screening such a library using MMR or at least one part, fragment, antigenic determinant or epitope thereof using one or more screening techniques known per se. Such libraries and techniques are, for example, described in WO 9937681, WO 0190190, WO 03025020 and WO 03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as, for example, described in WO 0043507. Yet another technique for obtaining $V_HH$ sequences directed against a MMR involves suitably immunizing a transgenic mammal that is capable of expressing heavy chain antibodies (i.e., so as to raise an immune response and/or heavy chain antibodies directed against a MMR), obtaining a suitable biological sample from the transgenic mammal (such as a blood sample, or any sample of B-cells), and then generating $V_HH$ sequences directed against a MMR starting from the sample, using any suitable technique known per se. For example, for this purpose, the heavy chain antibody-expressing mice and the further methods and techniques described in WO 02085945 and in WO 04049794 can be used.

Accordingly, the application encompasses methods of generating immunoglobulin single variable domains, according to the disclosure. As a non-limiting example, a method is provided of generating Nanobodies directed against or specifically binding to the macrophage mannose receptor, as described herein, comprising:

(i) immunizing an animal with a MMR, in particular a mouse (SEQ ID NO. 143) or human MMR (SEQ ID NO. 141), or a fragment thereof; and (ii) screening for Nanobodies specifically binding to the MMR.

For the immunization of an animal with a MMR, the MMR may be produced and purified using conventional methods that may employ expressing a recombinant form of the MMR in a host cell, and purifying the MMR using affinity chromatography and/or antibody-based methods. Any suitable animal, e.g., a warm-blooded animal, in particular a mammal such as a rabbit, mouse, rat, camel, sheep, cow, shark, pig, or a bird such as a chicken or turkey, may be immunized using any of the techniques well known in the art suitable for generating an immune response. The screening for Nanobodies, as a non-limiting example, specifically binding to a MMR may, for example, be performed by screening a set, collection or library of cells that express heavy chain antibodies on their surface (e.g., B-cells obtained from a suitably immunized Camelid), or bacteriophages that display a fusion of genIII and Nanobody at their surface, by screening of a (naïve or immune) library of $V_HH$ sequences or Nanobody sequences, or by screening of a (naïve or immune) library of nucleic acid sequences that encode VHH sequences or Nanobody sequences, which may all be performed in a manner known per se, and which method may optionally further comprise one or more other suitable steps, such as, for example and without limitation, a step of affinity maturation, a step of expressing the desired amino acid sequence, a step of screening for binding and/or for activity against the desired antigen (in this case, the MMR), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

Modifications of Anti-MMR Immunoglobulin Single Variable Domains

The immunoglobulin single variable domains within the scope hereof may be further modified and/or may comprise (or can be further fused to) other moieties, as described further herein. Examples of modifications, as well as examples of amino acid residues within the immunoglobulin single variable domain, preferably the Nanobody sequence, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the immunoglobulin single variable domain of the disclosure, and in particular of one or more functional groups, residues or moieties that confer one or more desired properties or functionalities to the immunoglobulin single variable domain of the disclosure. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFvs and single domain antibodies), for which reference is, for example, made to Remington's Pharmaceutical Sciences, 16th ed., Mack Publishing Co., Easton, Pa. (1980). Such functional groups may, for example, be linked directly (for example, covalently) to a immunoglobulin single variable domain of the disclosure, or optionally via a suitable linker or spacer, as will again be clear to the skilled person. One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including, but not limited to, (single) domain antibodies and ScFvs); reference is made to, for example, Chapman, Nat. Biotechnol., 54:531-545 (2002); by Veronese and Harris, Adv. Drug Deliv. Rev. 54:453-456 (2003), by Harris and Chess, Nat. Rev. Drug. Discov. 2 (2003) and in WO 04060965. Various reagents for pegylation of proteins are also commercially available, for example, from Nektar Therapeutics, USA. Preferably, site-directed pegylation is used, in particular via a cysteine-residue (see, for example, Yang et al., Protein Engineering, 16, 10, 761-770 (2003). For example, for this purpose, PEG may be attached to a cysteine residue that naturally occurs in an immunoglobulin single variable domain, or the immunoglobulin single variable domain may be modified so as to suitably introduce one or more cysteine residues for attachment of PEG, or an amino acid sequence comprising one or more cysteine residues for attachment of PEG may be fused to the N- and/or C-terminus of an immunoglobulin single variable domain, all using techniques of protein engineering known per se to the skilled person. Preferably, for the immunoglobulin single variable domains of the disclosure, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the immunoglobulin single variable domain or polypeptide of the disclosure. Another technique for increasing the half-life of an immunoglobulin single variable domain may comprise the engineering into bifunctional constructs (for example, one Nanobody against the target MMR and one against a serum protein such as albumin) or into fusions of immunoglobulin single variable domains with peptides (for example, a peptide against a serum protein such as albumin).

Yet another modification may comprise the introduction of one or more detectable labels or other signal-generating groups or moieties, depending on the intended use of the labeled immunoglobulin single variable domain. Suitable labels and techniques for attaching, using and detecting them will be clear to the skilled person, and for example include, but are not limited to, fluorescent labels, (such as IRDye800, VivoTag800, fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and, for example, include moieties that can be detected using NMR or ESR spectroscopy. Such labeled Nanobodies and polypeptides of the disclosure may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, 2,2', 2"-(10-(2-((2,5-dioxopyrrolidin-1-yl)oxy)-2-oxoethyl)-1,4, 7,10-tetraazacyclododecane-1,4,7-triyl)triacetic acid (DOTA), 2,2'-(7-(2-((2,5-dioxopyrrolidin-1-yl)oxy)-2-oxoethyl)-1,4,7-triazonane-1,4-diyl)diacetic acid (NOTA), diethyl-enetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link the immunoglobulin single variable domain to another protein, polypeptide or chemical compound that is bound to the other half of the binding pair, i.e., through formation of the binding pair. For example, a Nanobody of the disclosure may be conjugated to biotin, and linked to another protein, polypeptide, compound or carrier conjugated to avidin or streptavidin. For example, such a conjugated Nanobody may be used as a reporter, for example, in a diagnostic system where a detectable signal-producing agent is conjugated to avidin or streptavidin. Such binding pairs may, for example, also be used to bind the Nanobody of the disclosure to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the Nanobody of the disclosure.

According to a preferred embodiment, the anti-MMR immunoglobulin single variable domain, as used in the present application, is coupled or fused to a detectable label, either directly or through a linker. Preferably, the detectable label is a radio-isotope, in particular a radioactive tracer suitable for medical applications, such as in in vivo nuclear imaging. Examples include, without the purpose of being limitative, technetium 99m ($^{99m}$Tc), iodium 123 ($^{123}$I), zirconium 89 ($^{89}$Zr), iodium 125 ($^{125}$I), indium 111 ($^{111}$In), fluor 18 ($^{18}$F), copper 64 ($^{64}$Cu), gallium 67 ($^{67}$Ga), gallium 68 ($^{68}$Ga), and any other radio-isotope which can be used in animals, in particular mouse, rabbit or human. According to a specific embodiment, the detectable label is $^{99m}$Tc.

In another preferred embodiment, the immunoglobulin single variable domain, as used in the disclosure, is coupled to or fused to a moiety, in particular a therapeutically active agent, either directly or through a linker. As used herein, a "therapeutically active agent" means any molecule that has or may have a therapeutic effect (i.e., curative or stabilizing effect) in the context of treatment of a cardiovascular disease, in particular of atherosclerosis, preferably vulnerable plaques, or of a post-infarction event such as cardiac remodeling or heart failure.

Preferably, a therapeutically active agent is a disease-modifying agent, which can be a cytotoxic agent, such as a toxin, or a cytotoxic drug, or an enzyme capable of converting a prodrug into a cytotoxic drug, or a radionuclide, or a cytotoxic cell, or which can be a non-cytotoxic agent. Even more preferably, a therapeutically active agent has a curative effect on the disease.

Alternatively, a therapeutically active agent is a disease-stabilizing agent, in particular a molecule that has a stabilizing effect on the evolution of a cardiovascular disease, in particular atherosclerosis, and more specifically, a stabilizing effect on vulnerable atherosclerotic plaques. Examples of stabilizing agents include anti-inflammatory agents, in particular non-steroid anti-inflammatory molecules.

According to one specific embodiment, the therapeutically active agent is not a cytotoxic agent.

Linker Molecules

Preferred "linker molecules" or "linkers" are peptides of 1 to 200 amino acids length, and are typically, but not necessarily, chosen or designed to be unstructured and flexible. For instance, one can choose amino acids that form no particular secondary structure. Or, amino acids can be chosen so that they do not form a stable tertiary structure. Or, the amino acid linkers may form a random coil. Such linkers include, but are not limited to, synthetic peptides rich in Gly, Ser, Thr, Gln, Glu or further amino acids that are frequently associated with unstructured regions in natural proteins (Dosztányi, Z., Csizmok, V., Tompa, P., & Simon, I. (2005). IUPred: web server for the prediction of intrinsically unstructured regions of proteins based on estimated energy content. Bioinformatics (Oxford, England), 21(16), 3433-4.). Non-limiting examples of suitable linker sequences include $(GS)_5$ (GSGSGSGSGS; SEQ ID NO:149), $(GS)_{10}$ (GSGSGSGSGSGSGSGSGSGS; SEQ ID NO:150), $(G_4S)_3$ (GGGGSGGGGSGGGGS; SEQ ID NO:151), llama IgG2 hinge (AHHSEDPSSKAPKAPMA; SEQ ID NO:152) or human IgA hinge (SPSTPPTPSPSTPPAS; SEQ ID NO:153) linkers. Other non-limiting examples of suitable linker sequences are also described in the Example section.

Thus, according to specific embodiments, the amino acid (AA) linker sequence is a peptide of between 0 and 200 AA, between 0 and 150 AA, between 0 and 100 AA, between 0 and 90 AA, between 0 and 80 AA, between 0 and 70 AA, between 0 and 60 AA, between 0 and 50 AA, between 0 and 40 AA, between 0 and 30 amino acids, between 0 and 20 AA, between 0 and 10 amino acids, between 0 and 5 amino acids. Examples of sequences of short linkers include, but are not limited to, PPP, PP or GS.

For certain applications, it may be advantageous that the linker molecule comprises or consists of one or more particular sequence motifs. For example, a proteolytic cleavage site can be introduced into the linker molecule such that detectable label or moiety can be released. Useful cleavage sites are known in the art, and include a protease cleavage site such as Factor Xa cleavage site having the sequence IEGR (SEQ ID NO:154), the thrombin cleavage site having the sequence LVPR (SEQ ID NO:155), the enterokinase cleaving site having the sequence DDDDK (SEQ ID NO:156), or the PreScission cleavage site LEVLFQGP (SEQ ID NO:157).

Alternatively, in case the immunoglobulin single variable domain is linked to a detectable label or moiety using chemoenzymatic methods for protein modification, the linker moiety may exist of different chemical entities, depending on the enzymes or the synthetic chemistry that is used to produce the covalently coupled molecule in vivo or in vitro (reviewed in: Rabuka 2010, Curr. Opin. Chem. Biol. 14:790-796).

Diagnosis, Prognosis and Monitoring Therapy of Cardiovascular Diseases

One aspect hereof relates to an anti-MMR immunoglobulin single variable domain for use in diagnosing or prognosing a cardiovascular disease. In a preferred embodiment, the application envisages an anti-MMR immunoglobulin single variable domain for use in diagnosing or prognosing atherosclerosis or coronary heart disease.

Within the context of the disclosure, the term "cardiovascular disease," refers to an illness, injury, or symptoms related to an atherogenic process affecting the cardiovascular system. This includes the different stages marking the development of atherosclerotic plaques (different stages of plaques are classified according to guidelines such as those from the American Heart Association: neo-intimal, atheromatous, fibroatheromatous and collagen-rich lesions), as well as complications arising from the formation of an atherosclerotic plaque (stenosis, ischemia) and/or the rupture of an atherosclerotic plaque (thrombosis, embolism, myocardial infarction, arterial rupture, acute ischemic stroke). Cardiovascular disease refers, for example, to atherosclerosis, atherosclerotic plaques, especially the vulnerable plaques, coronary heart disease, thrombosis, stroke, myocardial infarction, vascular stenosis. Cardiovascular disease also refers to downstream complications of myocardial infarction or "post-infarction" complications due to ruptured plaques, including cardiac remodeling and cardiac failure.

"Atherosclerosis" herein refers to a disease affecting arterial blood vessels. Atherosclerosis can be characterized by a chronic inflammatory response in the walls of arteries, mainly due to the accumulation of macrophages and promoted by low density lipoproteins. The appearance of atherosclerotic plaques is a marker of atherosclerosis (also known as arteriosclerotic vascular disease or ASVD), which in itself is a typical cardiovascular disease and may lead to different cardiovascular complications, as described further herein. As used herein, the term "atherosclerotic plaque," refers to a deposit of fat and other substances that accumulate in the lining of the artery wall. The terms "vulnerable atherosclerotic plaque" or "instable atherosclerotic plaque" are used interchangeably herein and refer to atherosclerotic plaques with high likelihood of rapid progression and cardiovascular disease manifestations, including myocardial infarction and/or acute ischemic stroke. Unstable plaques are characterized by a large, soft lipid core that contains extracellular lipids and is covered by a thin fibrous cap, as well as an abundance of invasive inflammatory cells such as macrophages. In contrast, stable plaques have a small lipid core, thick fibrous caps, and little or no macrophage invasion with the development of fibrous tissue resulting in intimal thickening of the vessel. Atherosclerotic plaques formed by lipid accumulation in vessel lesions have a variety of characteristics, ranging from stable to unstable. Unstable plaques are prone to rupture followed by thrombus formation, vessel stenosis, and occlusion and frequently lead to acute myocardial infarction (AMI) and brain infarction. Thus, the specific diagnosis of unstable plaques would enable preventive treatments for AMI and brain infarction and represents a promising diagnostic target in clinical settings.

"Coronary heart disease" is the most common manifestation of cardiovascular disease. It is a progressive disease, due to poor irrigation of the heart muscle, and related to narrowing (stenosis) or calcification (sclerosis) of one or more coronary arteries. The complete blockage of one or more coronary arteries leads to a myocardial infarction.

The term "infarction" refers to a confined focal necrosis due to arterial obstruction. More specifically, myocardial infarction is myocardial necrosis, which usually results from acute coronary thrombosis following the rupture of a plaque (usually a vulnerable plaque), causing platelet aggregation and coronary occlusion.

The presence of a coronary plaque, especially if it is an unstable plaque, exposes the subject to a risk of myocardial infarction. The immunoglobulin single variable domains of the disclosure may, therefore, be used to detect a risk of occurrence of myocardial infarction in a patient.

"Risk of occurrence" is herein defined as the probability that an individual develops a disease.

"Acute ischemic stroke" refers to a decrease in the arterial blood supply to an area of the body. Its main causes are local thrombosis and embolism.

The term "thrombosis" refers to blood clotting in the vascular cavities (arteries, veins, capillaries and heart chambers) leading to the formation of a thrombus.

"Embolism" is the migration of an object, usually formed by a blood clot (thrombus), and its sudden stop in a vessel whose diameter is insufficient to let it pass. Local consequences of embolism are circulatory disturbances related to the vascular obstruction, most often leading to a heart attack.

The plaque can also be located at a carotid artery. These lesions lead to stroke, hemorrhagic events (aneurysm) or ischemic events (cerebral infarction). Therefore, the immunoglobulin single variable domains of the disclosure may be used to detect a risk of developing a stroke in a patient.

The plaque may also be located at a renal artery, the kidney being one of the target organs of atherosclerosis. Significant stenosis can lead to hypertension and/or renal failure. The atheromatous renal artery can also lead to an acute vascular event or kidney embolism. The immunoglobulin single variable domains of the disclosure can, therefore, also be used to detect a risk of occurrence of renal embolism in a patient.

Atherosclerotic plaques can also be located in the arteries of the lower limbs (risk of acute limb ischemia) or aorta (risk of aneurysm/dissection). The immunoglobulin single variable domains of the disclosure may be used to detect a risk of occurrence of limb ischemia or rupture of aortic aneurysm in a patient.

The term "cardiac remodeling" or "ventricular remodeling" refers to the changes in size, shape, structure and physiology of the heart after injury to the myocardium. The injury is typically due to acute myocardial infarction, but may be from a number of causes that result in increased pressure or volume overload (forms of strain) on the heart. Cardiac remodeling implies a decline in function. Cardiac remodeling is generally accepted as a determinant of the clinical course of cardiac failure.

The term "heart failure" or "cardiac failure," often called congestive heart failure or congestive cardiac failure, occurs when the heart is unable to provide sufficient pump action to maintain blood flow to meet the needs of the body. Common causes of heart failure include myocardial infarction and other forms of coronary artery disease, hypertension, valvular heart disease, and cardiomyopathy.

As used herein, the term "diagnosing" or grammatically equivalent wordings, means determining whether or not a subject suffers from a particular disease or disorder. As used herein, "prognosing" or grammatically equivalent wordings, means determining whether or not a subject has a risk of developing a particular disease or disorder.

Within the present context, the anti-MMR immunoglobulin single variable domains, as described hereinbefore, are particularly useful as contrast agent in non-invasive in vivo medical imaging, in particular for the targeting and/or detection of vulnerable atherosclerotique plaques. Preferably, a nuclear imaging approach is used. According to one specific embodiment, positron emission tomography (PET) is used for in vivo imaging with labeled anti-MMR immunoglobulin single variable domains. Alternatively, single photon emission computed tomography (SPECT) is used as in vivo imaging approach. Thus, in one embodiment, the anti-MMR immunoglobulin single variable domains, as described hereinbefore, are coupled to a detectable label, preferably a radioisotope. According to one embodiment, the diagnosing and/or prognosing of a cardiovascular disease, in particular atherosclerosis, will preferably be done by detecting the presence or absence of atherosclerotic plaques, in particular vulnerable atherosclerotic plaques. It may be of additional advantage that the evolution of the degree of vulnerability of atherosclerotic plaques can be monitored in function of time. More specifically, the disclosure allows to monitor progression or regression of vulnerability of atherosclerotic plaques in function of time. Hereby, different stages of plaques are classified according to guidelines such as those from the American Heart Association: neo-intimal, atheromatous, fibroatheromatous and collagen-rich lesions. A further advantage of the disclosure is the possibility to assess the impact of a therapy on atherosclerosis and/or the degree of vulnerability of atherosclerotic plaques and/or the evolution in function of time of the degree of vulnerability of atherosclerotic plaques, by making use of the anti-MMR immunoglobulin single variable domains, as described hereinbefore.

Also provided is a method of diagnosing or prognosing a cardiovascular disease, the method comprising the steps of administering to a subject an anti-macrophage mannose receptor (anti-MMR) immunoglobulin single variable domain wherein the immunoglobulin single variable domain is labeled with a detectable label. According to particular embodiments, the method may further comprising one or more of the following steps:

a. Monitoring the degree of vulnerability of atherosclerotic plaques and/or the evolution in function of time of the degree of vulnerability of atherosclerotic plaques, b. Assessing the impact of a therapy on the degree of vulnerability of atherosclerotic plaques and/or on the evolution in function of time of the degree of vulnerability of atherosclerotic plaques.

According to one embodiment of the above described method, the anti-macrophage mannose receptor (anti-MMR) immunoglobulin single variable domain is administered to the subject after the occurrence of a myocardial infarction, thus at the post-infarction stage.

Also envisaged is a method of in vivo imaging vulnerable atherosclerotic plaques in a subject, the method comprising the step of administering to a subject an anti-macrophage mannose receptor (anti-MMR) immunoglobulin single variable domain wherein the immunoglobulin single variable domain is labeled with a detectable label, and imaging vulnerable atherosclerotic plaques in the subject.

A variety of subjects or individuals can be diagnosed or prognosed or monitored in time. Generally the "subjects" are mammals or mammalian, where these terms are used broadly to describe organisms which are within the class mammalia, including dogs, cats, mice, guinea pigs, rats, rabbits, humans, chimpanzees, monkeys, etc. In particularly preferred embodiments, the subjects will be mice, rats, rabbits. In other preferred embodiments, the subjects will be humans.

Treatment of Cardiovascular Diseases

A particular aspect hereof relates to an anti-macrophage mannose receptor (anti-MMR) immunoglobulin single variable domain or a pharmaceutical composition comprising the same for use in the prevention and/or treatment of a cardiovascular disease, in particular atherosclerosis.

Accordingly, also provided is a method for the prevention and/or treatment of a cardiovascular disease, in particular atherosclerosis, the method comprising the step of administering to a subject in need thereof a therapeutically effective amount of an anti-MMR immunoglobulin single variable domain or a pharmaceutical composition comprising a therapeutically effective amount of an anti-MMR immunoglobulin single variable domain and at least one of pharmaceutically acceptable carrier, adjuvant or diluent. As a specific embodiment, the above method comprises administering to a subject a therapeutically effective amount of an anti-MMR immunoglobulin single variable domain coupled to a therapeutically active agent, or a pharmaceutical composition comprising a therapeutically effective amount of an anti-MMR immunoglobulin single variable domain coupled to a therapeutically active agent and at least one of pharmaceutically acceptable carrier, adjuvant or diluent.

As used herein, the terms "therapeutically effective amount," "therapeutically effective dose" and "effective amount" mean the amount needed to achieve the desired result or results. As used herein, "pharmaceutically acceptable" means a material that is not biologically or otherwise undesirable, i.e., the material may be administered to an individual along with the anti-MMR immunoglobulin single variable domain without causing any undesirable biological effects or interacting in a deleterious manner with any of the other components of the pharmaceutical composition in which it is contained.

A "carrier," or "adjuvant," in particular a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non-limiting example, Ringer's solution, dextrose solution or Hank's solution. Non aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

As used herein, the phrasing "preventing a disease" generally means inhibiting or reversing the onset of the disease, inhibiting or reversing the initial signs of the disease, inhibiting the appearance of clinical symptoms of the disease. As used herein, the phrasing "treating a disease" or "treating a subject or individual having a disease" generally means substantially inhibiting the disease, substantially slowing or reversing the progression of the disease, substantially ameliorating clinical symptoms of the disease or substantially preventing the appearance of clinical symptoms of the disease. A treatment is considered therapeutic if there is a decrease in mortality and/or morbidity, and may be performed prophylactically, or therapeutically. A variety of subjects or individuals are treatable. Generally the "subjects" are mammals or mammalian, where these terms are used broadly to describe organisms which are within the class mammalia, including dogs, cats, mice, guinea pigs, rats, rabbits, humans, chimpanzees, monkeys, etc. In particularly preferred embodiments, the subjects will be mice, rats, rabbits. In other preferred embodiments, the subjects will be humans.

According to specific embodiments, the disease that is targeted is a cardiovascular disease, in particular atherosclerosis, as defined hereinbefore. In particular, it includes reduction or preferably disappearance of vulnerable atherosclerotic plaques, and/or amelioration or alleviation of the symptoms of atherosclerosis.

It may be an advantage that the therapeutic method of the disclosure is used in combination with another therapy or treatment regimen for cardiovascular diseases, in particular for atherosclerosis. Accordingly, combination therapy is also encompassed in the disclosure. As a non-limiting example, it may be useful to combine the therapeutic method of the disclosure with the administration of drugs that lower cholesterol levels and that are effective in the prevention or treatment of cardiovascular diseases. Examples include the statins or HMG-CoA reductase inhibitors, of which a number are on the market: atorvastatin (Lipitor and Torvast), fluvastatin (Lescol), lovastatin (Mevacor, Altocor, Altoprev), pitavastatin (Livalo, Pitava), pravastatin (Pravachol, Selektine, Lipostat), rosuvastatin (Crestor), simvastatin (Zocor, Lipex). Several combination preparations of a statin and another agent, such as ezetimibe/simvastatin, are also available.

Routes of Administration

The anti-MMR immunoglobulin single variable domain (including a pharmaceutical composition comprising the same), optionally coupled to a therapeutically active agent, may be administered by any suitable method within the knowledge of the skilled man, by way of oral, inhaled or parenteral administration, in particular by intravenous injection. The anti-MMR immunoglobulin single variable domain may be administered alone or preferably formulated as a pharmaceutical composition. An amount effective to treat a certain disease or disorder that express the antigen recognized by the immunoglobulin single variable domain depends on the usual factors such as the nature and severity of the disorder being treated, the weight of the mammal, and if applicable, the nature of the therapeutically active agent. However, a unit dose will normally be in the range of 0.01 to 50 mg, for example, 0.01 to 10 mg, or 0.05 to 2 mg of immunoglobulin single variable domain or a pharmaceutically acceptable salt thereof. Unit doses will normally be administered once or more than once a day, for example, 2, 3, or 4 times a day, more usually 1 to 3 times a day, such that the total daily dose is normally in the range of 0.0001 to 1 mg/kg; thus, a suitable total daily dose for a 70 kg adult is 0.01 to 50 mg, for example, 0.01 to 10 mg or more usually 0.05 to 10 mg. It is greatly preferred that the immunoglobulin single variable domain or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tableting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminum stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid, and if desired conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing an immunoglobulin single variable domain of the disclosure and a sterile vehicle. The immunoglobulin single variable domain, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned. All these medicaments can be intended for human or veterinary use.

The efficacy of the immunoglobulin single variable domains of the disclosure, and of compositions comprising the same, can be tested using any suitable in vitro assay, cell-based assay, in vivo assay and/or animal model known per se, or any combination thereof, depending on the specific disease or disorder involved.

A further aspect of the disclosure relates to a method for producing an immunoglobulin single variable domain, according to the disclosure, the method comprising the steps of:

expressing, in a suitable host cell or expression system, a nucleic acid sequence encoding an immunoglobulin single variable domain, according to the disclosure; and optionally isolating and/or purifying the immunoglobulin single variable domain or the polypeptide.

Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the immunoglobulin single variable domains can be done according to techniques known by the skilled person in the art.

The following examples more fully illustrate preferred features of the disclosure, but are not intended to limit the disclosure in any way. Those having ordinary skill in the art and access to the teachings herein will recognize additional modifications and embodiments within the scope thereof. Therefore, the disclosure is limited only by the claims attached herein. All of the starting materials and reagents disclosed below are known to those skilled in the art, and are available commercially or can be prepared using well-known techniques.

EXAMPLES

Material and Methods to the Examples

Mice and Rabbits

Female Balb/c and C57BL/6 mice for biodistribution experiments in naïve animals were purchased from Harlan. C57BL/6 MMR-deficient mice were provided by Etienne Pays (Université Libre de Bruxelles). Female ApoE−/− and control C57Bl/6J mice were purchased from Charles River. ApoE−/− mice were fed a Western diet containing 0.25% cholesterol (Safe) for 18 weeks, whereas control mice remained on a standard chow diet. Myocardial-infarction prone Watanabe heritable hyperlipidemic rabbits were provided by Prof. Dr. Masashi Shiomi (Institute for Experimental Animals, Kobe University School of Medicine, Japan).

All animal studies were approved by and performed according to the guidelines of the institutional review board.

Generation and Production of Mono- and Bivalent Anti-Mouse MMR Nanobodies.

The anti-MMR Nanobody (Nb) clone 1 was isolated from an immune phage library in a similar way as described before (Saerens et al., 2004, J. Biol. Chem. 279:51965-72; Saerens et al., 2008, Immunol. Methods 329:138-50). In brief, an alpaca (*Vicugna pacos*) was immunized with 100 μg recombinant mouse MMR (R&D Systems) six times at weekly intervals. mRNA prepared from peripheral blood lymphocytes was used to make cDNA with the Ready-to-Go You-prime-first-strand beads (GE Healthcare). The gene sequences encoding the VHHs were PCR amplified using the CALL001/CALL002 and A6E/38 primer pairs. These PCR fragments were ligated into the pHEN4 phagemid vector after digestion with the PstI and BstEII restriction enzymes. Using M13K07 helper phage infection, the VHH library was expressed on phages and specific Nanobody-phages were enriched by several consecutive rounds of in vitro selection on microtiter plates (Nunc). Individual colonies were screened in ELISA for antigen recognition with non-specific phage particles serving as a negative control. The VHH genes of the clones that scored positive in ELISA were recloned into the expression vector pHEN6 using the restriction enzymes PstI and BstEII. Expression in the periplasm and purification of Nanobodies from *E. coli* periplasmic extracts using immobilized metal affinity chromatography (IMAC) on Ni-NTA resin (Sigma-Aldrich, St. Louis, Mo.) followed by size exclusion chromatography (SEC) on Superdex 75 HR 10/30 (Pharmacia, Gaithersburg, Md.) in phosphate buffered saline pH 7.4 (PBS) was performed as described previously (Conrath et al., 2001, Antimicrob. Agents Chemother. 45:2807-2812).

Bivalent Nanobodies were generated by recombinantly attaching a linker sequence 3' of the VHH sequence using PCR primer biNbF (5'-CCG GCC ATG GCC CAG GTG CAG CTT CAG GAG TCT GG AGG AGG-3'; SEQ ID NO:158) and primers biNbG4SR (5'-TGA TTC CTG CAG CTG CAC CTG ACT ACC GCC GCC TCC AGA TCC ACC TCC GCC ACT ACC GCC TCC GCC TGA GGA GAC GGT GAC CTG GGT C-3'; SEQ ID NO:159), biNbg2cR (5'-TGA TTC CTG CAG CTG CAC CTG TGC CAT TGG AGC TTT GGG AGC TTT GGA GCT GGG GTC TTC GCT GTG GTG CGC TGA GGA GAC GGT GAC CTG GGT C-3'; SEQ ID NO:160), biNbIgAR (5'-TGA TTC CTG CAG CTG CAC CTG ACT TGC CGG TGG TGT GGA TGG TGA TGG TGT GGG AGG TGT AGA TGG GCT TGA GGA GAC GGT GAC CTG GGT C-3'; SEQ ID NO:161) which code for a $(G_4S)_3$ (GGGGSGGGGSGGGGS; SEQ ID NO:162), llama IgG2 hinge (AHHSEDPSSKAPKAPMA; SEQ ID NO:163) or human IgA hinge (SPSTPPTPSPSTPPAS; SEQ ID NO:164) linker respectively. These PCR fragments were inserted 5' of the VHH gene in the original VHH expression vector with a PstI/BstEII restriction digest. After ligation, the resulting bivalent anti-MMR Nanobodies were expressed and purified as described above.

Generation of Anti-Human MMR and Anti-Human/Mouse MMR Cross-Reactive Nanobodies.

The anti-human macrophage mannose receptor (MMR) and anti-human/mouse MMR cross-reactive Nanobodies (Nbs) were isolated from an immune phage library in a similar way, as described before (Saerens et al., 2004, J. Biol. Chem. 279:51965-72; Saerens et al., 2008, Immunol. Methods 329:138-50). However, in order to generate cross-reactive Nbs, an alternating immunization schedule was carried out. An alpaca (*Vicugna pacos*) was immunized with 100 μg human MMR (R&D Systems #2534) followed by 100 μg mouse MMR (R&D Systems #2535) one week later. This alternating schedule was maintained for a total of 6 weeks and both proteins were mixed with the Gerbu adjuvant before injection. After immunization, blood was collected and the peripheral blood lymphocytes were isolated. mRNA was extracted from these cells using TRIzol (Invitrogen) and was reverse-transcribed with oligo(dT) and SuperScript II RT (Invitrogen), following the manufacturer's instructions. The gene sequences encoding the variable domains (VHHs) were PCR amplified, with the leader sequence specific CALL001 (5'-GTC CTG GCT CTC TTC TAC AAG G-3; SEQ ID NO:165) and CH2 exon specific CALL002 (5'-GGT ACG TGC TGT TGA ACT GTT CC-3'; SEQ ID NO:166) primers. After 1% agarose gel separation, the 600 bp fragment VHH-CH2 fragment was isolated from gel and re-amplified using the nested primers A6E (5'-GAT GTG CAG CTG CAG GAG TCT GGR GGA GG-3'; SEQ ID NO:167) and PMCF (5'-CTA GTG CGG CCG CTG AGG AGA CGG TGA CCT GGG T-3'; SEQ ID NO:168) specific for the framework-1 and framework-4 regions, respectively. These PCR fragments were ligated into the phagemid vector pMECS, a variant of pHEN4 (Arbabi Ghahroudi et al., 1997, FEBS Lett. 414:521-6), after digestion with the PstI and NotI restriction enzymes. The pMECS differs from the pHEN4 in coding for a HA (YPYDVPDYGS; SEQ ID NO:169) and 6× histidine tag fusion at the C-terminus of the Nb instead of a HA tag only fusion. Ligated material was transformed in freshly prepared *E. coli* TG1 cells and plated on LB plates with ampicillin. The colonies were scraped from the plates, washed and stored at −80° C. in LB-medium supplemented with glycerol (50% final concentration). Using M13VCS helper phage infection, the VHH library was expressed on phages. Specific Nanobody-phages were enriched by several consecutive rounds of in vitro selection on antigen coated to wells of microtiter plates (Nunc). For isolation of human/mouse MMR cross-reactive Nbs, screening was performed using human and mouse MMR alternatingly. Bound phage particles were eluted with 100 mM triethylamine (pH 11.0), immediately neutralized with 1 M Tris-HCl (pH 7.4) and used to infect *E.*

*coli* TG1 cells. Individual colonies were picked and expression of recombinant Nanobody-M13 protein III by addition of 1 mM isopropyl-β-D-thiogalac-topyranoside (IPTG). The periplasmic extract of each clone was subsequently tested in ELISA for human MMR recognition with non-specific antigen coated wells serving as a negative control. Human/mouse MMR cross-reactive Nbs were also screened in a similar fashion against mouse MMR, only clones reactive with both human and mouse antigens were withheld as cross-reactive Nbs. Each ELISA was performed on plates coated with 1 μg/ml MMR in 100 mM NaHCO$_3$ buffer pH=8.8. After coating the plates are washed with PBS+0.05% TWEEN®-20 (PEST) and blocked for 2 hours with PBS+0.05% TWEEN®-20+2% non-fat dry milkpowder (Nestle) (PBSM). The PE extracts are then incubated for 1 hour on the plate and then washed with PBST followed by 1 hour incubation of 0.5 μg/ml mouse anti-HA tag antibody (16B12, Covance) in PBSM. After washing with PBST, 1.5 μg/ml alkaline phosphatase conjugated anti-mouse antibody (Sigma) in PBSM in added to the plate for 1 hour followed by PBST washing. Finally, the ELISA is developed using 2 mg/ml alkaline phosphatize substrate (Sigma) in AP-buffer (100 mM NaCl, 50 mM MgCl$_2$, 100 mM Tris pH=9.5) and the optical density signal at 405 nm is measured.

Expression and Purification of Anti-Human MMR and Anti-Human/Mouse MMR Cross-Reactive Nanobodies.

Figure 6A:
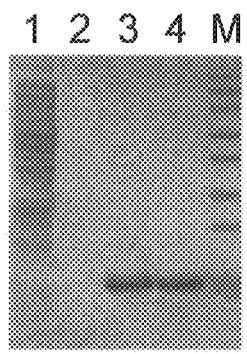
FIG. 6: Purification of a number of selected Nb clones. A. Coomassie stained 12% SDS-PAGE gel loaded with protein fractions after IMAC purification of NbhmMMRm5.38 periplasmic extract. Lane 1, column flowthrough, lane 2, wash fraction, lane 3 and 4, elution fractions, M indicates a molecular weight ladder. B. Chromatogram of IMAC purified Nb5.38 samples run on a S75 gelfiltration column in PBS. Solid line depicts the OD 280 nm, dotted line depicts conductivity, dashed line depicts pH. Only fractions in the main Nb peak around fraction 30 were withheld for further experiments. C. Coomassie stained 12% SDS-PAGE gel loaded with protein fractions after gelfiltration of NbhmMMRm3.1 (lane 1), NbhmMMRm14.4 (lane 2), NbhmMMRm5.38 (lane 3), NbhmMMRm26.70 (lane 4) and NbhmMMRm3.49 (lane 5). M indicates a molecular weight ladder. All Nbs were confirmed to be >95% pure and have sizes of 13-15 kDa.

The pMECS-Nb plasmids of the clones that scored positive in ELISA were transformed into *E. coli* WK6 cells. These cells stop translation at the TAG codon and, therefore, express the Nbs without a phage protein fusion. Production of recombinant VHH was performed in shaker flasks by growing the bacteria in Terrific Broth supplemented with 0.1% glucose and ampicillin until an absorbance at 600 nm between 0.6 and 0.9 was reached. VHH expression was then induced with 1 mM IPTG for 16 h at 28° C. After pelleting the cells, the periplasmic proteins were extracted by osmotic shock. This periplasmic extract was loaded on a nickel-nitrilotriacetic acid (Thermo Scientific), and after washing, the bound proteins were eluted in PBS with 500 mM imidazol. The eluted fraction of this immobilized metal affinity chromatography (IMAC) was dialyzed to Vivaspin 2 centrifugal concentrators (Sartorius). The final purity of the protein was checked by SDS-PAGE (FIG. 6A). The final yield was determined from UV absorption at 280 nm using the calculated theoretical extinction coefficient of the VHH.

Figure 6C:
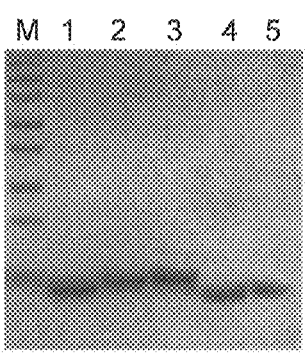
Figure 6B:
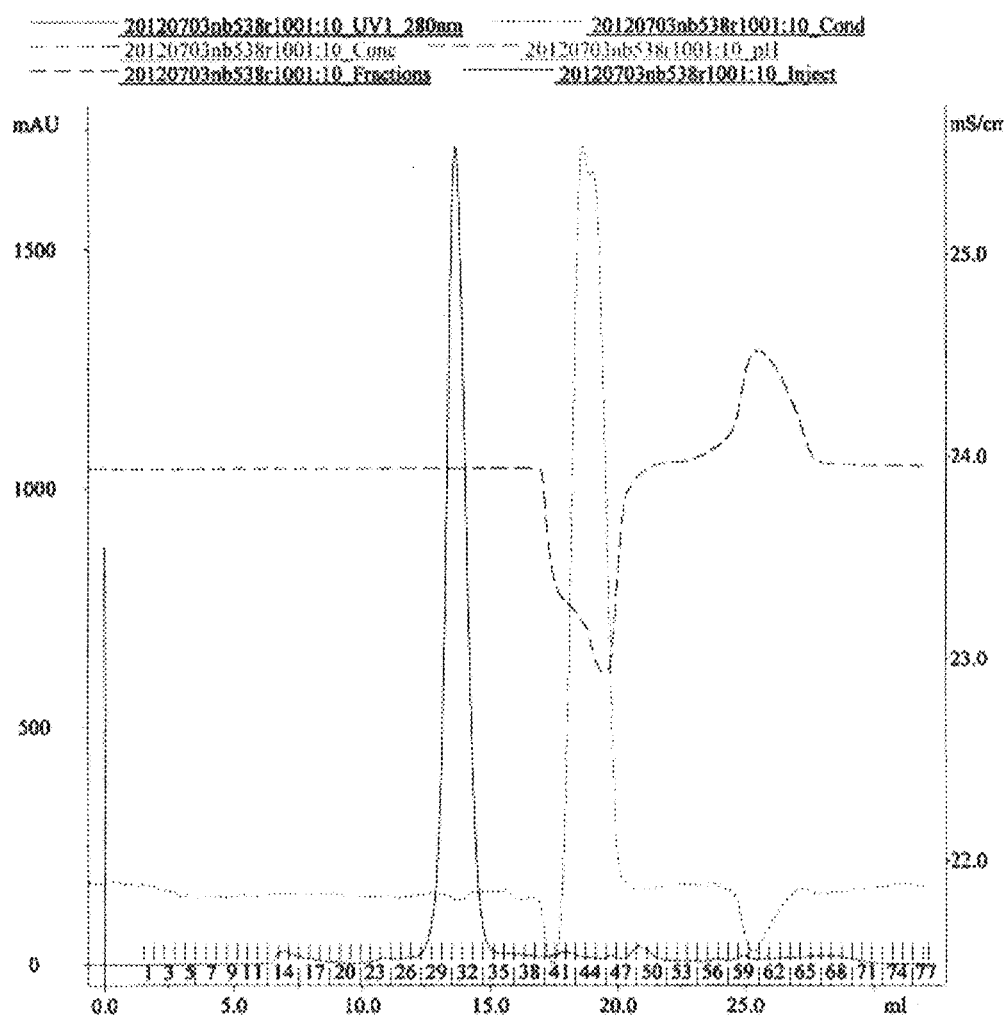

A HA tag is useful for detection of Nanobodies via flow cytometry, but has been shown to interfere with 99mTc labeling on adjacent His tags. Therefore, for experimental tests involving 99mTc labeling, the Nanobodies were recloned to the pHEN6c vector. This removes the HA tag and only fuses a 6xHis tag at the C-terminus of the Nanobody. In addition, after periplasmic expression and IMAC purification, Nanobodies to be used in experiments involving 99mTc labeling were subjected to an additional purification step via size exclusion chromatography, as described above, for the anti-mouse MMR Nanobodies (FIGS. 6B and 6C).

Surface Plasmon Resonance

Affinity analysis was performed using a BIAcore T100 (GE Healthcare) with HEPES-buffered saline running buffer (10 mM HEPES with 0.15 M NaCl, 3.4 mM EDTA and 0.005% surfactant P20 at pH 7.4). MRR was immobilized on a CM5 chip in acetate buffer 50 mM (pH 5.0), resulting in 2100 RU MMR coated on the chip. A second channel on the same chip was activated/deactivated in a similar way and served as a negative control. The MMR Nanobodies were used as analytes in 11 different concentrations, ranging from 1 to 2000 nM, at a flow rate of 10 ml/min. Glycine-HCl 50 mM (pH 2.0) was used for elution. The kinetic and equilibrium parameters (kd, ka and $K_D$) values were calculated from the combined sensogram of all concentrations using BIAcore T100 evaluation software 2.02 (GE Healthcare).

Cell Preparation and Flow Cytometry

The Nanobodies used for flow cytometry staining were produced from the original pMECS phage vector and, therefore, each Nanobody possesses a C-terminal HA and 6xHis tag.

For examining specific binding of the anti-MMR Nanobodies to mouse MMR, 3LL-R tumors were induced by injecting 3E6 cancer cells subcutaneously in C57Bl/6 mice. After 15 days of tumor growth, the tumors were isolated, chopped and incubated for 25 minutes (37° C.) with 10 U/ml Collagenase type I, 400 U/ml Collagenase type IV and 30 U/ml DNAseI (Worthington). Density gradients (Axis-Shield) were used to remove tissue debris and dead cells. Nanobodies were added at 10 μg/ml to 1E6 cells per tube. After at least one hour of incubation with anti-MMR Nanobody or control Nanobody, cells were washed two times with ice-cold Hank's Buffered Salt Solution (HBSS) buffer (containing 0.74 g/l EDTA and 0.5% (v/v) heat inactivated fetal calf serum) and incubated with 0.5 μg/ml Alexa Fluor 488 conjugated anti-HA tag monoclonal antibody (clone 16B12, Invitrogen). Commercial antibodies used for cell surface stainings were Alexa Fluor 647 conjugated anti-mouse Ly6C monoclonal antibody (clone ER-MP20, AbD Serotec), PerCPCy5.5 conjugated anti-mouse MHCII monoclonal antibody (clone M5/114.15.2, Biolegend), Phycoerythrin conjugated anti-mouse Ly6G monoclonal antibody (clone 1A8, BD Biosciences). For flow cytometry measurements, CD11b+Ly6G-tumor associated macrophages were further gated on MHCII expression, as the MHCII$^{low}$ TAMs express MMR to a high degree. Binding profiles of anti-MMR Nanobodies were recorded.

In order to examine binding of the Nanobodies to human MMR, human immature dendritic cells were used. Cryopreserved immature dendritic cells derived from healthy human donor monocytes were a kind gift of Dr. Karine Breckpot (Vrije Universiteit Brussel, Jette, Belgium). To prepare the immature dendritic cells, peripheral blood mononuclear cells were removed from the blood via leukapheresis and monocytes were separated by adherence to plastic Nunclon dishes (Nunc, Biotech Line, Slangerup, Denmark). After removal of the non-adherent cells, immature dendritic cells were in vitro generated during a six days differentiation from monocytes in RPMI 1640 medium supplemented with 500 U/ml IL-4 (Invitrogen) and 1000 U/ml GM-CSF (Gentaur). Cells were harvested at day 6, counted and aliquoted at 1E7 cells/vial. The cells were cryopreserved in 85% autologous serum, 10% DMSO (Sigma-Aldrich) and 5% Glucosteril 40% (Fresenius, Albertslund, Denmark). For flow cytometry analysis, cells were thawed on ice and incubated for more than one hour at room temperature with precooled RPMI 1640 medium supplemented with 500 U/ml IL-4 (Invitrogen) and 1000 U/ml GM-CSF (Gentaur). Next, 10% normal rabbit serum was added to prevent aspecific Fc mediated binding of antibodies. After half an hour the Nanobodies were added at 10 μg/ml to 2E5 cells per tube. After at least one hour of incubation with anti-MMR Nanobody or control Nanobody, cells were washed two times with ice-cold HBSS buffer supplemented with 1% normal rabbit serum (Eppendorf 5810-R Centrifuge, 8 minutes, 1400 rpm, 4° C.) and incubated with 0.5 μg/ml Alexa Fluor 488 conjugated anti-HA tag monoclonal antibody (clone 16B12, Invitrogen). Allophycocyanin conjugate (APC) conjugated anti-human CD11c monoclonal antibody (clone B-ly6, BD Biosciences) was used for CD11c staining. Stained cells were washed once more with ice-cold HBSS buffer supplemented with 1% normal rabbit serum (Eppendorf 5810-R Centrifuge, 8 minutes, 1400 rpm, 4° C.) and analyzed by flow cytometry.

Nanobody Labeling and In Vitro Characterization of $^{99m}$Tc-Labeled Nanobodies For labeling of Nanobodies with $^{99m}$Tc at their hexahistidine tail, [$^{99m}$Tc(H$_2$O)$_3$(CO)$_3$]$^+$ was synthesized by adding 1 mL of $^{99m}$TcO4$^-$ (0.74-3.7 GBq) to an Isolink kit (Mallinckrodt Medical BV) containing 4.5 mg of sodium boranocarbonate, 2.85 mg of sodium tetraborate.10H$_2$O, 8.5 mg of sodium tartrate.2H$_2$O, and 7.15 mg of sodium carbonate, pH 10.5. The vial was incubated at 100° C. in a boiling bath for 20 minutes. The freshly prepared [$^{99m}$Tc(H$_2$O)$_3$(CO)$_3$]$^+$ was allowed to cool at room temperature for 5 minutes and neutralized with 125 µL of 1 M HCl to pH 7-8. [$^{99m}$Tc(H$_2$O)$_3$(CO)$_3$]$^+$ was added to 50 µL of 1 mg/mL monovalent Nanobody or 2 mg/ml bivalent Nanobody, together with 50 µL of carbonate buffer, pH 8. The mixture was incubated for 90 minutes at 52° C. in a water bath. The labeling efficiency was determined by instant thin-layer chromatography in acetone as mobile phase and analyzed using a radiometric chromatogram scanner (VCS-201; Veenstra). When the labeling yield was less than 90%, the $^{99m}$Tc-Nanobody solution was purified on a NAP-5 column (GE Healthcare) pre-equilibrated with phosphate-buffered saline (PBS) and passed through a 0.22 µm Millipore filter to eliminate possible aggregates.

Pinhole SPECT-microCT Imaging Procedure

Mice were intravenously injected with 100-200 µl 45-155 MBq (about 5-10 µg) of $^{99m}$Tc-Nanobody. Mice were anesthetized with a mixture of 18.75 mg/kg ketamine hydrochloride (KETAMINE 1000°, CEVA, Brussels, Belgium) and 0.5 mg/kg medetomidin hydrochloride (DOMITOR®, Pfizer, Brussels, Belgium) 10-15 minutes before pinhole SPECT acquisition.

MicroCT imaging was followed by pinhole SPECT on separate imaging systems. MicroCT was performed using a dual source CT scanner (Skyscan 1178, Skyscan, Aartselaar, Belgium) with 60 kV and 615 mA at a resolution of 83 µm. The total body scan time was 2 minutes. Image reconstruction was performed using filtered backprojection (Nrecon, Skyscan, Aartselaar, Belgium). Total body pinhole SPECT was performed at 60 minutes or 180 minutes post-injection (p.i.) using a dual headed gamma camera (e.cam$^{180}$ Siemens Medical Solutions, IL, USA), mounted with two multi-pinhole collimators (3 pinholes of 1.5 mm in each collimator, 200 mm focal length, 80 mm radius of rotation). Images were acquired over 360 degrees in 64 projections of 10 s into 128×128 matrices resulting in a total imaging time of 14 minutes. The SPECT images were reconstructed using an iterative reconstruction algorithm (OSEM) modified for the three pinhole geometry and automatically reoriented for fusion with CT based on six $^{57}$Co landmarks.

Image Analysis

Image viewing and quantification was performed using AMIDE Medical Image Data Examiner software. Ellipsoid regions of interest (ROIs) were drawn around the tumor and major organs. Uptake was calculated as the counts in the tissue divided by the injected activity counts and normalized for the ROI size (% IA/cm$^3$). High-resolution image 3D-reconstructions were generated using OsiriX Imaging Software.

Biodistribution Analysis 30 minutes after microCT/SPECT acquisition, mice were sacrificed with a lethal dose of pentobarbital (Nembutal; CEVA). Aorta, kidneys, liver, lungs, muscle, spleen, lymph nodes, bone, heart, and blood were removed and weighed, and the radioactivity was measured using an automated γ-counter (Cobra II Inspector 5003; Canberra-Packard). Tissue and organ uptake was calculated as percentage of injected activity per gram of tissue (% IA/g), corrected for decay. For analysis of aorta targeting, aortas were cut into 12 segments and radioactivity of each segment was measured separately. A lesion-extension index was attributed to each segment as shown in the inset of FIG. X: (−) no lesion (control segments), (+) lesion covering up to 50% of the arterial segment length, (++) lesions covering more than 50% of the arterial segment length, and (+++) lesions extending over the whole segment length. Aortic lesion and control uptakes were defined as the average uptake in all segments ranked (+++) or (−), respectively.

In Vivo Assessment of Cross-Reactivity in Rabbits

To assess in vivo cross-reactivity in rabbits, anti-MMR nanobodies were labeled with $^{99m}$Tc via tricarbonyl chemistry as described above. WHHLMI rabbits (male, ±2 months old, 1.5-1.9 kg) were anesthetized by intramuscular injection of 35 mg/kg ketamine and 5 mg/kg xylazine. $^{99m}$Tc-nanobody (300±65 MBq) was injected intravenously via the marginal ear vein. The animals were immediately subjected to dynamic planar imaging using a γ-camera (e.cam$^{180}$ Siemens Medical Solutions, Wheaton, Ill., USA) making acquisitions every 10 seconds during 60 minutes with the following camera settings: 256×256 matrix and zoom factor 1.78. At the end, animals were killed by intravenous injection of 100 mg/kg pentobarbital and all major organs and tissues were harvested. The organs and tissues were weighted and radioactivity in representative samples was counted in a γ-well counter (Cobra II Inspector 5003, Canberra-Packard). Results were corrected for background and decay, and expressed as percentage of injected activity per organ or as differential uptake ratio (DUR, calculated as (tissue activity/tissue weight)/(injected activity/animal body weight) (% ID/g/kg).

Statistics

Statistical significance was determined by the Student's t test, using Microsoft Excel or GraphPad Prism 4.0 software. Differences were considered significant when P≤0.05. Geometric means and confidence intervals were determined using Microsoft Excel.

18F Labeling of Nanobodies

[$^{18}$F]-fluoride was obtained through the nuclear reaction $^{18}$O(p,n) $^{18}$F by bombarding 18 MeV accelerated protons on >95% $^{18}$O enriched water (Campro, the Netherlands) in a CGR 560 cyclotron. After transfer to a S$_{YNTH}$ERA® module (IBA Molecular, Belgium), the resultant [$^{18}$F]-fluoride was separated from $^{18}$O-enriched water on a SEP-PAK® Light Accell plus QMA anion exchange cartridge (Waters, US). The anion exchange cartridge was pre-conditioned sequentially with 5 ml of 8.4% NaHCO$_3$ (VWR, Belgium) and 5 ml of deionized water. The [$^{18}$F] was eluted from the cartridge using 600 µl of a solution containing 4.2 mg K$_2$CO$_3$ and 22.6 mg Kryptofix 2.2.2 (K$_{222}$) in acetonitrile/water (1:1) (vial 1) (ABX, Germany). The solvent was evaporated under a stream of nitrogen at 110° C. to generate the anhydrous K$_{222}$/K[$^{18}$F] F complex.

$^{18}$F-labeling of Nanobodies was performed using the prosthetic group N-succinimidyl-4-[$^{18}$F] fluorobenzoate ([$^{18}$F]-SFB). The [$^{18}$F]-SFB prosthetic group was produced using a disposable $^{18}$F-FDG cassette (IFP™ nucleophilic, IBA Molecular). A solution of 4 mg (0.011 mmol) Ethyl 4-[Trimethylammonium]Benzoate (ABX, Germany) in 2 ml DMSO (vial 2)(Sigma-Aldrich, Belgium) was added to the dried [$^{18}$F] complex in the reaction vial which was heated to 110° C. for 15 minutes to produce ethyl-4-[$^{18}$F]fluorobenzoic acid. This intermediate was hydrolyzed adding 20 µl (0.02 mol) of an 0.1 M aqueous tetrapropylammoniumhydroxide (TPAOH) solution in 0.5 ml DMSO (vial 3) and subsequently activated with 26 mg (0.072 mmol) of the coupling agent N,N,N',N'-Tetramethyl-O—(N-succinimidyl)uronium hexafluorophosphate (HSTU) in 1 ml CH$_3$CN (vial 4) to form N-succinimidyl 4-[$^{18}$F]fluorobenzoate ([$^{18}$F]-SFB). Unpurified [$^{18}$F]-SFB was transferred to a vial containing 4 ml 5% acetic acid solution and 8 ml 0.9% NaCl-solution. The purification was optimized using only one solid phase extraction cartridge. This purification was performed on a second SYNTHERA® module using an in-house made automatic three-way valve to transfer the diluted [$^{18}$F]-SFB and washing solution. Afterwards the [$^{18}$F]-SFB was dried in a conical vial by means of gentle heating in nitrogen environment. After evaporation the Nanobody solution, in a 0.1 M borate buffer, was added to the dried residue in the reaction vessel and allowed to react for 20 minutes at room temperature. The labeling of Nanobody and purification by size exclusion chromatography using a PD-10 column (GE Healthcare) were performed on a semi-automatic in-house made system connected to the SYNTHERA® module and transferred in a vial after passing a 0.22 µm filter (Millipore). The final purified $^{18}$F-FB-anti-MMR was collected in a solution of phosphate buffered saline pH 7.4.

Overall, [$^{18}$F]-SFB was synthesized and purified using two SYNTHERA® modules (IBA Molecular) with a radiochemical yield of 50-60% (decay corrected). Two- to five hundred MBq of $^{18}$F-FB-anti-MMR Nanobody was obtained with a radiochemical purity of more than 97% and overall radiochemical yield of 5% using the fully automated protocol.

PET/CT Imaging Procedure

Male Watanabe rabbits of 13-16 months old were used for PET imaging. 18F-labeled nanobodies were injected via marginal ear vein. The dose at injection was: 0.5-1 mCi (50-100 µg nanobody). PET/CT Imaging was performed at 2 hours-2.5 hours post-injection.

The PET scan was performed on a Philips Gemini TF64 PET/CT; PET images were acquired over 24-28 minutes (6-7 bed positions, with 4 minutes per position) and reconstructed to 300-342 slices of 288×288 pixels (at 2 mm isotropic voxel size), with attenuation correction based on the CT data. The parameters of the CT scan were: 120 kV at approx. 30 mA with voxel size of 2 mm, using filtered backprojection. Total CT scan time was approx. 20 seconds. Xenetix was used as CT contrast, which was injected manually into marginal ear vein just prior to the CT acquisition, after the scout scan.

Myocardial Ischemia/Reperfusion Injury (IRI) Rat Model

Myocardial IRI was induced by ligation of the left anterior descending coronary artery during 60 minutes followed by loosening of the suture in 17 Wistar rats. Seven animals were sham operated. The infarct size was assessed by a $^{99m}$Tc-Tetrofosmin scan on day 2. Pinhole-SPECT/µCT acquisitions of $^{99m}$Tc-MMR-Nb were taken at baseline, at day (D) 5, 9, 12, 16, 21, 28 and 3 months after IRI. Quantification of the uptake of $^{99m}$Tc-MMR-Nb in the infarct zone (IZ) was performed by measuring the absolute mean uptake at the anterolateral segment of equally sized volumes of interest. Immunofluorescence staining was performed with an anti-MMR antibody and an anti-CD68 antibody. Statistical analysis was conducted using repeated measures ANOVA on log-transformed data. Data are shown as mean±standard deviation and significance was set to 0.05. As a control, in vivo quantification of a $^{99m}$Tc labeled control-Nb (cAbBCII10) is being performed.

Example 1

Generation of Nanobodies Against the Mouse Macrophage Mannose Receptor (CD206-MMR)

Anti-CD206 (anti-MMR) Nanobodies (Nbs), which are the smallest available antigen-binding entities, were created in order to target MMR-positive cells in vivo. Nanobodies were raised against the recombinant extracellular portion of MMR, as described in the Materials and Methods (see also Table 1). The binding characteristics of the monovalent anti-MMR Nanobodies were compared using surface Plasmon resonance (SPR) measurements (Table 2). Nanobody clone 1 demonstrated an 8-fold higher apparent affinity for immobilized recombinant MMR compared to Nanobody clone 3 ($K_D$=2.31×10$^{-8}$ M versus 1.91×10$^{-7}$ M, respectively), and became hence the Nanobody of choice for the remaining of this study. In addition, SPR competition studies demonstrated that pre-treatment with Nanobody clone 1 does not preclude Nanobody clone 3 binding, and vice versa, suggesting that anti-MMR Nb clone 1 and Nb clone 3 bind to non-overlapping epitopes (data not shown).

Example 2

In Vivo Imaging with Anti-Mouse Macrophage Mannose Receptor Nanobodies in Naive Mice Using Pinhole SPECT/Micro-CT Analysis In a next step, we performed in vivo imaging using Macrophage Mannose Receptor (MMR) targeting Nanobody clone 1. The Nanobodies were labeled at their hexahistidine-tail with $^{99m}$Tc at elevated temperatures by tricarbonyl-chemistry. Purified, $^{99m}$Tc-labeled Nanobodies were injected intravenously in mice and total body scans were made using pinhole SPECT and microCT.

The first step in the in vivo evaluation was the study of the biodistribution in healthy mice. This allows to evaluate physiological sites of specific accumulation and to determine the pharmacokinetic properties of the imaging probes. MMR Nanobodies show uptake in organs such as lungs, spleen and liver. The blood clearance is fast with less than 1% IA (injected activity)/ml remaining in blood at 1 hour 30 minutes post injection. We also tested MMR Nanobodies in MMR knock-out mice where the uptake in liver and spleen dropped below 1% IA/g (FIG. 1). These data indicate that the accumulation in organs such as liver and spleen is related to MMR expression and, therefore, specific. Only the accumulation in lungs appears to be MMR-unrelated.

Example 3

Generation of Anti-MMR Bivalent Nanobodies

Bivalent Nanobodies were constructed by linking two anti-MMR Nanobody 1 entities using (G$_4$S)$_3$ (GGGGSGGGGSGGGGS; SEQ ID NO:151), llama IgG2 hinge (AHHSEDPSSKAPKAPMA; SEQ ID NO:152) or human IgA hinge (SPSTPPTPSPSTPPAS SEQ ID NO:153) linkers. These bivalent anti-MMR molecules showed a 5-fold higher avidity compared to the monovalent clone 1 Nanobody, which can be attributed largely to 3-fold increase in $K_D$. The different linkers used for bivalent Nanobody construction did not seem to have a significant effect on the affinity of the molecules for the MMR antigen. As a negative control Nanobody in all experiments, we consistently used α-BCII10 Nb, which is a binder of the β-lactamase BCII enzyme of *Bacillus cereus*.

Example 4

Figure 2:
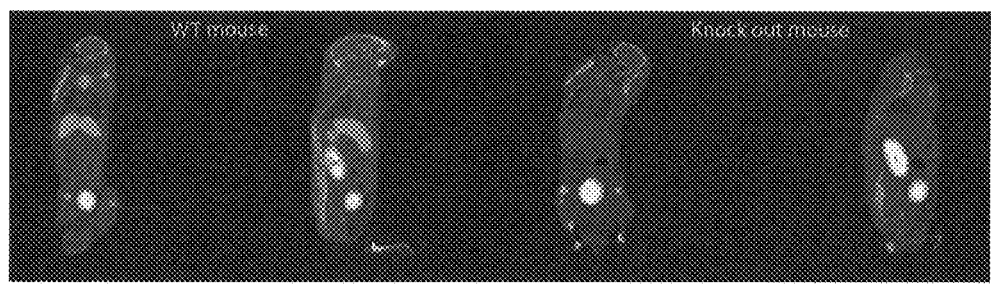
FIG. 2: Coronal and sagittal views of fused Pinhole SPECT and Micro-CT images of naive WT or MMR$^{-/-}$ mice 1 hour after injection with $^{99m}$Tc labeled anti-MMR Nb clone 1. (A) In WT mice anti-MMR Nb shows kidney/bladder elimination and uptake in several organs. (B) In MMR$^{-/-}$ mice anti-MMR Nb shows primarily kidney/bladder elimination.

Assessment of the Biodistribution and Specificity of Anti-MMR Nanobody Clone 1 and its Bivalent Derivative in Naive Mice Using Pinhole SPECT/Micro-CT Analysis Next, we wished to assess whether the anti-MMR Nb clone 1 and its bivalent derivative could be used for targeting and imaging of MMR-expressing cells in vivo. To this end, anti-MMR monovalent Nb were labeled with $^{99m}$Tc and injected intravenously in naive C57BL/6 mice. 3 hours post injection, total-body scans were acquired using pinhole SPECT and micro-CT (FIG. 2), images were quantified and tracer uptake expressed as percentage injected activity per gram cubic centimeter (% IA/cm$^3$) (Table 3). To ascertain the specificity of the anti-MMR Nb and to prove that any potential targeting was not due to aspecific retention, anti-MMR Nb were also injected in naive C57BL/6 MMR$^{-/-}$ mice. In MMR$^{-/-}$ mice, SPECT/micro-CT images show a high tracer uptake in the kidneys and urinary activity in the bladder, indicative of renal clearance, but only low background-level retention is seen in other organs (FIG. 2; Table 3). The only exception was the lungs, suggesting that lung-targeting was aspecific. In contrast, WT mice showed an increased retention of the anti-MMR Nb in several organs, including heart, bone, spleen and liver, with the latter two showing the most intense signals (FIG. 2). These results indicate that the anti-MMR monovalent Nb has a high in vivo specificity and can efficiently target organs such as the liver and spleen. A similar experiment was performed with the different bivalent anti-MMR Nb constructs, all of which showing an even increased uptake in the liver as compared to the monovalent molecule and a concomitant reduction in clearance via the kidneys (Table 4). Again, retention of bivalent anti-MMR Nb in all organs, except the lung, is MMR-specific and is absent in MMR$^{-/-}$ mice. As was expected, retention of the control cAbBCII10 Nb is very low in all organs, resulting in a massive clearance via the kidneys (Table 4).

Example 5

Selection of Anti-Human MMR Nbs

Figure 3:
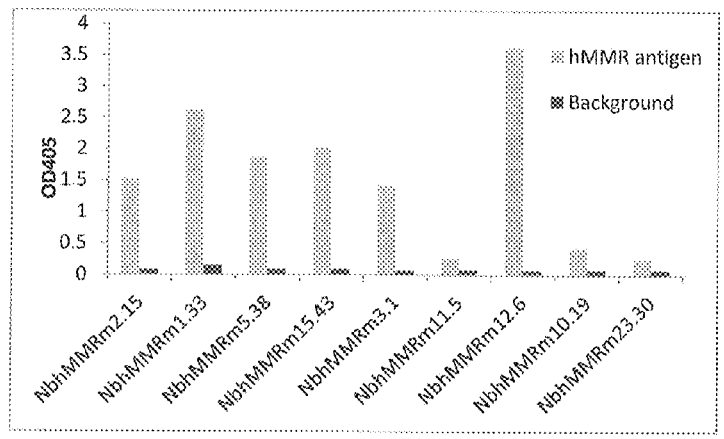
FIG. 3: PE-ELISA on human MMR. Summary of the selected anti-human MMR Nb clones. A clone was selected when the OD405 nm was at least 3 times higher on specific antigen as compared to irrelevant milk blocking proteins.

Next, anti-human MMR Nanobodies were generated (see also Material and Method section). After 4 panning rounds of an anti-human/anti-mouse MMR phage bank on human MMR, up to 100 fold enrichments for hMMR reactive phages were observed per panning round. Therefore, 188 colonies from all rounds were selected for PE-expression. These PE-extracts were used in PE-ELISAs to determine which clones react effectively to hMMR. In total 100 clones were selected based on these results (FIG. 3). Additionally, the DNA and protein sequence of the selected clones was determined (Table 5) and double clones or premature stopping clones were discarded.

Example 6

Selection of Anti-Human/Mouse MMR Cross-Reactive Nbs

Figure 4:
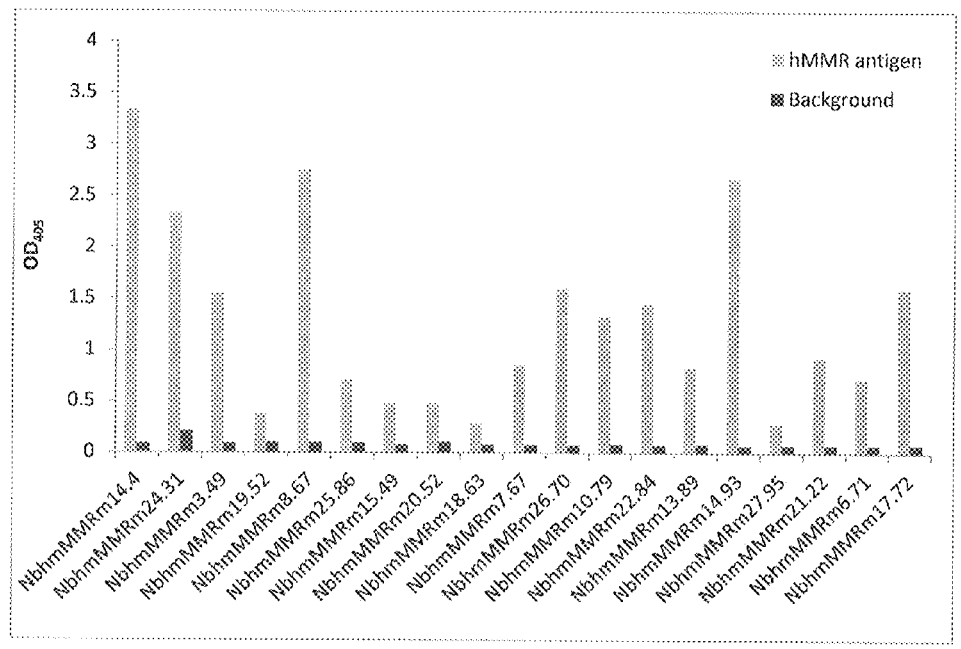
FIG. 4: PE-ELISA on human MMR. Summary of the selected anti-human/mouse MMR cross-reactive Nb clones. A clone was selected when the OD405 nm was at least 3 times higher on specific antigen as compared to irrelevant milk blocking proteins.
Figure 5:
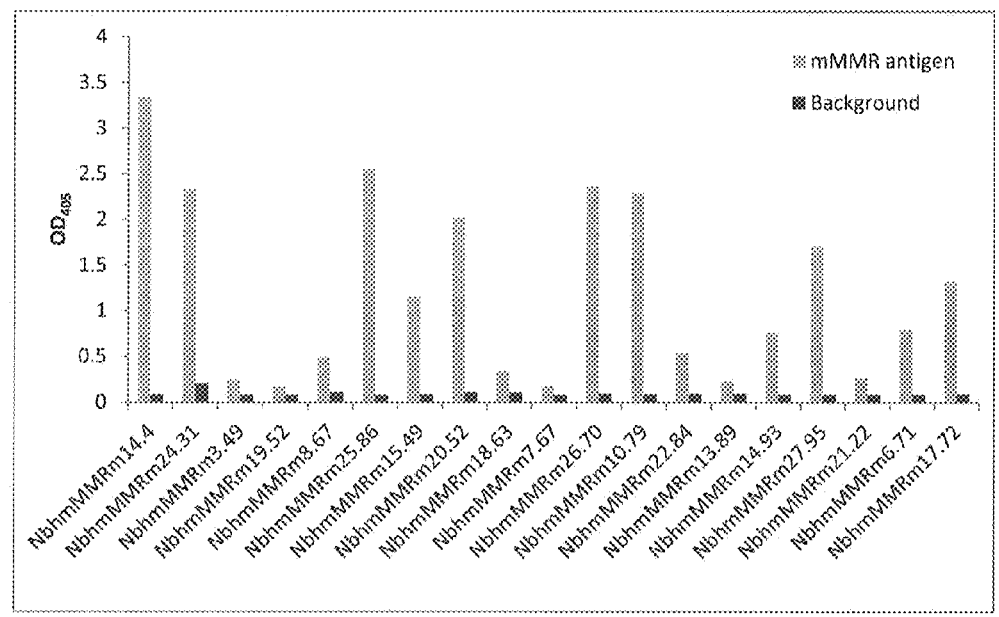
FIG. 5: PE-ELISA on mouse MMR. Summary of the selected anti-human/mouse MMR cross-reactive Nb clones. A clone was selected when the OD405 nm was at least 2 times higher on specific antigen as compared to irrelevant milk blocking proteins.

Next, anti-human/mouse MMR cross-reactive Nanobodies were generated (see also Material and Method section). The anti-human/anti-mouse MMR phage bank was alternatingly screened on human and mouse MMR for a total of 4 rounds, resulting in up to 100 fold enrichments for hMMR/mMMR reactive phages from the second panning round. Therefore, 188 colonies from the second and third rounds were selected for PE-expression. These PE-extracts were used in PE-ELISAs to determine which clones react effectively to MMR, clones were selected after the ELISA on hMMR (FIG. 4). These clones were then screened for binding on mouse MMR (FIG. 5). Only clones (42) that reacted to both antigens were withheld as true cross-reactive Nbs. These clones were sequenced (Table 6) and divided into families based on their CDR3 regions.

Example 7

Production of Representative Set of Anti-Human or Anti-Human/Mouse MMR Nbs

A set of representative clones was selected for Nb production in *E. coli*: (1) anti-human Nbs: NbhMMRm1.33, NbhMMRm4.83, NbhMMRm10.19, NbhMMRm23.30, NbhMMRm2.15, NbhMMRm3.1, NbhMMRm5.38, NbhMMRm12.6, NbhMMRm11.5, NbhMMRm15.43, NbhMMRm16.95; (2) anti-human/mouse Nbs: NbhmMMRm14.4, NbhmMMRm6.71, NbhmMMRm24.31, NbhmMMRm20.52, NbhmMMRm3.49, NbhmMMRm22.84, NbhmMMRm19.52, NbhMMRm21.22, NbhmMMRm14.93, NbhmMMRm15.49, NbhmMMRm17.72, NbhmMMRm10.79, NbhmMMRm7.67, NbhmMMRm26.70. Each clone was grown in a two liter culture. After expression and osmotic shock, the resulting extract was purified on 1 ml of Ni-NTA resin. The resulting 5 ml of eluted Nb was dialyzed to PBS after which the concentration was determined using a Nanodrop device and purity was assessed on Coomassie stained SDS-PAGE gels (example for NbhmMMRm5.38 in FIG. 6A). The Nanobodies all produced between 0.7 and 9 mg Nb/l *E. coli* culture (Table 7).

Example 8

Determination of Kinetic Rate Constants of a Representative Set of Anti-Human or Anti-Human/Mouse MMR Nbs Via Surface Plasmon Resonance (SPR)

Figure 7A:
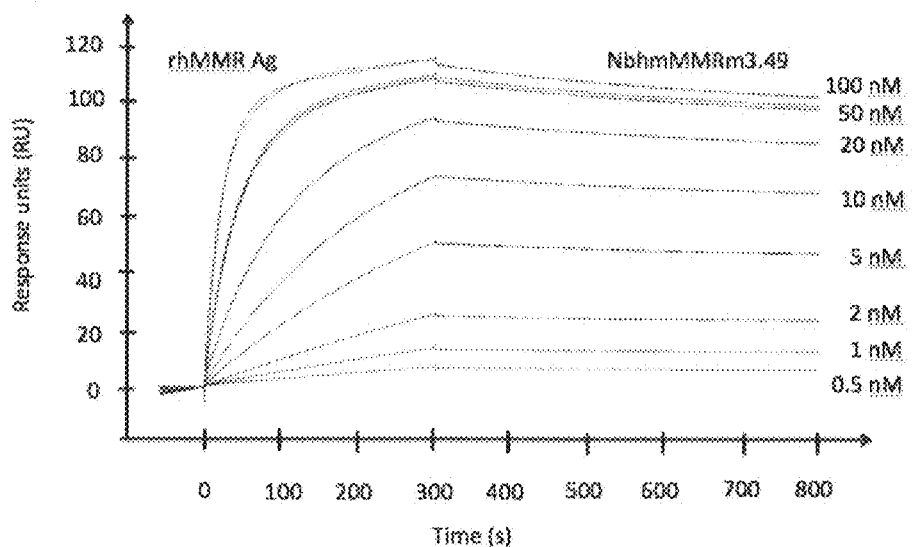
FIG. 7: Surface Plasmon resonance sensograms of NbhmMMRm3.49 binding to recombinant human and mouse MMR. NbhmMMRm3.49 was injected in multiple concentrations at 30 µl/min. over a CM5 sensorchip coated with 3500RU of recombinant human (A) or mouse (B) MMR. The sonograms depict the association and dissociation phase over a period of 800 s.
Figure 7B:
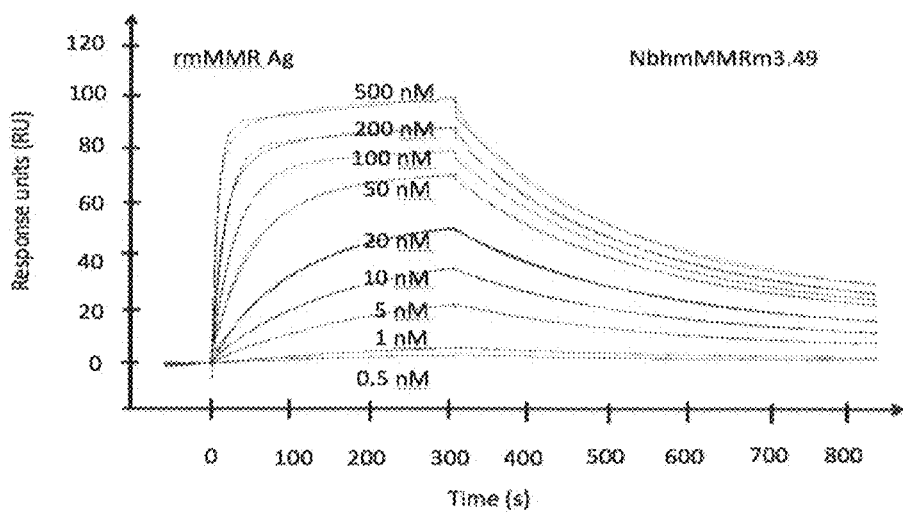

The binding characteristics and affinity of selected Nbs towards the recombinant hMMR and recombinant mMMR antigen was examined in further detail using surface plasmon resonance. A combined sensogram was recorded for each Nb (example for NbhmMMRm3.49 in FIG. 7) and the kinetic and equilibrium parameters (kd, ka and KD) values were calculated (Table 8 and Table 9). Most but not all results on binding to mouse or human rMMR obtained via this SPR analysis are in agreement with the results obtained by PE-ELISA.

Based on the kinetic and equilibrium parameters (kd, ka and KD) values five among the cross-reactive anti-hmMMR Nbs were selected for further analysis (indicated in bold in Table 8 and Table 9). These five Nbs (NbhmMMRm3.1, NbhmMMRm14.4, NbhmMMRm5.38, NbhmMMRm26.70 and NbhmMMRm3.49) displayed rather low dissociation rate constants, which makes them suitable for in vivo imaging. The corresponding KD values for these Nanobodies ranged from 68 nM to 2 nM. It can clearly be seen from the data in Table 8 and 9 that the Nbs have a preferred MMR antigen: NbhmMMRm3.1, NbhmMMRm14.4, NbhmMMRm5.38 and NbhmMMRm3.49 have a higher affinity for the hMMR Ag compared to the mMMR Ag. In contrast, NbhmMMRm26.70 binds better to mMMR Ag as compared to hMMR Ag, even though the first rounds of immunization and panning were performed using the hMMR antigen.

Example 9

Determination of Binding of a Representative Set of Anti-Human or Anti-Human/Mouse MMR Nbs on MMR Expressed on Cells Via Flow Cytometry In order to confirm the binding specificity of the 5 selected Nbs to MMR expressed on cells, flow cytometric analysis was performed.

Figure 8:
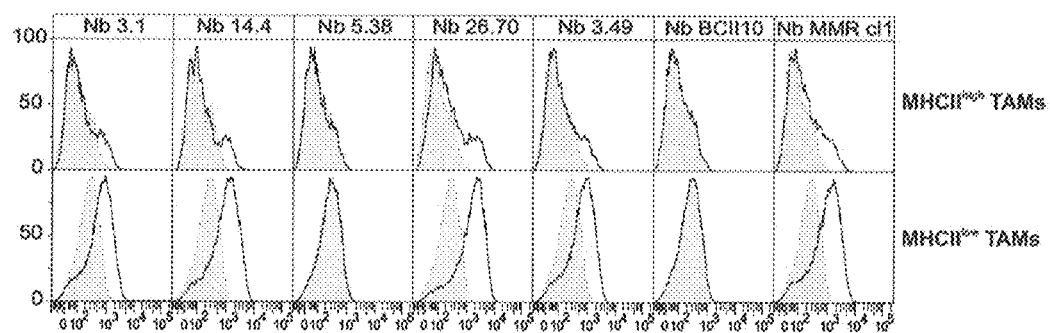
FIG. 8: MMR specific Nbs bind to mouse MMR expressed on ex vivo isolated macrophages. 3LL-R tumors were induced by injecting 3×10$^6$ cancer cells subcutaneously in C57Bl/6 mice. After 15 days of tumor growth, the tumors were isolated and single cell suspensions were prepared to be analyzed by flow cytometry. The CD11b+ Ly6G-tumor associated macrophages (TAM) were further gated on MHCII expression. The histograms depict MMR expression as defined by Nb binding on MHCII$^{low}$ and MHCII$^{high}$ TAMs. Shaded histograms depict binding of the negative control Nb BCII10.

Binding to cell-expressed mouse MMR was determined on tumor associated macrophages derived from a preclinical mouse tumor model, making use of the previously documented finding that TAMs contain molecularly and functionally distinct subsets differing in expression of MMR: MMR is highly expressed on MHC TAMs, whereas MMR expression is lower for MHC II$^{high}$ TAMs (Movahedi et al., 2010). As shown in FIG. 8, clear shifts in fluorescence intensity, comparable to the shift of the anti-mMMR Nb clone 1, could be detected on MHCII$^{low}$ TAMs for NbhMMRm3.1, NbhmMMRm14.4, NbhmMMRm26.70 and NbhMMRm3.49. Remarkably, binding of NbhmMMRm5.38 to TAMs could not be detected.

Figure 9:
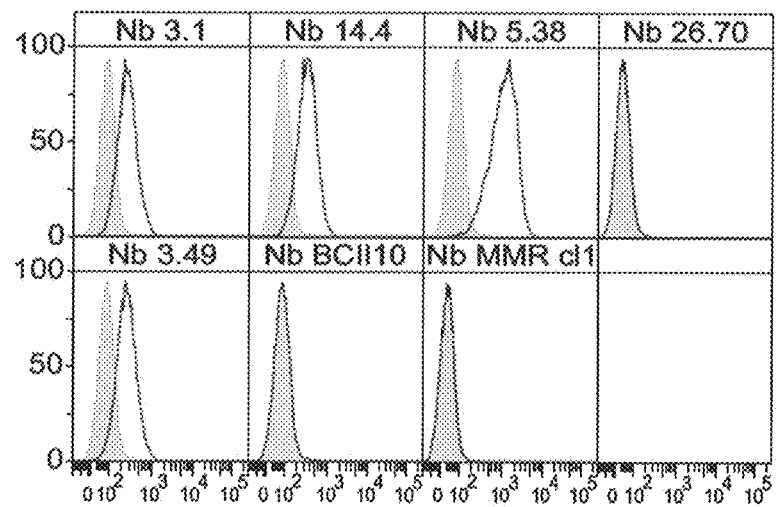
FIG. 9: MMR specific Nbs bind to human MMR expressed on induced dendritic cells. Anti-hMMR Nbs bind to CD11c+ subsets in human iDC single-cell suspensions. Shaded histograms depict binding of the negative control Nb BCII10.

In order to investigate the binding specificity of the selected Nbs to human MMR, human immature monocyte-derived dendritic cells were generated and gated on CD11c$^+$ cells. As shown in FIG. 9, binding of NbhMMRm3.1, NbhmMMRm14.4, NbhmMMRm5.38 and NbhmMMRm3.49 to hMMR expressed on immature dendritic cells was clearly detected, whereas no significant shift in fluorescence intensity could be detected for NbhmMMRm26.70.

Overall, the flow cytometry analysis indicates that NbhmMMRm5.38 binds on cell expressed human MMR, but not mouse MMR. In contrast, NbhmMMRm26.70 has a similar binding pattern to the original anti-mouse MMR clone 1 and binds to mouse but not human MMR. NbhMMRm3.1, NbhmMMRm14.4 and NbhmMMRm3.49 bind to both mouse and human MMR expressed on cells.

Example 10

Tissue Distribution Experiments with Anti-Human Macrophage Mannose Receptor Nanobodies in Naive Mice In a next step, we wished to assess whether selected anti-human MMR Nbs could be used for in vivo targeting of MMR-expressing cells. Since the flow cytometry analysis on human immature dendritic cells had revealed that NbhmMMRm26.70 does not bind to human MMR, it was not analyzed at this time. Since NbhmMMRm3.1 and NbhmMMRm3.49 share the same CDR3 loop, but NbhmMMRm3.49 has a better affinity for recombinant MMR as compared to NbhmMMRm3.1, among those two Nanobodies, NbhmMMRm3.49 was selected for the in vivo targeting. Also NbhmMMRm14.4 and NbhmMMRm5.38 were included in the selection to be used for this example. Since the latter did not bind to mouse MMR according to the flow cytometric analysis, it could be used to exclude aspecific binding and accumulation in tissues.

Figure 10:
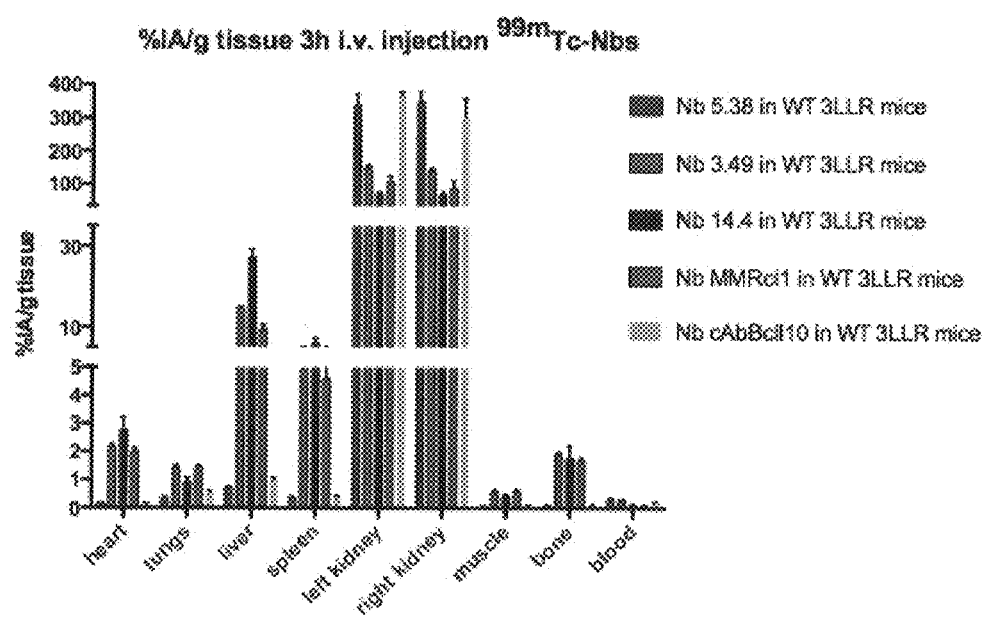
FIG. 10: Tissue distribution experiments of MMR Nbs in WT C57/bl6 mice. Anti-MMR Nbs were labeled with $^{99m}$Tc and injected in the tail vein of C57/bl6 mice (n=3). After 3 hours, the mice were dissected and radioactivity was measured in the major organs. The uptake values for the negative control Nb cAbBcII10 served as a measure for general aspecific Nb distribution.

The selected Nanobodies were labeled with $^{99m}$Tc and injected intravenously in naive C57BL/6 mice. 3 hours post injection, the mice were dissected and radioactivity was measured in the major organs. As shown in FIG. 10, NbhmMMRm14.4 and NbhmMMRm3.49 exhibited similar tissue distribution as the original anti-mouse MMR Nanobody clone 1, with high uptake in organs such as lungs, spleen and liver. In contrast, the negative controls NbhmMMRm5.38 and Nb cAbBcII10 mainly showed high tracer uptake in the kidneys, indicative of renal clearance.

Example 11

Nb MMR Cl1 Aortic Distribution in ApoE–/– Mice

Figure 11:
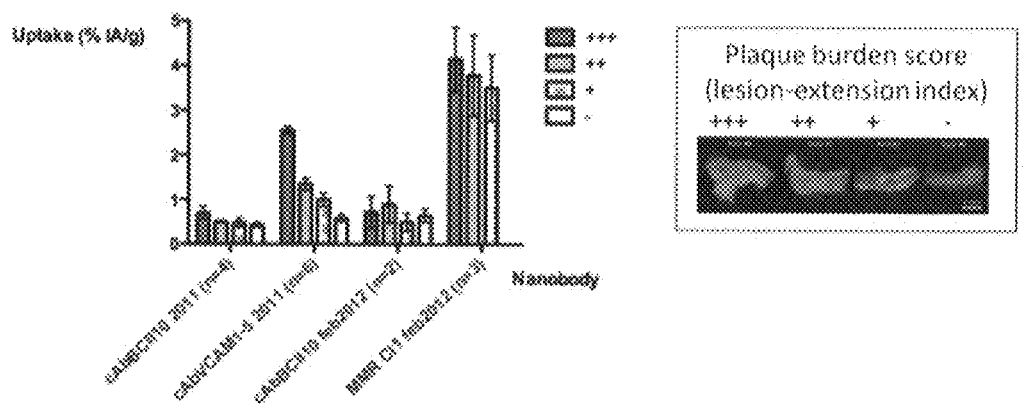
FIG. 11: Nb MMR cl1 aortic distribution in ApoE$^{-/-}$ mice. Uptake of Nb MMR cl1 as compared to negative control Nanobody cAb BCII10 and positive control Nanobody cAb VCAM1-5, in arterial segments from ApoE−/− mice, ranked according to the lesion-extension index. The lesion-extension index was attributed to each segment as shown in the inset: (−) no lesion (control segments), (+) lesion covering up to 50% of the arterial segment length, (++) lesions covering >50% of the arterial segment length, and (+++) lesions extending over the whole segment length.

To perform a first preliminary assessment of the use of anti-MMR Nanobodies for in vivo targeting of atherosclerotic plaques, ApoE–/– mice fed on a "Western diet" were used as a model of atherosclerosis. Anti-MMR Nb clone 1 was labeled with $^{99m}$Tc and injected intravenously in 3 mice. In FIG. 11, uptake of Nb MMR clone 1 in aorta segments ranked according to the lesion-extension index is shown as compared to negative control Nanobody cAb BCII10 and positive control Nanobody cAb VCAM1-5. The signal obtained on plaque-containing aorta sections was higher for the anti-MMR Nanobody than for the anti-VCAM1 Nanobody. Please note that the 3 mice that were tested in this experiment had quite progressed atherosclerotic disease and in fact no lesion-free aorta sections were present in these mice. Therefore, additional experiments will be required to confirm that the signal obtained on the atherosclerotic lesions is higher than the background signal on control aorta sections.

Example 12

In Vivo Targeting with Anti-Macrophage Mannose Receptor Nanobodies in Myocardial-Infarction Prone Watanabe Heritable Hyperlipidemic Rabbits Myocardial-infarction prone Watanabe heritable hyperlipidemic rabbits (WHHLMI rabbits) show hypercholesterolemia due to a deficiency of Low-Density Lipoprotein receptors, a very similar lipoprotein metabolism to humans and a spontaneous development of progressive coronary atherosclerosis and myocardial infarction. They thus represent an ideal animal model for atherosclerosis.

Figure 12:
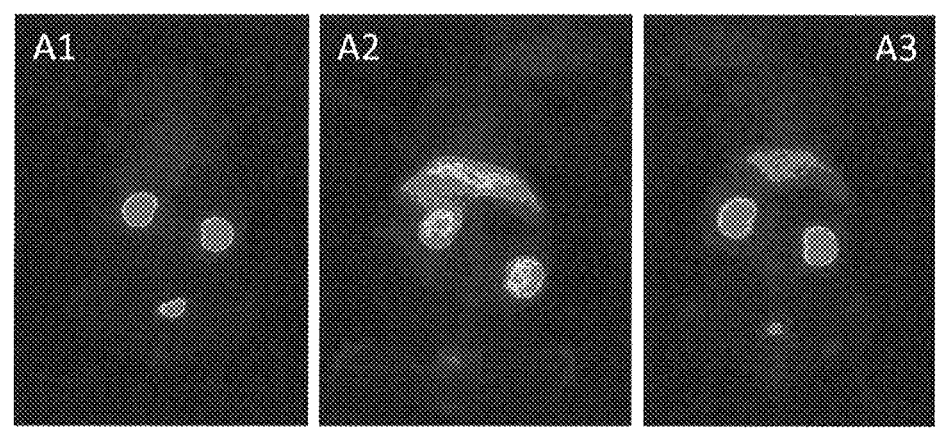
FIG. 12: In vivo crossreactivity of anti-MMR nanobodies in WHHLMI rabbits. Panel A: Planar images at 60 minutes after injection of $^{99m}$Tc labeled Nb MMR cl1 (A1), NbhmMMRm3.49 (A2) and NbhmMMRm14.4 (A3). Panel B: Radioactivity in dissected organs, expressed as percentage of injected activity per organ (B1) or as differential uptake ratio (DUR; % ID/g/kg), calculated as (tissue activity/tissue weight)/(injected activity/animal body weight) (B2).
Figure 12:
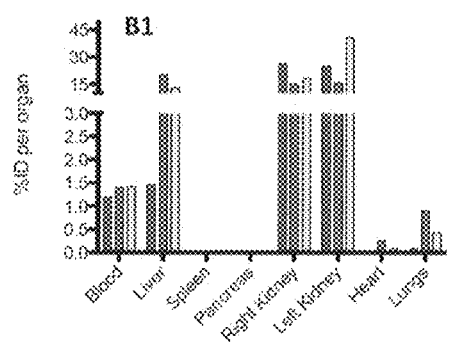
Figure 12:
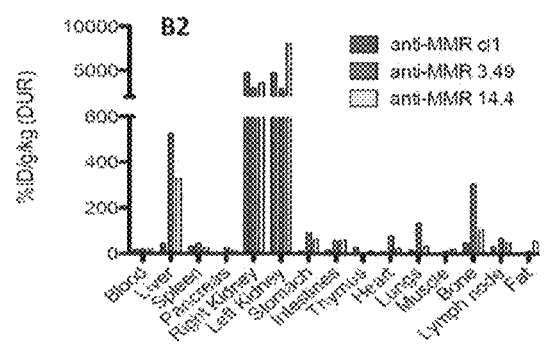

To assess which of the anti-MMR Nanobodies are cross-reactive in rabbits and can thus be used for in vivo imaging experiments in WHHLMI rabbits, an in vivo experiment was performed in which three of the lead anti-MMR nanobodies (MMR Nb cl1, NbhmMMRm3.49 and NbhmMMRm14.4) were labeled with $^{99m}$Tc via tricarbonyl chemistry, as described previously, and injected intravenously in WHHLMI rabbits. All three Nanobodies were cleared via the kidneys and urine. High uptake in liver and bone marrow could also be observed for NbhmMMRm3.49 and NbhmMMRm14.4, while no uptake in these or organs was seen for MMR Nb cl1 (FIG. 12). Thus, it seems NbhmMMRm3.49 and NbhmMMRm14.4 but not MMR Nb cl1 are cross-reactive in rabbits.

The cross-reactive Nanobodies will next be $^{99m}$Tc-labeled and injected in WHHLMI rabbits of 12-20 months old, which have different stages of atherosclerosis development. At 3 hours post-injection, the animals will be euthanized, the aortas will be removed and cut into segments of 1-2 cm long. The segments will be weighted and radioactivity will be counted in a gamma-well counter. For each aorta segment, the plaques will be classified in 4 groups based on the American Heart Association (AHA) recommendations: neo-intimal, atheromatous, fibroatheromatous and collagen-rich lesions. The classification will be obtained after histologic evaluation (HES- and tri-chrome staining). Additional characteristics will be evaluated with immunohistology (expression of MMR, VCAM-1, Lox-1, Macrophage infiltration, lipid infiltration, hemorrhages, calcification . . . ). The radioactive signals will then be correlated with the histological findings to assess the association of the obtained signal for anti-MMR Nanobodies with the stage and vulnerability of the plaques.

Example 13

Anti-MMR Nanobody-Based Immunohistochemistry on Human Clinical Samples of Atherosclerotic Plaques In order to test the relevancy of anti-MMR Nanobodies for targeting of human vulnerable atherosclerotic plaques, immunohistochemistry analysis will be performed on human clinical samples of atherosclerotic plaques. As a preparatory step, the conditions for performing immunohistochemistry using the anti-MMR Nanobodies will be optimized using control MMR positive tissue samples (such as human liver). In particular, the Nanobody clones recognizing human MMR will be subcloned and produced in fusion with a detection tag such as hemagglutinin (HA) for detection by secondary anti-HA reagents. Also, it will be evaluated which of the anti-MMR Nanobody clones are optimal for immunohistochemistry.

Using the optimized reagents, immunohistochemistry analysis will next be performed on human clinical samples of whole-mount carotid endarterectomy specimens and the signals obtained using the anti-MMR Nanobodies will be correlated with the stage and vulnerability of the various plaques.

Example 14

Figure 13:
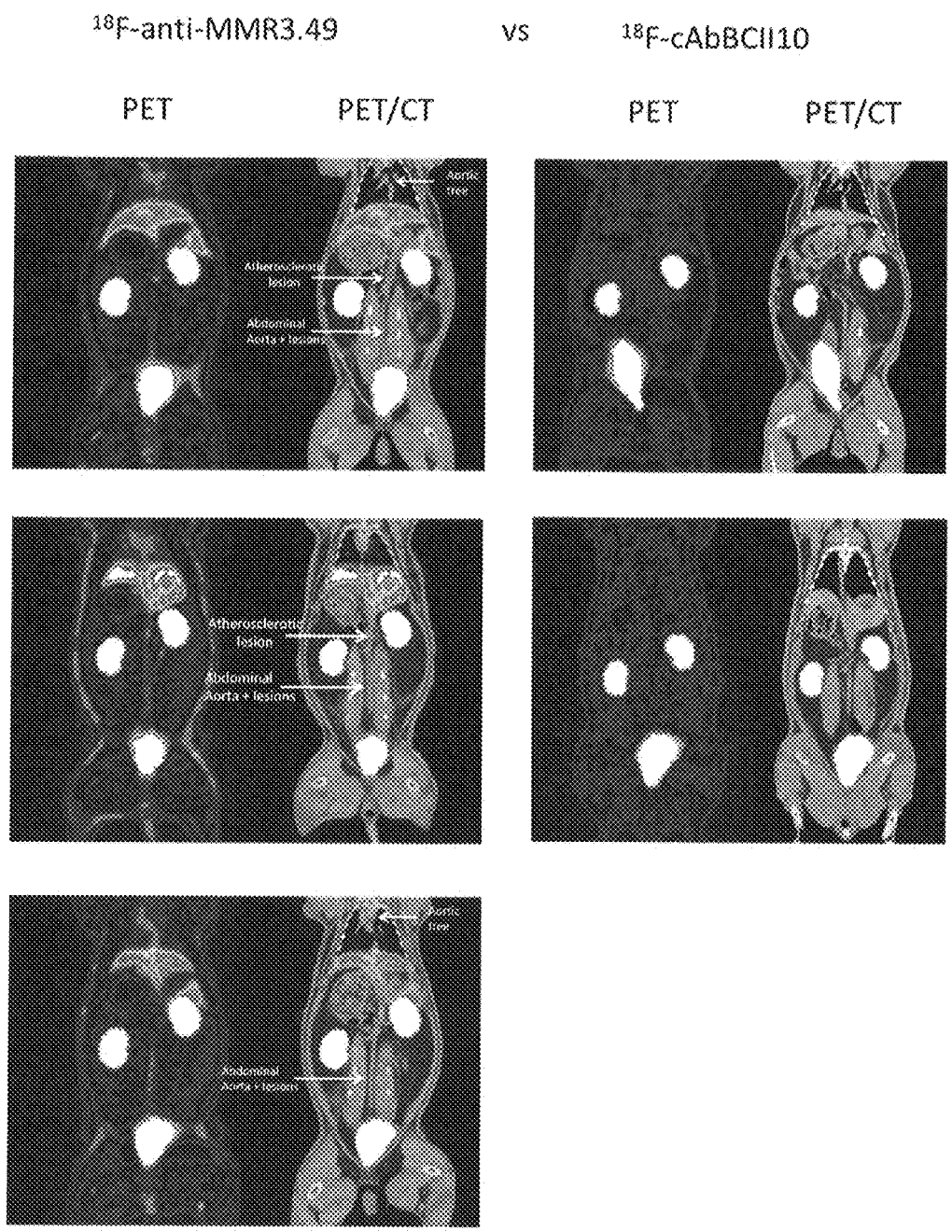
FIG. 13: PET based in vivo imaging with anti-Macrophage Mannose Receptor Nanobodies of atherosclerotic lesions in abdominal aorta of Myocardial-infarction prone Watanabe heritable hyperlipidemic rabbits. PET images and fused PET/CT images are shown for individual rabbits injected with either 18F-labeled anti-MMR nanobody (clone 3.49; n=3; left column) or 18F-labeled control nanobody cAbBCII10 (n=2; right column). Arrows indicate atherosclerotic lesions.
Figure 14:
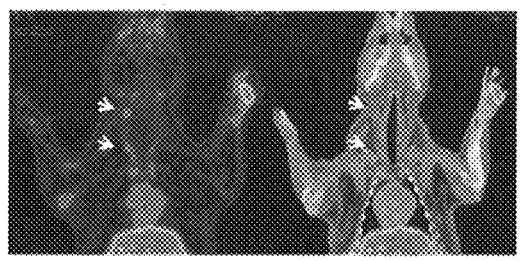
FIG. 14: PET based in vivo imaging with anti-Macrophage Mannose Receptor Nanobodies of atherosclerotic lesions in carotid artery of Myocardial-infarction prone Watanabe heritable hyperlipidemic rabbits. PET images and fused PET/CT images are shown for individual rabbits injected with either 18F-labeled anti-MMR nanobody (clone 3.49; n=3; left column) or 18F-labeled control nanobody cAbBCII10 (n=2; right column). Arrows indicate atherosclerotic lesions.
Figure 14:
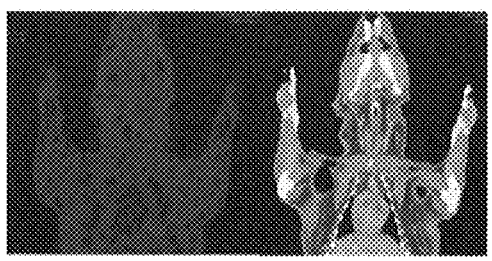
Figure 14:
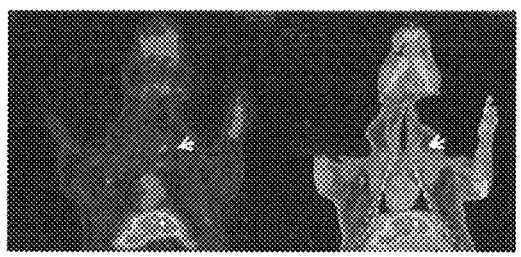
Figure 14:
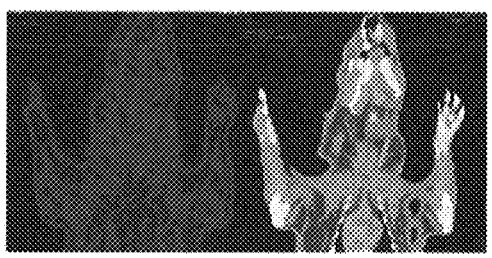
Figure 14:
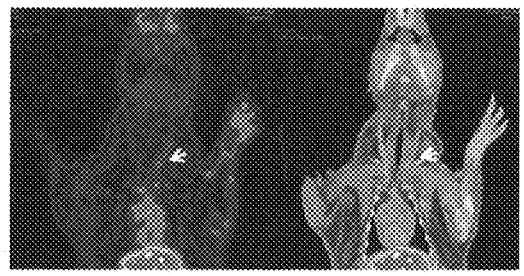

In Vivo Targeting and PET/CT Based In Vivo Imaging with Anti-Macrophage Mannose Receptor Nanobodies in Myocardial-Infarction Prone Watanabe Heritable Hyperlipidemic Rabbits Taking into account the resolution required for optimal in vivo imaging of atherosclerotic lesions, the anti-MMR Nanobody NbhmMMRm3.49 and the control Nanobody cAbBcII10 were 18F labeled for PET imaging. Male WHHLMI rabbits of 13-16 months old were injected with 18F-labeled Nanobodies via marginal ear vein. For the control Nanobody, signals were only detected in kidneys and bladder (FIGS. 13 and 14; right column). Rabbits injected with the anti-MMR nanobody additionally exhibited marked signals in the liver and the skin. Interestingly, atherosclerotic lesions in the abdominal aorta (FIG. 13; left column) and carotid artery (FIG. 14; left column) of rabbits were readily visualized using NbhmMMRm3.49.

Example 15

In Vivo Targeting and PET/CT Based In Vivo Imaging with Anti-Macrophage Mannose Receptor Nanobodies in a Myocardial Ischemia/Reperfusion Injury (IRI) Rat Model Improving the management of acute myocardial ischemia (MI) has led to a decrease in early mortality in Europe. However, ischemic heart diseases remain the most important cause of morbidity and mortality in developed countries. Studies have shown that the inflammatory process after MI might be of interest for prognosing patient outcome, such as evaluating the risk of developing heart remodeling and/or heart failure, and treatment decisions. Therefore, methods for the in vivo assessment of different subsets of immune responses after MI are warranted. Here, the expression profile of M2-inflammation over time was imaged, using radiolabeled Nanobodies (Nbs) targeting the macrophage mannose receptor (MMR, CD206+), in a myocardial ischemia/reperfusion injury (IRI) rat model (see Material and Methods section).

Figure 15:
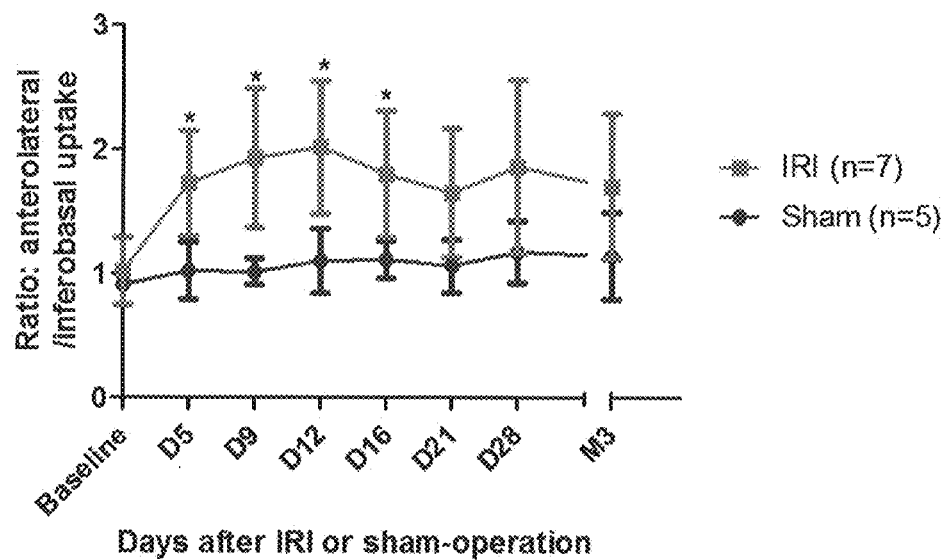
FIG. 15: Longitudinal profile of 99mTc-MMR-Nb uptake after myocardial ischemia/reperfusion injury. Ratio of the in vivo quantified mean uptake of 99mTc-MMR-Nb at the anterolateral segment of myocardium over the mean uptake of 99mTc-MMR-Nb at the inferobasal segment (control region). Repeated measures ANOVA on log-transformed data show a significant difference in mean $^{99m}$Tc-MMR-Nb uptake in the animal group subjected to ischemia/reperfusion injury in comparison to sham operated animals from day 5 until day 16. Error bars show the standard deviation.
Figure 16:
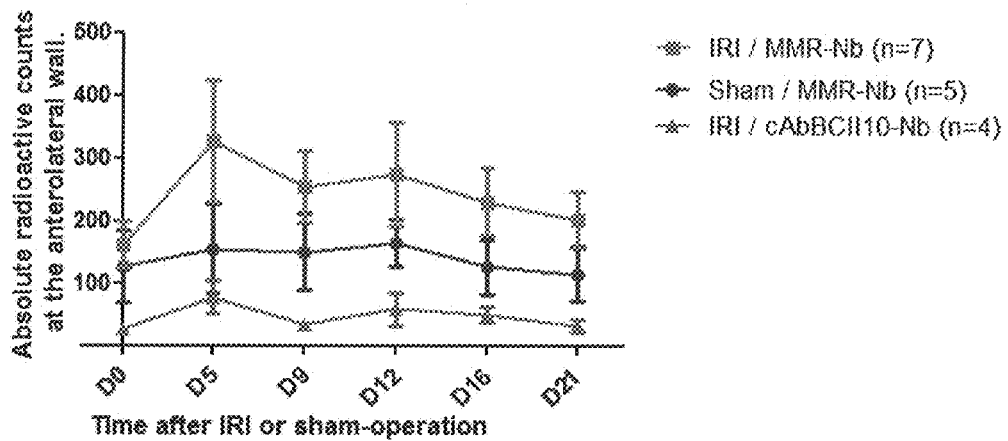
FIG. 16: Absolute in vivo quantification of 99mTc-MMR-Nb uptake on different time points after myocardial ischemia/reperfusion injury. Data are presented as group mean±standard deviation. The red line (block) denotes the absolute uptake of the $^{99m}$Tc-MMR-Nb at the site of infarction (anterolateral wall), the blue depicts (dot) retention of the $^{99m}$Tc-MMR-Nb at the anterolateral wall in sham operated animals and the green line (triangle) represents the retention profile of a control nanobody (cAbBCII10-Nb) at the site of infarction in animals subjected to IRI.
Figure 17:
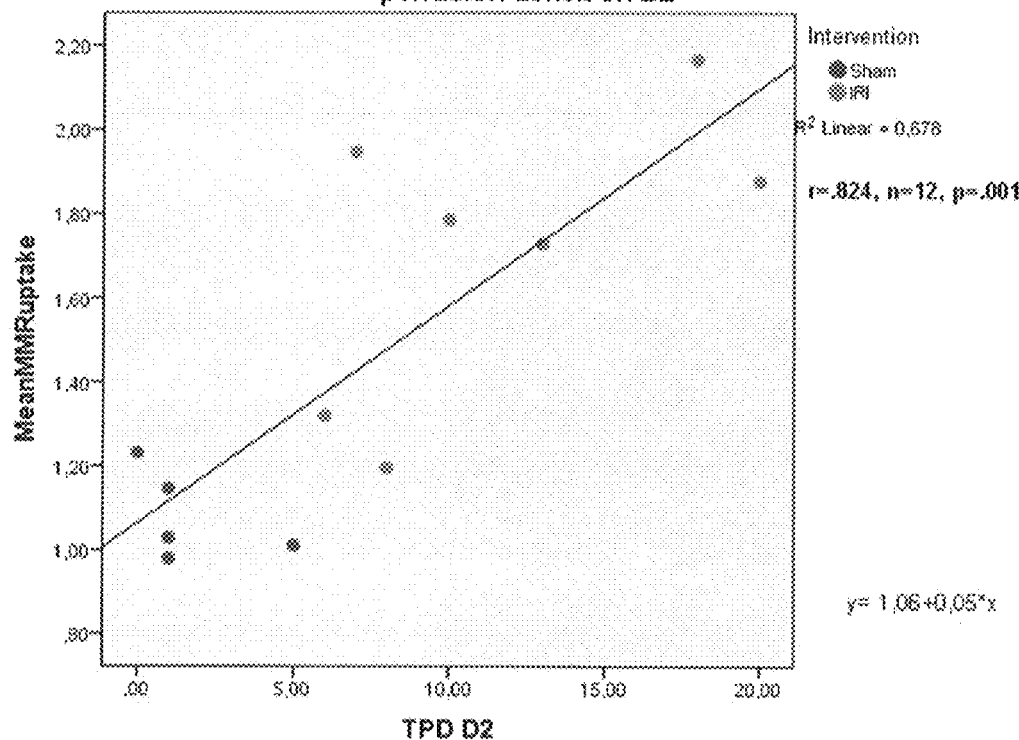
FIG. 17: Correlation between the mean of ratios of anti-MMR-Nb uptake and total perfusion deficit on D2. The means of the $^{99m}$Tc-MMR-Nb ratios of all available time points (MeanMMRuptake) are plotted against the corresponding total perfusion deficit (TPD D2), assessed by a $^{99m}$Tc Tetrofosmin scan on day 2. The blue dots represent sham-operated rats whereas the red dots depict the rats subjected to IRI. The least square regression line and its equation are also shown.

Myocardial IRI was induced by ligation of the left anterior descending coronary artery during 60 minutes followed by loosening of the suture in 17 Wistar rats. Seven animals were sham operated. The infarct size was assessed by a $^{99m}$Tc-Tetrofosmin scan on day 2. Pinhole-SPECT/μCT acquisitions of $^{99m}$Tc-MMR-Nb were taken at baseline, at day (D) 5, 9, 12, 16, 21, 28 and 3 months after IRI. Four animals died during the procedure and 4 animals died shortly thereafter. Infarct zone (IZ), expressed as total perfusion deficit (TPD), was 11.72±5.50. The ratio of the $^{99m}$Tc-MMR-Nb uptake in IRI and sham-operated rats was significantly different over time (F(6.48)=2.57, p=0.03) (FIG. 15). There was a significant difference on D5, D9, D12 and D16 (p<0.05) between sham and IRI, but no difference was observed at baseline and after D16 (FIG. 16). A significant correlation was also present between the in vivo quantified mean ratio of $^{99m}$Tc-MMR-Nb uptake and TPD (r=0.824, n=12, p<0.001) (FIG. 17).

Figure 18A:
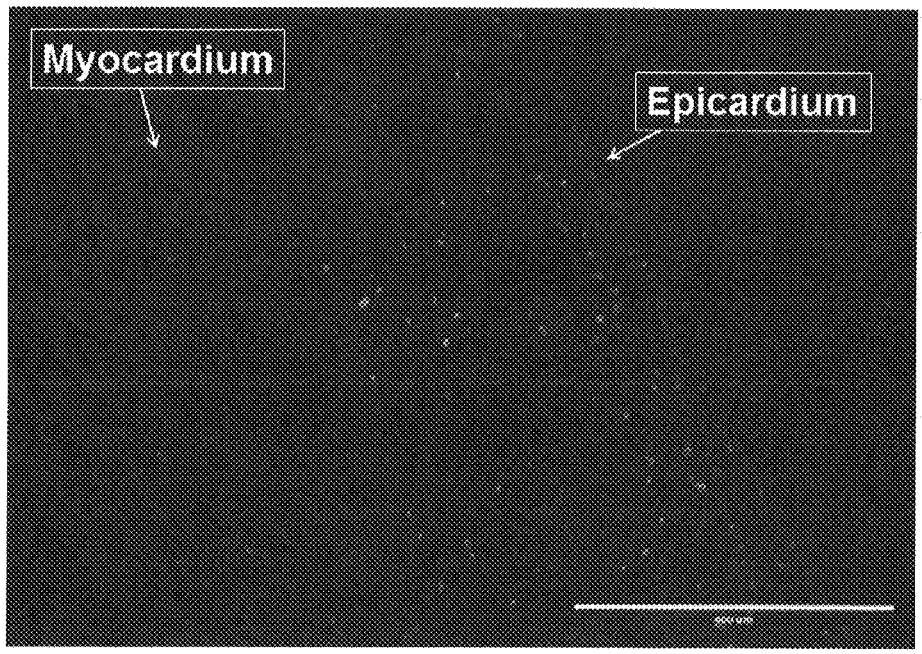
FIG. 18: Ex vivo immunofluorescence staining on cardiac cryo-sections after myocardial ischemia/reperfusion injury. A. Double immunofluorescence staining of CD206 (MMR, red) and CD68 (macrophage lineage marker, green) on cryo-sectioned cardiac tissue. The animal was sacrificed 12 days after the induction of IRI. The slice was obtained in the vicinity of the infarcted area. B. The upper panel shows double immunofluorescence staining for MMR (CD206; red) and CD68 (green). The slice is taken at the border of infarction 120 days after the induction of IRI, on guidance of the corresponding $^{99m}$Tc-MMR-Nb acquisition. C. Transverse, coronal and sagittal fused pinhole SPECT/microCT images of the same animal. The $^{99m}$Tc-MMR-Nb acquisition is shown using NIH color table. $^{99m}$Tc-Tetrofosmin uptake in the myocardium is shown as deep green. The absence of the uptake of $^{99m}$Tc-Tetrofosmin is suggestive for myocardial infarction and allows correct interpretation of the localization of $^{99m}$Tc-MMR-Nb retention in regard to the injured site (white arrow).
Figure 18B:
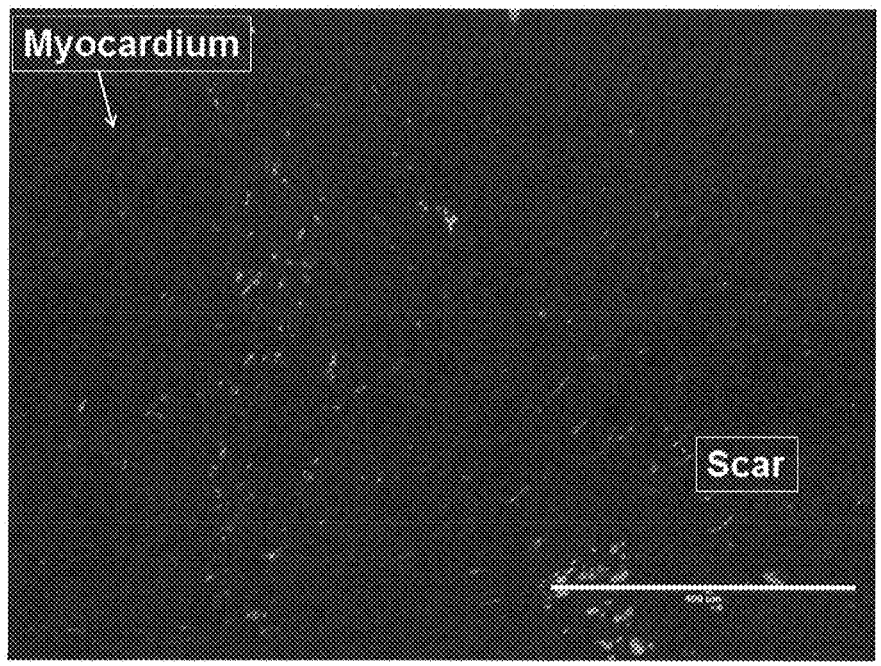
Figure 18C:
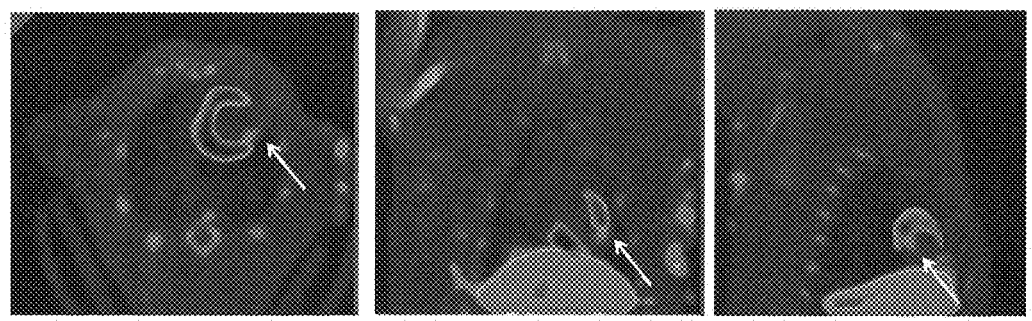

Ex vivo immunofluorescence staining on cardiac cryosections demonstrated the presence of MMR in the IZ and the surrounding pericardium, this was in accordance with the localization of in vivo uptake. Furthermore, MMR co-localized with CD68 on double immunofluorescence staining (FIGS. 18 and 19).

TABLE 1

Anti- mouse CD206 (MMR) Nanobodies (anti-MMR Nanobody clone 1 and 3): monovalent en bivalent constructs and Nanobodies.

| | |
|---|---|
| DNA seq + His tag (clone 1) SEQ ID NO: 134 | CAGGTGCAGCTGCAGGAGTCTGGAGGAGGCTTGGTGCA GCCTGGGGGGTCTCTGAGACTCTCCTGTGCAGCCTCTGG AAACATCTTCAGTATCAATGCCATCGGCTGGTACCGCC AGGCTCCAGGGAAGCAGCGCGAGTTGGTCGCAACTATT ACTCTTAGTGGTAGCACAAACTATGCAGACTCCGTGAA GGGCCGATTCTCCATCTCCAGAGACAACGCCAAGAACA CGGTGTATCTGCAAATGAACAGCCTGAAACCTGAGGAC ACGGCCGTCTATTACTGTAATGCTAACACCTATAGCGAC TCTGACGTTTATGGCTACTGGGGCCAGGGGACCCAGGT CACCGTCTCCTCACACCACCATCACCATCAC |
| DNA seq - His tag (clone 1) | CAGGTGCAGCTGCAGGAGTCTGGAGGAGGCTTGGTGCA GCCTGGGGGGTCTCTGAGACTCTCCTGTGCAGCCTCTGG |

TABLE 1-continued

Anti- mouse CD206 (MMR) Nanobodies (anti-MMR Nanobody clone 1 and 3): monovalent en bivalent constructs and Nanobodies.

| | |
|---|---|
| SEQ ID NO: 135 | AAACATCTTCAGTATCAATGCCATCGGCTGGTACCGCC AGGCTCCAGGGAAGCAGCGCGAGTTGGTCGCAACTATT ACTCTTAGTGGTAGCACAAACTATGCAGACTCCGTGAA GGGCCGATTCTCCATCTCCAGAGACAACGCCAAGAACA CGGTGTATCTGCAAATGAACAGCCTGAAACCTGAGGAC ACGGCCGTCTATTACTGTAATGCTAACACCTATAGCGAC TCTGACGTTTATGGCTACTGGGGCCAGGGGACCCAGGT CACCGTCTCCTCA |
| Amino acid seq + His tag (clone 1) SEQ ID NO: 1 | QVQLQESGGGLVQPGGSLRLSCAASGNIFSINAIGWYRQA PGKQRELVATITLSGSTNYADSVKGRFSISRDNAKNTVYL QMNSLKPEDTAVYYCNANTYSDSDVYGYWGQGTQVTVS SHHHHHH |
| Amino acid seq - His tag (clone 1) SEQ ID NO: 2 | QVQLQESGGGLVQPGGSLRLSCAASGNIFSINAIGWYRQA PGKQRELVATITLSGSTNYADSVKGRFSISRDNAKNTVYL QMNSLKPEDTAVYYCNANTYSDSDVYGYWGQGTQVTVS S |
| DNA seq + His tag (clone 3) SEQ ID NO: 136 | CAGGTGCAGCTGCAGGAGTCTGGAGGAGGATTGGTGCA GGCTGGGGGCTCTCTGAGACTCTCCTGTGCAGCCTCTGG ACGCACCTTCAGTAGAGATGCCATGGGCTGGTTCCGCC AGGCTCCAGGGAAGGAGCGTGAGTTTGTAGCAGGTATT AGCTGGAGTGGTGGTAGCACATACTATGCAGACTCCGT GAAGGGCCGATTCACCATCTCCAGGGACGGCGCCAAGA ACACGGTAAATCTGCAAATGAACAGCCTGAAACCTGAG GACACGGCCGTTTATTACTGTGCAGCATCGTCGATTTAT GGGAGTGCGGTAGTAGATGGGCTGTATGACTACTGGGG CCAGGGGACCCAGGTCACCGTCTCCTCACACCACCATC ACCATCAC |
| DNA seq - His tag (clone 3) SEQ ID NO: 137 | CAGGTGCAGCTGCAGGAGTCTGGAGGAGGATTGGTGCA GGCTGGGGGCTCTCTGAGACTCTCCTGTGCAGCCTCTGG ACGCACCTTCAGTAGAGATGCCATGGGCTGGTTCCGCC AGGCTCCAGGGAAGGAGCGTGAGTTTGTAGCAGGTATT AGCTGGAGTGGTGGTAGCACATACTATGCAGACTCCGT GAAGGGCCGATTCACCATCTCCAGGGACGGCGCCAAGA ACACGGTAAATCTGCAAATGAACAGCCTGAAACCTGAG GACACGGCCGTTTATTACTGTGCAGCATCGTCGATTTAT GGGAGTGCGGTAGTAGATGGGCTGTATGACTACTGGGG CCAGGGGACCCAGGTCACCGTCTCCTCA |
| Amino acid seq + His tag (clone 3) SEQ ID NO: 3 | QVQLQESGGGLVQAGGSLRLSCAASGRTFSRDAMGWFRQ APGKEREFVAGISWSGGSTYYADSVKGRFTISRDAKNTV NLQMNSLKPEDTAVYYCAASSIYGSAVVDGLYDYWGQG TQVTVSSHHHHHH |
| Amino acid seq - His tag (clone 3) SEQ ID NO: 4 | QVQLQESGGGLVQAGGSLRLSCAASGRTFSRDAMGWFRQ APGKEREFVAGISWSGGSTYYADSVKGRFTISRDAKNTV NLQMNSLKPEDTAVYYCAASSIYGSAVVDGLYDYWGQG TQVTVSS |
| DNA seq + His tag (MMR biv IgA) SEQ ID NO: 138 | CAGGTGCAGCTTCAGGAGTCTGGAGGAGGCTTGGTGCA GCCTGGGGGGTCTCTGAGACTCTCCTGTGCAGCCTCTGG AAACATCTTCAGTATCAATGCCATCGGCTGGTACCGCC AGGCTCCAGGGAAGCAGCGCGAGTTGGTCGCAACTATT ACTCTTAGTGGTAGCACAAACTATGCAGACTCCGTGAA GGGCCGATTCTCCATCTCCAGAGACAACGCCAAGAACA CGGTGTATCTGCAAATGAACAGCCTGAAACCTGAGGAC ACGGCCGTCTATTACTGTAATGCTAACACCTATAGCGAC TCTGACGTTTATGGCTACTGGGGCCAGGGGACCCAGGT CACCGTCTCCTCAAGCCCATCTACACCTCCCACACCATC ACCATCCACACCACCGGCAAGTCAGGTGCAGCTGCAGG AGTCTGGAGGAGGCTTGGTGCAGCCTGGGGGGTCTCTG AGACTCTCCTGTGCAGCCTCTGGAAACATCTTCAGTATC AATGCCATCGGCTGGTACCGCCAGGCTCCAGGGAAGCA GCGCGAGTTGGTCGCAACTATTACTCTTAGTGGTAGCAC AAACTATGCAGACTCCGTGAAGGGCCGATTCTCCATCT CCAGAGACAACGCCAAGAACACGGTGTATCTGCAAATG AACAGCCTGAAACCTGAGGACACGGCCGTCTATTACTG TAATGCTAACACCTATAGCGACTCTGACGTTTATGGCTA CTGGGGCCAGGGGACCCAGGTCACCGTCTCCTCACACC ACCATCACCATCAC |

TABLE 1-continued

Anti- mouse CD206 (MMR) Nanobodies (anti-MMR Nanobody clone 1 and 3): monovalent en bivalent constructs and Nanobodies.

| | |
|---|---|
| Amino acid seq + His tag (MMR biv IgA) SEQ ID NO: 5 | QVQLQESGGGLVQPGGSLRLSCAASGNIFSINAIGWYRQA PGKQRELVATITLSGSTNYADSVKGRFSISRDNAKNTVYL QMNSLKPEDTAVYYCNANTYSDSDVYGYWGQGTQVTVS SSPSTPPTPSPSTPPASQVQLQESGGGLVQPGGSLRLSCAAS GNIFSINAIGWYRQAPGKQRELVATITLSGSTNYADSVKGR FSISRDNAKNTVYLQMNSLKPEDTAVYYCNANTYSDSDV YGYWGQGTQVTVSSHHHHHH |
| DNA seq + His tag (MMR biv (Gly4Ser)3) SEQ ID NO: 139 | CAGGTGCAGCTTCAGGAGTCTGGAGGAGGCTTGGTGCA GCCTGGGGGGTCTCTGAGACTCTCCTGTGCAGCCTCTGG AAACATCTTCAGTATCAATGCCATCGGCTGGTACCGCC AGGCTCCAGGGAAGCAGCGCGAGTTGGTCGCAACTATT ACTCTTAGTGGTAGCACAAACTATGCAGACTCCGTGAA GGGCCGATTCTCCATCTCCAGAGACAACGCCAAGAACA CGGTGTATCTGCAAATGAACAGCCTGAAACCTGAGGAC ACGGCCGTCTATTACTGTAATGCTAACACCTATAGCGAC TCTGACGTTTATGGCTACTGGGGCCAGGGGACCCAGGT CACCGTCTCCTCAGGCGGAGGCGGTAGTGGCGGAGGTG GATCTGGAGGCGGCGGTAGTCAGGTGCAGCTGCAGGAG TCTGGAGGAGGCTTGGTGCAGCCTGGGGGGTCTCTGAG ACTCTCCTGTGCAGCCTCTGGAAACATCTTCAGTATCAA TGCCATCGGCTGGTACCGCCAGGCTCCAGGGAAGCAGC GCGAGTTGGTCGCAACTATTACTCTTAGTGGTAGCACA AACTATGCAGACTCCGTGAAGGGCCGATTCTCCATCTCC AGAGACAACGCCAAGAACACGGTGTATCTGCAAATGAA CAGCCTGAAACCTGAGGACACGGCCGTCTATTACTGTA ATGCTAACACCTATAGCGACTCTGACGTTTATGGCTACT GGGGCCAGGGGACCCAGGTCACCGTCTCCTCACACCAC CATCACCATCAC |
| Amino acid seq + His tag (MMR biv (Gly4Ser)3) SEQ ID NO: 6 | QVQLQESGGGLVQPGGSLRLSCAASGNIFSINAIGWYRQA PGKQRELVATITLSGSTNYADSVKGRFSISRDNAKNTVYL QMNSLKPEDTAVYYCNANTYSDSDVYGYWGQGTQVTVS SGGGGSGGGGSGGGGSQVQLQESGGGLVQPGGSLRLSCA ASGNIFSINAIGWYRQAPGKQRELVATITLSGSTNYADSVK GRFSISRDNAKNTVYLQMNSLKPEDTAVYYCNANTYSDS DVYGYWGQGTQVTVSSHHHHHH |
| DNA seq + His tag (MMR biv g2c) SEQ ID NO: 140 | CAGGTGCAGCTTCAGGAGTCTGGAGGAGGCTTGGTGCA GCCTGGGGGGTCTCTGAGACTCTCCTGTGCAGCCTCTGG AAACATCTTCAGTATCAATGCCATCGGCTGGTACCGCC AGGCTCCAGGGAAGCAGCGCGAGTTGGTCGCAACTATT ACTCTTAGTGGTAGCACAAACTATGCAGACTCCGTGAA GGGCCGATTCTCCATCTCCAGAGACAACGCCAAGAACA CGGTGTATCTGCAAATGAACAGCCTGAAACCTGAGGAC ACGGCCGTCTATTACTGTAATGCTAACACCTATAGCGAC TCTGACGTTTATGGCTACTGGGGCCAGGGGACCCAGGT CACCGTCTCCTCAGCGCACCACAGCGAAGACCCCAGCT CCAAAGCTCCCAAAGCTCCAATGGCACAGGTGCAGCTG CAGGAGTCTGGAGGAGGCTTGGTGCAGCCTGGGGGGTC TCTGAGACTCTCCTGTGCAGCCTCTGGAAACATCTTCAG TATCAATGCCATCGGCTGGTACCGCCAGGCTCCAGGGA AGCAGCGCGAGTTGGTCGCAACTATTACTCTTAGTGGT AGCACAAACTATGCAGACTCCGTGAAGGGCCGATTCTC CATCTCCAGAGACAACGCCAAGAACACGGTGTATCTGC AAATGAACAGCCTGAAACCTGAGGACACGGCCGTCTAT TACTGTAATGCTAACACCTATAGCGACTCTGACGTTTAT GGCTACTGGGGCCAGGGGACCCAGGTCACCGTCTCCTC ACACCACCATCACCATCAC |
| Aminoacid seq + His tag (MMR biv g2c) SEQ ID NO: 7 | QVQLQESGGGLVQPGGSLRLSCAASGNIFSINAIGWYRQA PGKQRELVATITLSGSTNYADSVKGRFSISRDNAKNTVYL QMNSLKPEDTAVYYCNANTYSDSDVYGYWGQGTQVTVS SAHHSEDPSSKAPKAPMAQVQLQESGGGLVQPGGSLRLSC AASGNIFSINAIGWYRQAPGKQRELVATITLSGSTNYADSV KGRFSISRDNAKNTVYLQMNSLKPEDTAVYYCNANTYSD SDVYGYWGQGTQVTVSSHHHHHH |

TABLE 2

SPR kinetic and equilibrium parameters for anti-MMR Nanobodies and bivalent Nanobody 1 derivatives.

| Sample | $k_a$ | SE ($k_a$) | $k_d$ | SE ($k_d$) | $K_D$ | Chi$^2$ |
|---|---|---|---|---|---|---|
| Anti-MMR Nb1 | 5.76E+05 | 1.4E+3 | 0.01331 | 2.1E-5 | 2.31E-08 | 0.558 |
| Anti-MMR Nb3 | 9.73E+04 | 1.6E+2 | 0.01859 | 2.2E-5 | 1.91E-07 | 0.190 |
| biv MMR linker 1 GS | 1.04E+06 | 4.9E+3 | 0.004404 | 1.4E-5 | 4.22E-09 | 3.56 |
| biv MMR linker 2 g2c | 1.02E+06 | 4.8E+3 | 0.004107 | 1.4E-5 | 4.04E-09 | 2.50 |
| biv MMR linker 3 IgA | 9.13E+05 | 1.5E+4 | 0.004285 | 5.3E-5 | 4.69E-09 | 2.25 |

Nb: Nanobody;
biv: bivalent;
GS: (Gly$_4$Ser)$_3$ linker;
g2c: llama IgG2 hinge linker;
IgA: human IgA hinge linker;
SE: standard error.

TABLE 3

Uptake values of $^{99m}$Tc-labeled anti-MMR Nb clone 1 in naive and MMR$^{-/-}$ mice based on Pinhole SPECT/micro-CT at 1 hour post injection. Tracer uptake is expressed as percentage injected activity per gram cubic centimeter (% IA/cm$^3$).

| Organs/Tissues | MMR Nb in WT (% IA/cm$^3$) | MMR Nb in MMR$^{-/-}$ (% IA/cm$^3$) |
|---|---|---|
| Heart | 2.04 ± 0.21 | 1.13 ± 0.12 |
| Lungs | 5.96 ± 0.16 | 9.06 ± 2.43 |
| Liver | 18.66 ± 0.87 | 0.91 ± 0.16 |
| Spleen | 6.17 ± 0.31 | 0.34 ± 0.21 |
| Kidney Left | 80.98 ± 1.65 | 100.58 ± 0.4 |
| Kidney Right | 81.65 ± 2.32 | 102.82 ± 6.17 |
| Muscle | 1.74 ± 0.50 | 0.39 ± 0.22 |
| Bone | 5.02 ± 0.01 | 0.46 ± 0.02 |

TABLE 4

Uptake values of $^{99m}$Tc-labeled bivalent anti-MMR Nb constructs (with (G$_4$S)$_3$, llama IgG2 hinge or human IgA hinge linkers), monovalent anti-MMR Nb clone 1, and control cAbBCII10 Nb in naive and MMR$^{-/-}$ mice based on Pinhole SPECT/micro-CT at 1 hour post injection. Tracer uptake is expressed as percentage injected activity per gram cubic centimeter (% IA/cm$^3$).

| Organs-Tissues | (G4S)3 WT (% IA/cm$^3$) | (G4S)3 MMR-/- (% IA/cm$^3$) | Llama IgG2c WT (% IA/cm$^3$) | Llama IgG2c MMR-/- (% IA/cm$^3$) |
|---|---|---|---|---|
| Heart | 1.549 ± 0.057 | 0.541 ± 0.013 | 1.416 ± 0.147 | 0.440 ± 0.070 |
| Lungs | 1.053 ± 0.082 | 1.246 ± 0.038 | 0.987 ± 0.167 | 1.271 ± 0.130 |
| Liver | 20.857 ± 0.215 | 0.930 ± 0.081 | 20.491 ± 0.578 | 1.658 ± 0.077 |
| Spleen | 14.018 ± 1.669 | 0.634 ± 0.042 | 13.618 ± 1.497 | 1.347 ± 0.300 |
| Kidney Left | 26.381 ± 2.054 | 225.129 ± 13.936 | 24.257 ± 1.129 | 193.162 ± 8.114 |
| Kidney Right | 26.074 ± 2.227 | 212.682 ± 6.308 | 24.599 ± 2.053 | 202.343 ± 0.779 |
| Muscle | 0.251 ± 0.034 | 0.224 ± 0.010 | 0.158 ± 0.023 | 0.216 ± 0.015 |
| Bone | 1.466 ± 0.062 | 0.282 ± 0.016 | 1.041 ± 0.114 | 0.254 ± 0.030 |

| Organs-Tissues | Human IgA WT (% IA/cm$^3$) | Human IgA MMR-/- (% IA/cm$^3$) | MMR Nb WT (% IA/cm$^3$) | cAbBCII10 WT (% IA/cm$^3$) |
|---|---|---|---|---|
| Heart | 1.395 ± 0.083 | 0.505 ± 0.057 | 2.793 ± 0.043 | 0.693 ± 0.128 |
| Lungs | 0.936 ± 0.086 | 1.169 ± 0.161 | 2.543 ± 0.417 | 1.837 ± 0.271 |
| Liver | 21.571 ± 0.435 | 1.176 ± 0.044 | 13.670 ± 0.741 | 2.637 ± 0.203 |
| Spleen | 13.805 ± 1.353 | 0.477 ± 0.007 | 13.070 ± 0.251 | 0.933 ± 0.113 |
| Kidney Left | 26.728 ± 3.014 | 210.760 ± 14.414 | 160.443 ± 13.153 | 415.643 ± 15.162 |
| Kidney Right | 24.947 ± 2.463 | 214.144 ± 11.751 | 159.003 ± 13.700 | 408.597 ± 22.588 |
| Muscle | 0.212 ± 0.045 | 0.205 ± 0.004 | ND | ND |
| Bone | 1.089 ± 0.138 | 0.263 ± 0.022 | ND | ND |

TABLE 5

Anti-human MMR Nbs selected after ELISA on human MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 170). CDR1 (underlined), CDR2 (*italics*), and CDR3 (bold) domains are also indicated, and are listed separately in Table 10.

| Name | SEQ ID NO: | Sequence |
|---|---|---|
| NbhMMRm1.33 | 8 | QVQLQESGGGLVQPGGSLRLSCAASG<u>FTLDNYTVA</u>WFRQAPGKEREGVS*CISSSGGS*TNYADSVKGRFTISRDNSKKSVYLQMNSLKPEDTAIYTCAAERAPPYYSGYYFFDSTCVAASYDYWGQGTQVTVSS |
| NbhMMRm10.19 | 9 | QVQLQESGGGLVQPGGSLKLSCAASG<u>SIFSIKTMG</u>WYRQAPGKQRELVAA*ITSGGS*TNYADSVKGRFTISRDNAKNTVYLQMNSLKPEDTAVYYCNADGVVAWDQPYDNYWGQGTQVTVSS |
| NbhMMRm23.30 | 10 | QVQLQESGGGLVQAGDSLSISCAASG<u>DTFNHYSWG</u>WFRQAPGKAREFVA*AISWNGGSK*YADSVKGRFAISRDIAKNTVSLQMNSLEPEDTAVYYCAADRRPYNDWWDDWSWWVYWGQGTQVTVSS |
| NbhMMRm2.15 | 11 | QVQLQESGGGLVQPGESLRLSCKLSG<u>FTLDYYDIG</u>WFRQAPGKEREGVS*CISSIGGS*ANYADSVKGRFTISRDNVKNTVYLQMNSLKPEDTAIYYCAAEAQTPYNDGDCTRASYDYWGQGIQVTVSS |
| NbhMMRm3.1 | 12 | QVQLQESGGGLVQPGGSLRLSCAASG<u>FTLDYYAIG</u>WFRQAPGKEREGIS*CISYKGGS*TTYADSVKGRFTISKDNAKNTAYLQMNNLKPEDTGIYYCAAGFVCYNYDYWGPGTQVTVSS |
| NbhMMRm5.38 | 13 | QVQLQESGGGLVQAGGSLRLSCAASG<u>FTDDDYDIG</u>WFRQAPGKEREGVS*CISSSDGS*TYYADSVKGRFTISSDNAKNTVYLQMNSLKPEDTAVYYCAADFFRWDSGSYYVRGCRHATYDYWGQGTQVTVSS |
| NbhMMRm12.6 | 14 | QVQLQESGGGLVQPGGSLRLSCVVSG<u>SFLSINHMG</u>WYRQVSGEQRELVAA*ITSGGS*TNYADSVKGRFTISRDSAKNTVYLQMNSLKPEDTAVYYCNADALTMLPPFDFWGQGTQVTVSS |
| NbhMMRm11.5 | 15 | QVQLQESGGGLVQPGGSLMLSCAASG<u>NIFTINRMG</u>WYRQAPGKQRELVA*AITSGGNT*NYADSVKGRFTISRDNAKNTVYLQMNSLKPEDTAVYYCNAAIVTMTSPYSDYWGQGTQVTVSS |
| NbhMMRm15.43 | 16 | QVQLQESGGTLVQPGGSLRLSCAASG<u>STFSINNMG</u>WYRQAPGKQRELVA*GITGGNT*HYADSVKGRFTISRDNAKNIMYLQMNGLKPEDTAVYYCNANWGAYWGQGTQVTVSS |
| NbhMMRm16.95 | 17 | QVQLQESGGGLVQPGGSLGLSCAASG<u>RIASISAMG</u>WYRQAPGKQRELVAA*ITGSGRT*NYADSVKGRFTISRDNAKNTVYLQMNSLKPEDTAVYYCNLLMVDYGLGLGTDYWGQGTQVTVSS |
| NbhMMRm4.83 | 18 | QVQLQESGGGLVQPGGSLRLSCAASG<u>PGFKLDYYAIA</u>WFRQAPGKEREGVS*CIGGSGSGLT*TYVENSVKDRFTISRDNAQNTVYLHMNSLKPEDTGIYYCAADTYYYCSKRVWRNDYGSWGQGTQVTVSS |

TABLE 6

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 170). CDR1 (underlined), CDR2 (*italics*), and CDR3 (bold) domains are also indicated, and are listed separately in Table 10.

| Name | SEQ ID NO: | Sequence |
|---|---|---|
| NbhmMMRm14.4 | 19 | QVQLQESGGGLVQAGDSLRLSCAASG<u>RTFSINYMG</u>WYRQAPGKQRELVAA*ITSGSGS*TNYADSVKGRFTISRDNAKNTMYLQMNSLKPEDTAVYYCNADMDSSLSGGYVDVWGQGTQVTVSS |

TABLE 6-continued

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 170). CDR1 (underlined), CDR2 (*italics*), and CDR3 (bold) domains are also indicated, and are listed separately in Table 10.

| Name | SEQ ID NO: | Sequence |
|---|---|---|
| NbhmMM Rm6.71 | 20 | QVQLQESGGGLVQAGGSLRLSCAAS<u>GGTFDDSVIG</u>WFRQAPGKERE GVS*CISSNDGT*THYASPVKGRFTISSDNAKNTVYLQMNSLKPEDTAV YYCAAETPSIGSPCTSASYDYWGQGTQVTVSS |
| NbhmMM Rm24.31 | 21 | QVQLQESGGGLVQPGGSLRLSCTATG<u>FTLKNHHIG</u>WLRQAPGKERE GVA*SINSSGGS*TNYADSVQGRFTISRDNAKNTVFLQMNSLKSEDTA VYYCARLRRYYGLNLDPGSYDYWGQGTQVTVSS |
| NbhmMM Rm20.52 | 22 | QVQLQESGGGLVQAGGSLRLSCAAS<u>GRIFSAYAMG</u>WFRQAPGKERE FVAA*ISRSGDST*DYADSVKGRFTISRDSAKNMVYLQMNSLKPEDTA LYHCAARTVSAPPSAAWGYGYWGQGTQVTVSS |
| NbhmMM Rm3.49 | 23 | QVQLQESGGGLVQPGGSLRLSCAAS<u>GFSLDYYAIG</u>WFRQAPGKEREG IS*CISYKGGST*TYADSVKGRFTISKDNAKNTAYLQMNSLKPEDTGIYS CAAGFVCYNYDYWGQGTQVTVSS |
| NbhmMM Rm22.84 | 24 | QVQLQESGGGLVQPGGSLRLSCAAS<u>GRTFSNYVNYAMG</u>WFRQFPGK EREFVA*SISWSSV*TTYYADSVKGRFTISRDNAKNTVYLQMNSLKPED TAVYYCAAHLAQYSDYAYRDPHQFGAWGQGTQVTVSS |
| NbhmMM Rm19.52 | 25 | QVQLQESGGGLVQAGGSLRLSCLAS<u>GDTFSNYVMA</u>WFRQAPGKER EIVAA*IRLSGARY*VPDSVKGRFTISRDNAKNAMYLQMTSLKPEDTAR YYCAAGHTWGQYAYWGQGTQVTVSS |
| NbhmMM Rm21.22 | 26 | QVQLQESGGGLVQAGGSLRLSCAAS<u>GRTFSSAAMG</u>WFRQAPGKER EPVA*LINLDDGET*YYADIAKGRFTLSKDNAKNSVYLQMNSLKPEDT AVYYCAVRGRFDDNYEYWGQGTQVTVSS |
| NbhmMM Rm14.93 | 27 | QVQLQESGGGLVQAGDSLRLSCAAS<u>GRTFSINYMG</u>WYRQAPGKQR ELVAA*ITSGSGST*NYADSVKGRFTISRDNAKKTMYLQMNSLKPEDT AVYYCNADMDSSLSGGYVDVWGQGTQVTVSS |
| NbhmMM Rm15.49 | 28 | QVQLQESGGGLVQAGGSLRLSCAAS<u>GSTFSINNMG</u>WYRQAPGKQR ELVA*GITGGNT*HYADSVKGRFTISRDNAKNTMYLQMNSLKPEDTA VYYCNANWGAYWGQGTQVTVSS |
| NbhmMM Rm17.72 | 29 | QVQLQESGGGLVQPGGSLRLSCAAS<u>GSIVSINAMG</u>WYRQAPGKQRE LVAL*VTGSGRT*NLADSVKGRFTISRDNAKNTVYLQMNSLKPEDTAV YYCNVLVIGPLEGYDYWGQGTQVTVSS |
| NbhmMM Rm10.79 | 30 | QVQLQESGGGLVQPGGSLKLSCAAS<u>GSIFSIKTMG</u>WYRQAPGKQRE LVAA*VSSGGST*NYADSVKGRFTISRDNAKNAVYLQMNSLKPEDTA VYYCNADGVVAWDQPYDNYWGQGTQVTVSS |
| NbhmMM Rm7.67 | 31 | QVQLQESGGGLVQAGGSLRLSCVDQ<u>GRTFSVNAMA</u>WYRQAPGKQ RELVA*SITSSGLDT*QYAEGMKGRFTISKGNDKFSTYLQMNNLKPDDT AVYYCNAERWDNGMVYWGKGTQVTVSS |
| NbhmMM Rm8.67 | 32 | QVQLQESGGGLVQAGDSLRLSCLATG<u>SMFSINAWG</u>WYRQAPGKQR ELVA<u>SITSGGGST</u>EYAESVKGRFTISRDSAKNMLYLQMNSLRPEDTA VYYCNAERWDGYALGYSPNHGSGHRPYNYWGQGTQVTVSS |
| NbhmMM Rm13.89 | 33 | QVQLQESGGGLVQPGGSLRLSCAAS<u>GSIFSINAWG</u>WYRQAPGKQRE LVA*EITSSGST*NYADSVKGRFTISGDNAKNSVYLHMNNLEPEDTAV YYCKAVAVTFTTPRSDYWGRGTQVTVSS |
| NbhmMM Rm18.63 | 34 | QVQLQESGGGLVQPGGSLRLSCAPS<u>GSIISINAMA</u>WYRQAPGKEREL VAA*ISSGGST*YYADSVKGRFTISGDIAKNLLWLQMNSLKPEDTAMY YCAPGGGWRPGAWGQGTQVTVSS |

TABLE 6-continued

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminal extension containing a HA and 6xHis tag (AAAYPYDVPDYGSHHHHHH; SEQ ID NO: 170). CDR1 (underlined), CDR2 (*italics*), and CDR3 (bold) domains are also indicated, and are listed separately in Table 10.

| Name | SEQ ID NO: | Sequence |
|---|---|---|
| NbhmMMRm25.86 | 35 | QVQLQESGGGLVQPGGSLRLSCAGS<u>GFTVSTSMIN</u>WARQVPGKELE WLV*DVLPSGST*YYADPVKGRFTISRDNAQNTIYLQMNYLKPEDTAI YYCAINRETMPPFRGQGTQVTVSS |
| NbhmMMRm26.70 | 36 | QVQLQESGGGLVQPGGSLRLSCTAS<u>GFPFSSAPMS</u>WVRQAPGKELE WVS*YIGYTGTIT*DYANSVKGRFTISRDNAKNRLYLQMNSLKPEDTAV YFCAQGYARLIADSDLVRGQGTQVTVSS |
| NbhmMMRm27.95 | 37 | QVQLQESGGRLGAAGGSLRLSCTAS<u>GFPFNIYPMS</u>WVRQAPGKGFE WVS*YISHGGTTT*DYSDAVKGRFTISRDNAKNRLYLQMDSLKPEDTA VYFCAQGYARLMTDSELVRGQGTQVTVSS |

TABLE 7

Production yields and physico-chemical characteristics of the anti-human MMR and anti-human/mouse MMR cross-reactive Nbs. All Nbs produce between 0.7 and 9 mg/l *E coli* culture.

| Name | number of A.A. Nb + HA + His | MW Nb + HA + His (dalton) | Theoretical pi | Extinction coefficient (assuming all Cys form cystines) | Estimated production capacity (g/l *E. Coli*) |
|---|---|---|---|---|---|
| *anti-human MMR Nbs* | | | | | |
| NbhMMRm1.33 | 152 | 16545 | 6.30 | 30620 | 0.7 |
| NbhMMRm10.19 | 140 | 15188 | 6.63 | 31525 | 3.7 |
| NbhMMRm23.30 | 144 | 16150 | 5.71 | 63035 | 2.3 |
| NbhMMRm2.15 | 146 | 16095 | 5.58 | 29130 | 1.6 |
| NbhMMRm3.1 | 137 | 14961 | 6.63 | 30620 | 1.1 |
| NbhMMRm5.38 | 150 | 16535 | 5.51 | 36120 | 1.2 |
| NbhMMRm12.6 | 138 | 15011 | 6.13 | 23045 | 1.7 |
| NbhMMRm11.5 | 139 | 15106 | 7.17 | 26025 | 6.8 |
| NbhMMRm15.43 | 131 | 14266 | 8.00 | 30035 | 6.2 |
| NbhMMRm16.95 | 140 | 15025 | 7.17 | 26025 | 5.6 |
| NbhMMRm4.83 | 149 | 16395 | 6.70 | 36120 | 3.0 |
| *anti-human/anti-mouse MMR Nbs* | | | | | |
| NbhmMMRm14.4 | 141 | 15275 | 6.29 | 26025 | 1.6 |
| NbhmMMRm6.71 | 144 | 15295 | 5.70 | 24660 | 2.4 |
| NbhmMMRm24.31 | 144 | 15793 | 8.00 | 26025 | 1.0 |
| NbhmMMRm20.52 | 143 | 15431 | 8.00 | 30035 | 5.4 |
| NbhmMMRm3.49 | 137 | 14875 | 6.63 | 29130 | 1.6 |
| NbhmMMRm22.84 | 149 | 16628 | 7.25 | 35995 | 4.2 |
| NbhmMMRm19.52 | 136 | 14986 | 8.59 | 31525 | 4.1 |
| NbhmMMRm21.22 | 137 | 15045 | 5.91 | 26025 | 2.1 |
| NbhmMMRm14.93 | 141 | 15289 | 6.63 | 26025 | 2.6 |
| NbhmMMRm15.49 | 131 | 14226 | 8.00 | 30035 | 4.0 |
| NbhmMMRm17.72 | 138 | 14896 | 7.18 | 24535 | 3.4 |
| NbhmMMRm10.79 | 140 | 15130 | 6.63 | 31525 | T.B.D |
| NbhmMMRm7.67 | 137 | 15153 | 7.18 | 30035 | 4.0 |
| NbhmMMRm8.67 | 151 | 16635 | 6.76 | 40005 | 2.0 |
| NbhmMMRm13.89 | 139 | 15096 | 6.70 | 30035 | 5.4 |
| NbhmMMRm18.63 | 135 | 14393 | 7.18 | 34045 | 9.0 |
| NbhmMMRm25.86 | 135 | 14891 | 6.29 | 24535 | 3.9 |
| NbhmMMRm26.70 | 140 | 15299 | 7.18 | 24535 | 6.0 |
| NbhmMMRm27.95 | 140 | 15392 | 7.22 | 24535 | 1.0 |

T.B.D.: to be determined.

TABLE 8

SPR kinetic and equilibrium parameters for anti-MMR Nanobodies on mouse MMR.

| Sample | $k_a$ (1/Ms) | $k_d$ (1/s) | $K_D$ | Chi² |
|---|---|---|---|---|
| Anti-MMR Nb1 | 5.76E+05 | 0.01331 | 2.31E−08 | 0.558 |
| Anti-MMR Nb3 | 9.73E+04 | 0.01859 | 1.91E−07 | 0.190 |
| NbhMMRm1.33 | NB | NB | NB | |
| NbhMMRm2.15 | NB | NB | NB | |
| NbhMMRm5.38 | 1.3E+5 | 3.3E−3 | 2.5E−8 | 0.216 |
| NbhMMRm10.19 | 8.4E+5 | 2.1E−1 | 2.5E−7 | 0.280 |
| NbhMMRm11.5 | 1.5E+5 | 1.9E−2 | 1.2E−7 | 0.211 |
| NbhMMRm12.6 | NB | NB | NB | |
| NbhMMRm15.43 | 2.9E+4 | 1.3E−3 | 4.4E−8 | 0.299 |
| NbhMMRm16.95 | NB | NB | NB | |
| NbhMMRm23.30 | NB | NB | NB | |
| NbhmMMRm3.1 | 2.1E+5 | 4.0E−3 | 1.9E−8 | 0.459 |
| NbhmMMRm3.49 | 2.9E+5 | 3.6E−3 | 1.2E−8 | 0.451 |
| NbhmMMRm6.71 | NB | NB | NB | |
| NbhmMMRm7.67 | NB | NB | NB | |
| NbhmMMRm10.79 | 1.1E+5 | 4.2E−3 | 3.9E−8 | 0.441 |
| NbhmMMRm14.4 | 3.3E+4 | 2.3E−3 | 6.8E−8 | 0.0343 |
| NbhmMMRm14.93 | 2.9E+4 | 2.1E−3 | 7.4E−8 | 0.0389 |
| NbhmMMRm15.49 | 2.9E+4 | 1.3E−3 | 4.4E−8 | 0.258 |
| NbhmMMRm17.72 | NB | NB | NB | |
| NbhmMMRm19.52 | 3.7E+3 | 3.2E−2 | 8.5E−6 | 0.204 |
| NbhmMMRm20.52 | 1.6E+6 | 2.0E−3 | 1.3E−9 | 1.10 |
| NbhmMMRm21.22 | NB | NB | NB | |
| NbhmMMRm22.84 | 3.0E+4 | 4.0E−3 | 1.3E−7 | 0.0634 |
| NbhmMMRm24.31 | 2.8E+4 | 2.1E−3 | 7.4E−8 | 0.0389 |
| NbhmMMRm26.70 | 6.9E+5 | 1.3E−3 | 1.9E−9 | 0.653 |

Nb: Nanobody;
SE: standard error;
NB: no binding.

TABLE 9

SPR kinetic and equilibrium parameters for anti-MMR Nanobodies on human MMR.

| Sample | $k_a$ (1/Ms) | $k_d$ (1/s) | $K_D$ | Chi² |
|---|---|---|---|---|
| Anti-MMR Nb1 | NB | NB | NB | |
| Anti-MMR Nb3 | NB | NB | NB | |
| NbhMMRm1.33 | 2.0E+5 | 1.5E−3 | 7.7E−9 | 0.394 |
| NbhMMRm2.15 | 1.5E+5 | 1.3E−3 | 8.6E−9 | 0.209 |
| NbhMMRm5.38 | 2.0E+5 | 6.6E−4 | 3.3E−9 | 0.144 |
| NbhMMRm10.19 | 7.5E+5 | 3.1E−2 | 5.0E−8 | 0.240 |
| NbhMMRm11.5 | 4.0E+5 | 2.2E−2 | 5.5E−8 | 0.246 |
| NbhMMRm12.6 | 1.5E+5 | 1.2E−3 | 8.2E−9 | 0.132 |
| NbhMMRm15.43 | 2.2E+4 | 5.9E−3 | 2.7E−7 | 0.201 |
| NbhMMRm16.95 | 6.6E+4 | 1.4E−3 | 2.1E−8 | 0.496 |
| NbhMMRm23.30 | NB | NB | NB | |
| NbhmMMRm3.1 | 2.2E+5 | 7.4E−4 | 3.4E−9 | 0.157 |
| NbhmMMRm3.49 | 4.4E+5 | 8.0E−4 | 1.8E−9 | 0.271 |
| NbhmMMRm6.71 | 1.9E+5 | 1.1E−3 | 5.6E−9 | 0.185 |
| NbhmMMRm7.67 | NB | NB | NB | |
| NbhmMMRm10.79 | 1.6E+4 | 6.6E−3 | 4.2E−7 | 0.122 |
| NbhmMMRm14.4 | 1.4E+5 | 1.4E−3 | 1.0E−8 | 0.136 |
| NbhmMMRm14.93 | 9.5E+4 | 1.2E−3 | 1.3E−8 | 0.135 |
| NbhmMMRm15.49 | 2.1E+4 | 6.1E−3 | 2.9E−7 | 0.196 |
| NbhmMMRm17.72 | 6.2E+4 | 1.2E−3 | 1.9E−8 | 0.442 |
| NbhmMMRm19.52 | 6.0E+3 | 1.0E−2 | 1.7E−6 | 0.107 |
| NbhmMMRm20.52 | 5.1E+5 | 1.3E−1 | 2.6E−7 | 0.392 |
| NbhmMMRm21.22 | 3.4E+5 | 1.2E−3 | 3.6E−9 | 1.72 |
| NbhmMMRm22.84 | 4.9E+5 | 1.9E−3 | 3.8E−9 | 0.262 |
| NbhmMMRm24.31 | 2.6E+5 | 6.9E−4 | 2.7E−9 | 0.386 |
| NbhmMMRm26.70 | 5.8E+5 | 7.3E−3 | 1.3E−8 | 1.03 |

Nb: Nanobody;
SE: standard error;
NB: no binding.

TABLE 10

CDRs of MMR-specific Nanobodies

| Nanobody reference number | SEQ ID NO[1] | CDR1 | CDR2 | CDR3 |
|---|---|---|---|---|
| Nanobody clone 1 | 2 | SGNIFSINAIG (SEQ ID NO: 38) | TITLSGSTN (SEQ ID NO: 70) | NTYSDSDVYGY (SEQ ID NO: 102) |
| Nanobody clone 3 | 4 | SGRTFSRDAMG (SEQ ID NO: 39) | GISWSGGST (SEQ ID NO: 71) | SSIYGSAVVDGLYDY (SEQ ID NO: 103) |
| NbhMMRm1.33 | 8 | GFTLDNYTVA (SEQ ID NO: 40) | CISSSGGST (SEQ ID NO: 72) | ERAPPYYSGYYFFDSTCVAASYDY (SEQ ID NO: 104) |
| NbhMMRm10.19 | 9 | GSIFSIKTMG (SEQ ID NO: 41) | AITSGGST (SEQ ID NO: 73) | DGVVAWDQPYDNY (SEQ ID NO: 105) |
| NbhMMRm23.30 | 10 | GDTFNHYSWG (SEQ ID NO: 42) | AISWNGGS (SEQ ID NO: 74) | DRRPYNDWWDDWSWWVY (SEQ ID NO: 106) |
| NbhMMRm2.15 | 11 | GFTLDYYDIG (SEQ ID NO: 43) | CISSIGGSA (SEQ ID NO: 75) | EAQTPYNDGDCTRASYDY (SEQ ID NO: 107) |
| NbhMMRm3.1 | 12 | GFTLDYYAIG (SEQ ID NO: 44) | CISYKGGST (SEQ ID NO: 76) | GFVCYNYDY (SEQ ID NO: 108) |
| NbhMMRm5.38 | 13 | GFTDDDYDIG (SEQ ID NO: 45) | CISSSDGST (SEQ ID NO: 77) | DFFRWDSGSYYVRGCRHATYDY (SEQ ID NO: 109) |

TABLE 10-continued

CDRs of MMR-specific Nanobodies

| Nanobody reference number | SEQ ID NO[1] | CDR1 | CDR2 | CDR3 |
|---|---|---|---|---|
| NbhMMRm12.6 | 14 | GSFLSINHMG (SEQ ID NO: 46) | AITSGGST (SEQ ID NO: 78) | DALTMLPPFDF (SEQ ID NO: 110) |
| NbhMMRm11.5 | 15 | GNIFTINRMG (SEQ ID NO: 47) | AITSGGNT (SEQ ID NO: 79) | AIVTMTSPYSDY (SEQ ID NO: 111) |
| NbhMMRm15.43 | 16 | GSTFSINNMG (SEQ ID NO: 48) | GITGGNT (SEQ ID NO: 80) | NWGAY (SEQ ID NO: 112) |
| NbhMMRm16.95 | 17 | GRIASISAMG (SEQ ID NO: 49) | AITGSGRT (SEQ ID NO: 81) | LMVDYGLGLGTDY (SEQ ID NO: 113) |
| NbhMMRm4.83 | 18 | PGFKLDYYAIA (SEQ ID NO: 50) | CIGGSGSGLTDTYYYCSKRVWRNDYGS (SEQ ID NO: 82) | (SEQ ID NO: 114) |
| NbhmMMRm14.4 | 19 | GRTFSINYMG (SEQ ID NO: 51) | AITSGSGST (SEQ ID NO: 83) | DMDSSLSGGYVDV (SEQ ID NO: 115) |
| NbhmMMRm6.71 | 20 | GGTFDDSVIG (SEQ ID NO: 52) | CISSNDGTT (SEQ ID NO: 84) | ETPSIGSPCTSASYDY (SEQ ID NO: 116) |
| NbhmMMRm24.31 | 21 | GFTLKNHHIG (SEQ ID NO: 53) | SINSSGGST (SEQ ID NO: 85) | LRRYYGLNLDPGSYDY (SEQ ID NO: 117) |
| NbhmMMRm20.52 | 22 | GRIFSAYAMG (SEQ ID NO: 54) | AISRSGDST (SEQ ID NO: 86) | RTVSAPPSAAWGYGY (SEQ ID NO: 118) |
| NbhmMMRm3.49 | 23 | GFSLDYYAIG (SEQ ID NO: 55) | CISYKGGST (SEQ ID NO: 87) | GFVCYNYDY (SEQ ID NO: 119) |
| NbhmMMRm22.84 | 24 | GRTFSNYVNYAMG (SEQ ID NO: 56) | SISWSSVTT (SEQ ID NO: 88) | HLAQYSDYAYRDPHQFGA (SEQ ID NO: 120) |
| NbhmMMRm19.52 | 25 | GDTFSNYVMA (SEQ ID NO: 57) | AIRLSGAR (SEQ ID NO: 89) | GHTWGQYAY (SEQ ID NO: 121) |
| NbhmMMRm21.22 | 26 | GRTFSSAAMG (SEQ ID NO: 58) | LINLDDGET (SEQ ID NO: 90) | RGRFDDNYEY (SEQ ID NO: 122) |
| NbhmMMRm14.93 | 27 | GRTFSINYMG (SEQ ID NO: 59) | AITSGSGST (SEQ ID NO: 91) | DMDSSLSGGYVDV (SEQ ID NO: 123) |
| NbhmMMRm15.49 | 28 | GSTFSINNMG (SEQ ID NO: 60) | GITGGNT (SEQ ID NO: 92) | NWGAY (SEQ ID NO: 124) |
| NbhmMMRm17.72 | 29 | GSIVSINAMG (SEQ ID NO: 61) | LVTGSGRT (SEQ ID NO: 93) | LVIGPLEGYDY (SEQ ID NO: 125) |
| NbhmMMRm10.79 | 30 | GSIFSIKTMG (SEQ ID NO: 62) | AVSSGGST (SEQ ID NO: 94) | DGVVAWDQPYDNY (SEQ ID NO: 126) |
| NbhmMMRm7.67 | 31 | GRTFSVNAMA (SEQ ID NO: 63) | SITSSGLDT (SEQ ID NO: 95) | ERWDNGMVY (SEQ ID NO: 127) |

TABLE 10-continued

CDRs of MMR-specific Nanobodies

| Nanobody reference number | SEQ ID NO[1] | CDR1 | CDR2 | CDR3 |
|---|---|---|---|---|
| NbhmMMRm8.67 | 32 | GSMFSINAWG (SEQ ID NO: 64) | SITSGGGST (SEQ ID NO: 96) | ERWDGYALGYSPNHGSGHRPYNY (SEQ ID NO: 128) |
| NbhmMMRm13.89 | 33 | GSIFSINAWG (SEQ ID NO: 65) | EITSSGST (SEQ ID NO: 97) | VAVTFTTPRSDY (SEQ ID NO: 129) |
| NbhmMMRm18.63 | 34 | GSIISINAMA (SEQ ID NO: 66) | AISSGGST (SEQ ID NO: 98) | GGGWRPGA (SEQ ID NO: 130) |
| NbhmMMRm25.86 | 35 | GFTVSTSMIN (SEQ ID NO: 67) | DVLPSGST (SEQ ID NO: 99) | NRETMPPF (SEQ ID NO: 131) |
| NbhmMMRm26.70 | 36 | GFPFSSAPMS (SEQ ID NO: 68) | YIGYTGTIT (SEQ ID NO: 100) | GYARLIADSDLV (SEQ ID NO: 132) |
| NbhmMMRm27.95 | 37 | GFPFNIYPMS (SEQ ID NO: 69) | YISHGGTTT (SEQ ID NO: 101) | GYARLMTDSELV (SEQ ID NO: 133) |

[1]Nanobody sequences without His tag

TABLE 11

Amino acid sequences of human and mouse macrophage mannose receptor

| Name | SEQ ID NO | Amino acid sequence |
|---|---|---|
| Human MMR (MRC1) | 141 | MRLPLLLVFASVIPGAVLLLDTRQFLIYNEDHKRCVDAVS PSAVQTAACNQDAESQKFRWVSESQIMSVAFKLCLGVPS KTDWVAITLYACDSKSEFQKWECKNDTLLGIKGEDLFFN YGNRQEKNIMLYKGSGLWSRWKIYGTTDNLCSRGYEAM YTLLGNANGATCAFPPFKFENKWYADCTSAGRSDGWLW CGTTTDYDTDKLFGYCPLKFEGSESLWNKDPLTSVSYQIN SKSALTWHQARKSCQQQNAELLSITEIHEQTYLTGLTSSL TSGLWIGLNSLSFNSGWQWSDRSPFRYLNWLPGSPSAEP GKSCVSLNPGKNAKWENLECVQKLGYICKKGNTTLNSF VIPSESDVPTHCPSQWWPYAGHCYKIHRDEKKIQRDALT TCRKEGGDLTSIHTIEELDFIISQLGYEPNDELWIGLNDIKI QMYFEWSDGTPVTFTKWLRGEPSHENNRQEDCVVMKG KDGYWADRGCEWPLGYICKMKSRSQGPEIVEVEKGCRK GWKKHHFYCYMIGHTLSTFAEANQTCNNENAYLTTIEDR YEQAFLTSFVGLRPEKYFWTGLSDIQTKGTFQWTIEEEVR FTHWNSDMPGRKPGCVAMRTGIAGGLWDVLKCDEKAK FVCKHWAEGVTHPPKPTTTPEPKCPEDWGASSRTSLCFK LYAKGKHEKKTWFESRDFCRALGGDLASINNKEEQQTIW RLITASGSYHKLFWLGLTYGSPSEGFTWSDGSPVSYENW AYGEPNNYQNVEYCGELKGDPTMSWNDINCEHLNNWIC QIQKGQTPKPEPTPAPQDNPPVTEDGWVIYKDYQYYFSK EKETMDNARAFCKRNFGDLVSIQSESEKKFLWKYVNRN DAQSAYFIGLLISLDKKFAWMDGSKVDYVSWATGEPNF ANEDENCVTMYSNSGFWNDINCGYPNAFICQRHNSSINA TTVMPTMPSVPSGCKEGWNFYSNKCFKIFGFMEEERKN WQEARKACIGFGGNLVSIQNEKEQAFLTYHMKDSTFSA WTGLNDVNSEHTFLWTDGRGVHYTNWGKGYPGGRRSS LSYEDADCVVIIGGASNEAGKWMDDTCDSKRGYICQTRS DPSLTNPPATIQTDGFVKYGKSSYSLMRQKFQWHEAETY CKLHNSLIASILDPYSNAFAWLQMETSNERVWIALNSNLT DNQYTWTDKWRVRYTNWAADEPKLKSACVYLDLDGY WKTAHCNESFYFLCKRSDEIPATEPPQLPGRCPESDHTAW IPFHGHCYYIESSYTRNWGQASLECLRMGSSLVSIESAAES SFLSYRVEPLKSKTNFWIGLFRNVEGTWLWINNSPVSFVN WNTGDPSGERNDCVALHASSGFWSNIHCSSYKGYICKRP KIIDAKPTIIELLTTKADTRKMDPSKPSSNVAGVVIIVILLIL TGAGLAAYFFYKKRRVHLPQEGAFENTLYFNSQSSPGTS DMKDLVGNIEQNEHSVI |

TABLE 11-continued

Amino acid sequences of human and mouse macrophage mannose receptor

| Name | SEQ ID NO | Amino acid sequence |
|---|---|---|
| Recombinant human MMR (R & D Systems Catalog Number: 2535-MM/CF) | 142 | LLDTRQFLIYNEDHKRCVDAVSPSAVQTAACNQDAESQK FRWVSESQIMSVAFKLCLGVPSKTDWVAITLYACDSKSE FQKWECKNDTLLGIKGEDLFFNYGNRQEKNIMLYKGSGL WSRWKIYGTTDNLCSRGYEAMYTLLGNANGATCAFPFK FENKWYADCTSAGRSDGWLWCGTTTDYDTDKLFGYCPL KFEGSESLWNKDPLTSVSYQINSKSALTWHQARKSCQQQ NAELLSITEIHEQTYLTGLTSSLTSGLWIGLNSLSFNSGWQ WSDRSPFRYLNWLPGSPSAEPGKSCVSLNPGKNAKWENL ECVQKLGYICKKGNTTLNSFVIPSESDVPTHCPSQWWPY AGHCYKIHRDEKKIQRDALTTCRKEGGDLASIHTIEEFDFI ISQLGYEPNDELWIGLNDIKIQMYFEWSDGTPVTFTKWLR GEPSHENNRQEDCVVMKGKDGYWADRGCEWPLGYICK MKSRSQGPEIVEVEKGCRKGWKKHHFYCYMIGHTLSTFA EANQTCNNENAYLTTIEDRYEQAFLTSFVGLRPEKYFWT GLSDIQTKGTFQWTIEEEVRFTHWNSDMPGRKPGCVAMR TGIAGGLWDVLKCDEKAKFVCKHWAEGVTHPPKPTTTP EPKCPEDWGASSRTSLCFKLYAKGKHEKKTWFESRDFCR ALGGDLASINNKEEQQTIWRLITASGSYHKLFWLGLTYGS PSEGFTWSDGSPVSYENWAYGEPNNYQNVEYCGELKGD PTMSWNDINCEHLNNWICQIQKGQTPKPEPTPAPQDNPPV TEDGWVIYKDYQYYFSKEKETMDNARAFCKRNFGDLVS IQSESEKKFLWKYVNRNDAQSAYFIGLLISLDKKFAWMD GSKVDYVSWATGEPNFANEDENCVTMYSNSGFWNDINC GYPNAFICQRHNSSINATTVMPTMPSVPSGCKEGWNFYS NKCFKIFGFMEEERKNWQEARKACIGFGGNLVSIQNEKE QAFLTYHMKDSTFSAWTGLNDVNSEHTFLWTDGRGVHY TNWGKGYPGGRRSSLSYEDADCVVIIGGASNEAGKWMD DTCDSKRGYICQTRSDPSLTNPPATIQTDGFVKYGKSSYS LMRQKFQWHEAETYCKLHNSLIASILDPYSNAFAWLQME TSNERVWIALNSNLTDNQYTWTDKWRVRYTNWAADEP KLKSACVYLDLDGYWKTAHCNESFYFLCKRSDEIPATEP PQLPGRCPESDHTAWIPFHGHCYYIESSYTRNWGQASLEC LRMGSSLVSIESAAESSFLSYRVEPLKSKTNFWIGLFRNVE GTWLWINNSPVSFVNWNTGDPSGERNDCVALHASSGFW SNIHCSSYKGYICKRPKIIDAKPTHELLTTKADTRKMDPSK HHHHHH |
| Mouse MMR (Mrc1) | 143 | MRLLLLLAFISVIPVSVQLLDARQFLIYNEDHKRCVDALS AISVQTATCNPEAESQKFRWVSDSQIMSVAFKLCLGVPSK TDWASVTLYACDSKSEYQKWECKNDTLFGIKGTELYFN YGNRQEKNIKLYKGSGLWSRWKVYGTTDDLCSRGYEA MYSLLGNANGAVCAFPFKFENKWYADCTSAGRSDGWL WCGTTTDYDKDKLFGFCPLHFEGSERLWNKDPLTGILYQ INSKSALTWHQARASCKQQNADLLSVTEIHEQMYLTGLT SSLSSGLWIGLNSLSVRSGWQWAGGSPFRYLNWLPGSPS SEPGKSCVSLNPGKNAKWENLECVQKLGYICKKGNNTL NPFIIPSASDVPTGCPNQWWPYAGHCYRIHREEKKIQKYA LQACRKEGGDLASIHSIEEFDFIFSQLGYEPNDELWIGLND IKIQMYFEWSDGTPVTFTKWLPGEPSHENNRQEDCVVMK GKDGYWADRACEQPLGYICKMVSQSHAVVPEGADKGC RKGWKRHGFYCYLIGSTLSTFTDANHTCTNEKAYLTTVE DRYEQAFLTSLVGLRPEKYFWTGLSDVQNKGTFRWTVD EQVQFTHWNADMPGRKAGCVAMKTGVAGGLWDVLSC EEKAKFVCKHWAEGVTRPPEPTTTPEPKCPENWGTTSKT SMCFKLYAKGKHEKKTWFESRDFCKAIGGELASIKSKDE QQVIWRLITSSGSYHELFWLGLTYGSPSEGFTWSDGSPVS YENWAYGEPNNYQNVEYCGELKGDPGMSWNDINCEHL NNWICQIQKGKTLLPEPTPAPQDNPPVTADGWVIYKDYQ YYFSKEKETMDNARAFCKKNFGDLATIKSESEKKFLWKY INKNGGQSPYFIGMLISMDKKFIWMDGSKVDFVAWATGE PNFANDDENCVTMYTNSGFWNDINCGYPNNFICQRHNSS INATAMPTTPTTPGGCKEGWHLYKNKCFKIFGFANEEKK SWQDARQACKGLKGNLVSIENAQEQAFVTYHMRDSTFN AWTGLNDINAEHMFLWTAGQGVHYTNWGKGYPGGRRS SLSYEDADCVVIGGNSREAGTWMDDTCDSKQGYICQT QTDPSLPVSPTTTPKDGFVTYGKSSYSLMKLKLPWHEAE TYCKDHTSLLASILDPYSNAFAWMKMHPFNVPIWIALNS NLTNNEYTWTDRWRVRYTNWGADEPKLKSACVYMDV DGYWRTSYCNESFYFLCKKSDEIPATEPPQLPGKCPESEQ TAWIPFYGHCYYFESSFTRSWGQASLECLRMGASLVSIET AAESSFLSYRVEPLKSKTNFWIGMFRNVEGKWLWLNDN PVSFVNWKTGDPSGERNDCVVLASSSGLWNNIHCSSYKG FICKMPKIIDPVTTHSSITTKADRKMDPQKPKGSSKAAGV |

TABLE 11-continued

Amino acid sequences of human and mouse macrophage mannose receptor

| Name | SEQ ID NO | Amino acid sequence |
|---|---|---|
| | | VTVVLLIVIGAGVAAYFFYKKRHALHIPQEATFENTLYFN<br>SNLSPGTSDTKDLMGNIEQNEHAII |
| Recombinant mouse MMR (R & D systems) | 144 | LLDARQFLIYNEDHKRCVDALSAISVQTATCNPEAESQKF<br>RWVSDSQIMSVAFKLCLGVPSKTDWASVTLYACDSKSEY<br>QKWECKNDTLFGIKGTELYFNYGNRQEKNIKLYKGSGL<br>WSRWKVYGTTDDLCSRGYEAMYSLLGNANGAVCAFPF<br>KFENKWYADCTSAGRSDGWLWCGTTTDYDKDKLFGFC<br>PLHFEGSERLWNKDPLTGILYQINSKSALTWHQARASCK<br>QQNADLLSVTEIHEQMYLTGLTSSLSSGLWIGLNSLSVRS<br>GWQWAGGSPFRYLNWLPGSPSSEPGKSCVSLNPGKNAK<br>WENLECVQKLGYICKKGNNTLNPFIIPSASDVPTGCPNQW<br>WPYAGHCYRIHREEKKIQKYALQACRKEGGDLASIHSIEE<br>FDFIFSQLGYEPNDELWIGLNDIKIQMYFEWSDGTPVTFT<br>KWLPGEPSHENNRQEDCVVMKGKDGYWADRACEQPLG<br>YICKMVSQSHAVVPEGADKGCRKGWKRHGFYCYLIGST<br>LSTFTDANHTCTNEKAYLTTVEDRYEQAFLTSLVGLRPE<br>KYFWTGLSDVQNKGTFRWTVDEQVQFTHWNADMPGRK<br>AGCVAMKTGVAGGLWDVLSCEEKAKFVCKHWAEGVTR<br>PPEPTTTPEPKCPENWGTTSKTSMCFKLYAKGKHEKKTW<br>FESRDFCKAIGGELASIKSKDEQQVIWRLITSSGSYHELFW<br>LGLTYGSPSEGFTWSDGSPVSYENWAYGEPNNYQNVEY<br>CGELKGDPGMSWNDINCEHLNNWICQIQKGKTLLPEPTP<br>APQDNPPVTADGWVIYKDYQYYFSKEKETMDNARAFCK<br>KNFGDLATIKSESEKKFLWKYINKNGGQSPYFIGMLISMD<br>KKFIWMDGSKVDFVAWATGEPNFANDDENCVTMYTNS<br>GFWNDINCGYPNNFICQRHNSSINATAMPTTPTTPGGCKE<br>GWHLYKNKCFKIFGFANEEKKSWQDARQACKGLKGNL<br>VSIENAQEQAFVTYHMRDSTFNAWTGLNDINAEHMFLW<br>TAGQGVHYTNWGKGYPGGRRSSLSYEDADCVVVIGGNS<br>REAGTWMDDTCDSKQGYICQTQTDPSLPVSPTTTPKDGF<br>VTYGKSSYSLMKLKLPWHEAETYCKDHTSLLASILDPYS<br>NAFAWMKMHPFNVPIWIALNSNLTNNEYTWTDRWRVR<br>YTNWGADEPKLKSACVYMDVDGYWRTSYCNESFYFLC<br>KKSDEIPATEPPQLPGKCPESEQTAWIPFYGHCYYFESSFT<br>RSWGQASLECLRMGASLVSIETAAESSFLSYRVEPLKSKT<br>NFWIGMFRNVEGKWLWLNDNPVSFVNWKTGDPSGERN<br>DCVVLASSSGLWNNIHCSSYKGFICKMPKIIDPVTTHSSIT<br>TKADQRKMDPQPKGSSKAHHHHHH |
| Human MMR (MRC1)-ectodomain | 145 | LLDTRQFLIYNEDHKRCVDAVSPSAVQTAACNQDAESQK<br>FRWVSESQIMSVAFKLCLGVPSKTDWVAITLYACDSKSE<br>FQKWECKNDTLLGIKGEDLFFNYGNRQEKNIMLYKGSGL<br>WSRWKIYGTTDNLCSRGYEAMYTLLGNANGATCAFPFK<br>FENKWYADCTSAGRSDGWLWCGTTTDYDTDKLFGYCPL<br>KFEGSESLWNKDPLTSVSYQINSKSALTWHQARKSCQQQ<br>NAELLSITEIHEQTYLTGLTSSLTGLWIGLNSLSFNSGWQ<br>WSDRSPFRYLNWLPGSPSAEPGKSCVSLNPGKNAKWENL<br>ECVQKLGYICKKGNTTLNSFVIPSESDVPTHCPSQWWPY<br>AGHCYKIHRDEKKIQRDALTTCRKEGGDLTSIHTIEELDFI<br>ISQLGYEPNDELWIGLNDIKIQMYFEWSDGTPVTFTKWLR<br>GEPSHENNRQEDCVVMKGKDGYWADRGCEWPLGYICK<br>MKSRSQGPEIVEVEKGCRKGWKKHHFYCYMIGHTLSFA<br>EANQTCNNENAYLTTIEDRYEQAFLTSFVGLRPEKYFWT<br>GLSDIQTKGTFQWTIEEEVRFTHWNSDMPGRKPGCVAMR<br>TGIAGGLWDVLKCDEKAKFVCKHWAEGVTHPPKPTTTP<br>EPKCPEDWGASSRTSLCFKLYAKGKHEKKTWFESRDFCR<br>ALGGDLASINNKEEQQTIWRLITASGSYHKLFWLGLTYGS<br>PSEGFTWSDGSPVSYENWAYGEPNNYQNVEYCGELKGD<br>PTMSWNDINCEHLNNWICQIQKGQTPKPEPTPAPQDNPPV<br>TEDGWVIYKDYQYYFSKEKETMDNARAFCKRNFGDLVS<br>IQSESEKKFLWKYVNRNDAQSAYFIGLLISLDKKFAWMD<br>GSKVDYVSWATGEPNFANEDENCVTMYSNSGFWNDINC<br>GYPNAFICQRHNSSINATTVMPTMPSVPSGCKEGWNFYS<br>NKCFKIFGFMEEERKNWQEARKACIGFGGNLVSIQNEKE<br>QAFLTYHMKDSTFSAWTGLNDVNSEHTFLWTDGRGVHY<br>TNWGKGYPGGRRSSLSYEDADCVVIIGGASNEAGKWMD<br>DTCDSKRGYICQTRSDPSLTNPPATIQTDGFVKYGKSSYS<br>LMRQKFQWHEAETYCKLHNSLIASILDPYSNAFAWLQME<br>TSNERVWIALNSNLTDNQYTWTDKWRVRYTNWAADEP<br>KLKSACVYLDLDGYWKTAHCNESFYFLCKRSDEIPATEP<br>PQLPGRCPESDHTAWIPFHGHCYYIESSYTNWGQASLEC<br>LRMGSSLVSIESAAESSFLSYRVEPLKSKTNFWIGLFRNVE |

TABLE 11-continued

Amino acid sequences of human and mouse macrophage mannose receptor

| Name | SEQ ID NO | Amino acid sequence |
|------|-----------|---------------------|
| | | GTWLWINNSPVSFVNWNTGDPSGERNDCVALHASSGFW SNIHCSSYKGYICKRPKIIDAKPTHELLTTKADTRKMDPSK |
| Mouse MMR (Mrc1)-ectodomain | 146 | LLDARQFLIYNEDHKRCVDALSAISVQTATCNPEAESQKF RWVSDSQIMSVAFKLCLGVPSKTDWASVTLYACDSKSEY QKWECKNDTLFGIKGTELYFNYGNRQEKNIKLYKGSGL WSRWKVYGTTDDLCSRGYEAMYSLLGNANGAVCAFPF KFENKWYADCTSAGRSDGWLWCGTTTDYDKDKLFGFC PLHFEGSERLWNKDPLTGILYQINSKSALTWHQARASCK QQNADLLSVTEIHEQMYLTGLTSSLSSGLWIGLNSLSVRS GWQWAGGSPFRYLNWLPGSPSSEPGKSCVSLNPGKNAK WENLECVQKLGYICKKGNNTLNPFIIPSASDVPTGCPNQW WPYAGHCYRIHREEKKIQKYALQACRKEGGDLASIHSIEE FDFIFSQLGYEPNDELWIGLNDIKIQMYFEWSDGTPVTFT KWLPGEPSHENNRQEDCVVMKGKDGYWADRACEQPLG YICKMVSQSHAVVPEGADKGCRKGWKRHGFYCYLIGST LSTFTDANHTCTNEKAYLTTVEDRYEQAFLTSLVGLRPE KYFWTGLSDVQNKGTFRWTVDEQVQFTHWNADMPGRK AGCVAMKTGVAGGLWDVLSCEEKAKFVCKHWAEGVTR PPEPTTTPEPKCPENWGTTSKTSMCFKLYAKGKHEKKTW FESRDFCKAIGGELASIKSKDEQQVIWRLITSSGSYHELFW LGLTYGSPSEGFTWSDGSPVSYENWAYGEPNNYQNVEY CGELKGDPGMSWNDINCEHLNNWICQIQKGKTLLPEPTP APQDNPPVTADGWVIYKDYQYYFSKEKETMDNARAFCK KNFGDLATIKSESEKKFLWKYINKNGGQSPYFIGMLISMD KKFIWMDGSKVDFVAWATGEPNFANDDENCVTMYTNS GFWNDINCGYPNNFICQRHNSSINATAMPTTPTTPGGCKE GWHLYKNKCFKIFGFANEEKKSWQDARQACKGLKGNL VSIENAQEQAFVTYHMRDSTFNAWTGLNDINAEHMFLW TAGQGVHYTNWGKGYPGGRRSSLSYEDADCVVVIGGNS REAGTWMDDTCDSKQGYICQTQTDPSLPVSPTTTPKDGF VTYGKSSYSLMKLKLPWHEAETYCKDHTSLLASILDPYS NAFAWMKMHPFNVPIWIALNSNLTNNEYTWTDRWRVR YTNWGADEPKLKSACVYMDVDGYWRTSYCNESFYFLC KKSDEIPATEPPQLPGKCPESEQTAWIPFYGHCYYFESSFT RSWGQASLECLRMGASLVSIETAAESSFLSYRVEPLKSKT NFWIGMFRNVEGKWLWLNDNPVSFVNWKTGDPSGERN DCVVLASSSGLWNNIHCSSYKGFICKMPKIIDPVTTHSSIT TKADQRKMDPQPKGSSKA |
| Rat Full-length *Rattus norvegicus* MRC1 (NCBI Reference Sequence: NP_001099593.1) | 147 | MEHTLWAMRLPLLLAFISVIPVAVQLLDSRQFLIYNEDHK RCVDALSAISVQTATCNPEAESQKFRWVSESQIMSVAFKL CLGVPSKTDWASVTLYACDSKSEFQKWECKNDTLFGIKG TELYFNYGNRQEKNIKLYKGSGLWSRWKVYGTTDDLCS RGYEAMYSLLGNANGAVCAFPFKFENKWYADCTSAGRS DGWLWCGTTTDYDTDKLFGFCPLQFEGSKRLWNTDPLT GILYQINSKSALTWHQARASCKQQNAELLSVTEIHEQMY LTGLTSSLTSGLWIGLNSLSLSTGWQWAGGSPFRYLNWL PGSPSSEPGKSCVSLNPGKNAKWENLECVQKLGYICKKG NNTLNPFIIPSESDVPTACPNQWWPYAGHCYRIYREEKKI QKYALQACRKEGGDLASIHSIEEFDFIFSQLGYEPNDELWI GLNDIKIQMYFEWSDGTPVTFTKWLPGEPSHENNRQEDC VVMKGKDGYWADRACEQPLGYICKMVSQIHTVIPEGAE KGCRKGWKRHGFYCYLIGSTLSTFADANQTCTNEKAYLT TVEDRYEQAFLTSLVGLRPEKYFWTGLSDVQNKGTFRW TVDEQVQFTHWNADMPGRKAGCVAMKTGVAGGLWDV LSCEEKAKFVCKHWAEGVTRPPEPTTTPEPKCPEDWGTT SKTSMCFKLYAKGKHEKKTWFESRDFCKAIGGELASIKS KDEQQVIWRLITSSGSYHELFWLGLTYGSPSEGFTWSDGS PVSYENWAYGEPNNYQNVEYCGELKGDPGMSWNDINCE HLNNWICQIQKGKTLLPEPTPAPQDNPPVTADGWVIYKD YQYYFSKEKETMDNARAFCKKNFGDLATIKSESEKKFLW KYINKNGGQSPYFIGLLISLDKKFIWMDGSKVDFVAWAT GEPNFANDDENCVTMYTNSGFWNDINCGYPNNFICQRH NSSINATAMPTTPPTPGGCKEGWHLYNNKCFKIFGFAEEE KKTWKEARKACIGLKGNLVSIENAKEQAFVTYHMRDSTF NAWTGLNDVNSEHTFLWTDGRGVHYTNWGKGYPGGRR SSLSYEDVDCVVVIGGNSREAGTWMDSTCDSKQGYICQT QTDPSVPISPTTAPKDGFVKYGKSSYALMKLKSPWHEAE KYCKDRTSLLASILDPYSNAFAWMKMHPFNVPIWIALNS NLTNNEYTWTDKWRVRYTNWGTDEPKLKSACVYMDVD GYWKTSYCNESFYFLCKKSDEIPATEPPQLPGKCPESEQT AWIPFHGHCYYIESSFTRSWGQASLECLRMGASLVSIETA |

TABLE 11-continued

Amino acid sequences of human and mouse macrophage mannose receptor

| Name | SEQ ID NO | Amino acid sequence |
|---|---|---|
| | | AESSFLSYRVEPLKSKTNFWIGMFRNVEGKWLWLNDNP<br>VSFVNWKTGDPSGERNDCVVLSSSSGLWNNIHCTSYKGF<br>ICKMPKIIDPVTTHSSITTKADQRKMDPQPKGSSKAAGVV<br>IVVLLIVIGAGVAAYFFYKKRRVLHIPQEATFENTLYFNSN<br>PSPGTSDTKDLVGNIEQNEHAVI |
| Rabbit Full-length *Oryctolagus cuniculus* MRC1 (NCBI Reference Sequence: XP_002717402.1) | 148 | MKPSLLLAFVSVIPAAVQLLDTRQFLIYNEDHKRCVEAIS<br>SSAVQTAVCNPDAESQRFRWVSEFHVMSVAFKLCLGVPS<br>KTDWVSVTLYNCDSKSEFQKWECKNDTLFGIKGEDLFFN<br>YGNRQEKNIMLYKGSGLWSRWKIYGTTDDLCSRGYEAM<br>YTLLGNANGATCAFPPKFQNKWYADCTSAGRSDGWLW<br>CGTTTDYDADKLFGFCPVKFEGSESLWNKDPLTSISYQIN<br>SKSALTWHQARKSCQQQNAELLSITEIHEQTYLTGLTSSL<br>TSGLWIGLNSLSFNSGWQWSGGSPFFRYLNWLPGSPSAEP<br>GKSCVSLNPGKNAKWENLECVQKLGYICKKGNTSLNSFV<br>IPSESDVPTNCPSQWWPYAGHCYRIHREEKKIQKDALIAC<br>RKEGGDLASIHSIEEFDFIISQLGYEPNDELWIGLNDIKIQM<br>YFEWSDGTPVTFTKWFRGEPSHENNRQEDCVVMKGKDG<br>YWADRACERPLNYICKMTSRTQATGIVEVETGCRKGWK<br>RHGFYCYLIGHTLSTFTEANQTCESEKAYLTTVEDRYEQA<br>FLTSLIGLRPEKYFWTGLSDIQNKGTFQWTIEEEVQFTHW<br>NSDMPGRKAGCVAMRTGIAGGLWDILKCDEKAKFVCKH<br>WAEGVTRPPEPTTTPEPRCPEDWGTSSKTSLCFKLFAKGK<br>HEKKTWFESRDFCRAVGGELASINNKEEQQIIWRLITAGG<br>SYHELFWLGLTYGSPSEGFTWSDGSPVSYENWAYGEPNN<br>YQNVEFCGELKADPGMSWNDINCEHLNNWICQIQKGQT<br>LKPEPTPAPQDNPPVTEDGWVIYKDYQYYFSKEKETMDN<br>ARAFCKRNFGDLVSIKSESEKKFLWKYVNRNDAQTAYFI<br>GLLVSLDKKFAWMDGSKVDYVSWATGEPNFANEDENC<br>VTMYANSGFWNDINCGYPNAFICQRHNSSINATVMPTVP<br>PGPRGCKEGWNFYNNKCFKIFGFVEEEKKNWQDARKAC<br>IGFGGNLVSIHNEKEQAFLIYHMKDSTFNAWTGLNDVNS<br>EHTFLWTDGRGVHYTNWGKGFPGGRRSSLSYEDADCVV<br>IIGGKSRDAGKWMDDTCDSKQGYICQTPSDPSLPSSRTTV<br>PTDGFIRYGKSSYSLMKLKLQWHEADKYCKDDTSLIASIL<br>DPYSNAFVWMQMQTFNVPVWIALNSNLTNNEYVWTDR<br>WRVRYTNWAPDEPKLKSACVYLDLDGYWKTAYCNESF<br>YFLCKRSDEIPATEPPQLPGRCPESEHTAWIPFHGHCYYIE<br>SSYTRNWGQASLECLRMGSSLVSIESASESSFLSYRVEPL<br>KSKTNFWIGMFRNVEGMWLWVNNNPVSFVNWNTGDPS<br>GERNDCVLLDASSGLWNNIHCSSYKGYICKRPKIVDAEPT<br>QTEVTTKADSRKDAPSKKSSSMAGVVIIVTLLILTGAGFA<br>AYFFYKKRRVHIPQEGTFENTLYFNSRSSPGTSDTKDLMG<br>NIEQNEHAVI |

---

The invention claimed is:

1. A method of imaging a cardiovascular disease in a subject, wherein the cardiovascular disease is atherosclerosis, the method comprising:

administering an anti-macrophage mannose receptor (anti-MMR) immunoglobulin single variable domain to the subject, wherein the anti-MMR immunoglobulin single variable domain is coupled to a detectable label, and medical imaging the anti-MMR immunoglobulin single variable domain coupled to a detectable label in the subject so as to image an atherosclerotic plaque in the subject.

2. The method according to claim 1, wherein said detectable label is a radionuclide.

3. The method according to claim 1, wherein the anti-MMR immunoglobulin single variable domain is a contrast agent in non-invasive in vivo medical imaging.

4. The method according to claim 1, the method further comprising:
targeting at least one atherosclerotic plaque in the subject with appropriate therapy.

5. The method according to claim 1, wherein the subject is post-infarction.

6. The method according to claim 1, wherein the anti-MMR immunoglobulin single variable domain comprises a peptide comprising four (4) framework regions (FR) and three (3) complementarity determining regions (CDR) according to the following formula (1):

FR1-CDR1-FR2-CDR2-FR3-CDR3-FR4     (1).

7. The method according to claim 1, wherein the anti-MMR immunoglobulin single variable domain is derived from a camelid antibody.

8. The method according to claim 1, wherein the anti-MMR immunoglobulin single variable domain comprises a single-domain antibody sequence.

9. A method of diagnosing or prognosing a cardiovascular disease, wherein the cardiovascular disease is atherosclerosis, the method comprising:
administering to a subject having atherosclerosis an anti-macrophage mannose receptor (anti-MMR) immunoglobulin single variable domain,
wherein the anti-MMR immunoglobulin single variable domain is labeled with a detectable label, and then
medical imaging the anti-MMR immunoglobulin single variable domain coupled to a detectable label in the subject so as to image an atherosclerotic plaque in the subject,
wherein the atherosclerosis is diagnosed or prognosed.

10. The method of claim 9, wherein the anti-MMR immunoglobulin single variable domain is administered to the subject post-infarction.

11. The method according to claim 9, wherein the subject is mammalian.

12. A method of in vivo imaging an atherosclerotic plaque in a subject with atherosclerosis, the method comprising:
administering to the subject an anti-macrophage mannose receptor (anti-MMR) immunoglobulin single variable domain, wherein the anti-MMR immunoglobulin single variable domain is labeled with a detectable label, and
imaging the labeled anti-MMR immunoglobulin single variable domain so as to image the atherosclerotic plaque in the subject.

* * * * *

SEQUENCE LISTING

<160> NUMBER OF SEQ ID NOS: 170

<210> SEQ ID NO 1
<211> LENGTH: 125
<212> TYPE: PRT
<213> ORGANISM: Vicugna pacos

<400> SEQUENCE: 1

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60
```

```
Gly Arg Phe Ser Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asn Thr Tyr Ser Asp Ser Asp Val Tyr Gly Tyr Trp Gly Gln Gly
                100                 105                 110

Thr Gln Val Thr Val Ser Ser His His His His His His
            115                 120                 125

<210> SEQ ID NO 2
<211> LENGTH: 119
<212> TYPE: PRT
<213> ORGANISM: Vicugna pacos

<400> SEQUENCE: 2

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Asn Ile Phe Ser Ile Asn
                 20                  25                  30

Ala Ile Gly Trp Tyr Arg Gln Ala Pro Gly Lys Gln Arg Glu Leu Val
             35                  40                  45

Ala Thr Ile Thr Leu Ser Gly Ser Thr Asn Tyr Ala Asp Ser Val Lys
         50                  55                  60

Gly Arg Phe Ser Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asn Thr Tyr Ser Asp Ser Asp Val Tyr Gly Tyr Trp Gly Gln Gly
                100                 105                 110

Thr Gln Val Thr Val Ser Ser
            115

<210> SEQ ID NO 3
<211> LENGTH: 130
<212> TYPE: PRT
<213> ORGANISM: Vicugna pacos

<400> SEQUENCE: 3

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Arg Thr Phe Ser Arg Asp
                 20                  25                  30

Ala Met Gly Trp Phe Arg Gln Ala Pro Gly Lys Glu Arg Glu Phe Val
             35                  40                  45

Ala Gly Ile Ser Trp Ser Gly Ser Thr Tyr Tyr Ala Asp Ser Val
         50                  55                  60

Lys Gly Arg Phe Thr Ile Ser Arg Asp Gly Ala Lys Asn Thr Val Asn
 65                  70                  75                  80

Leu Gln Met Asn Ser Leu Lys Pro Glu Asp Thr Ala Val Tyr Tyr Cys
                 85                  90                  95

Ala Ala Ser Ser Ile Tyr Gly Ser Ala Val Val Asp Gly Leu Tyr Asp
                100                 105                 110

Tyr Trp Gly Gln Gly Thr Gln Val Thr Val Ser Ser His His His His
            115                 120                 125

His His
    130
```

<210> SEQ ID NO 4
<211> LENGTH: 124
<212> TYPE: PRT
<213> ORGANISM: Vicugna pacos

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Ala Met Gly Trp Phe Arg Gln Ala Pro Gly Lys Glu Arg Glu Phe Val
        35                  40                  45

Ala Gly Ile Ser Trp Ser Gly Ser Thr Tyr Tyr Ala Asp Ser Val
    50                  55                  60

Lys Gly Arg Phe Thr Ile Ser Arg Asp Gly Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Ser Ile Tyr Gly Ser Ala Val Val Asp Gly Leu Tyr Asp
            100                 105                 110

Tyr Trp Gly Gln Gly Thr Gln Val Thr Val Ser Ser
        115                 120

<210> SEQ ID NO 5
<211> LENGTH: 260
<212> TYPE: PRT
<213> ORGANISM: Vicugna pacos

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Ser Ser Pro Ser Thr Pro Pro Thr Pro Ser
        115                 120                 125

Pro Ser Thr Pro Pro Ala Ser Gln Val Gln Leu Gln Glu Ser Gly Gly
    130                 135                 140

Gly Leu Val Gln Pro Gly Gly Ser Leu Arg Leu Ser Cys Ala Ala Ser
145                 150                 155                 160

Gly Asn Ile Phe Ser Ile Asn Ala Ile Gly Trp Tyr Arg Gln Ala Pro
                165                 170                 175

Gly Lys Gln Arg Glu Leu Val Ala Thr Ile Thr Leu Ser Gly Ser Thr
            180                 185                 190

Asn Tyr Ala Asp Ser Val Lys Gly Arg Phe Ser Ile Ser Arg Asp Asn
        195                 200                 205

```
Ala Lys Asn Thr Val Tyr Leu Gln Met Asn Ser Leu Lys Pro Glu Asp
    210                 215                 220

Thr Ala Val Tyr Tyr Cys Asn Ala Asn Thr Tyr Ser Asp Ser Asp Val
225                 230                 235                 240

Tyr Gly Tyr Trp Gly Gln Gly Thr Gln Val Thr Val Ser Ser His His
                245                 250                 255

His His His His
        260

<210> SEQ ID NO 6
<211> LENGTH: 259
<212> TYPE: PRT
<213> ORGANISM: Vicugna pacos

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Gly Gly Gly Gly Ser Gly Gly Gly Gly
        115                 120                 125

Ser Gly Gly Gly Gly Ser Gln Val Gln Leu Gln Glu Ser Gly Gly Gly
    130                 135                 140

Leu Val Gln Pro Gly Gly Ser Leu Arg Leu Ser Cys Ala Ala Ser Gly
145                 150                 155                 160

Asn Ile Phe Ser Ile Asn Ala Ile Gly Trp Tyr Arg Gln Ala Pro Gly
                165                 170                 175

Lys Gln Arg Glu Leu Val Ala Thr Ile Thr Leu Ser Gly Ser Thr Asn
            180                 185                 190

Tyr Ala Asp Ser Val Lys Gly Arg Phe Ser Ile Ser Arg Asp Asn Ala
        195                 200                 205

Lys Asn Thr Val Tyr Leu Gln Met Asn Ser Leu Lys Pro Glu Asp Thr
    210                 215                 220

Ala Val Tyr Tyr Cys Asn Ala Asn Thr Tyr Ser Asp Ser Asp Val Tyr
225                 230                 235                 240

Gly Tyr Trp Gly Gln Gly Thr Gln Val Thr Val Ser Ser His His His
                245                 250                 255

His His His

<210> SEQ ID NO 7
<211> LENGTH: 261
<212> TYPE: PRT
<213> ORGANISM: Vicugna pacos

<400> SEQUENCE: 7

Gln Val Gln Leu Gln Glu Ser Gly Gly Gly Leu Val Gln Pro Gly Gly
```

Ser Leu Arg Leu Ser Cys Ala Ala Ser Gly Asn Ile Phe Ser Ile Asn
                20                  25                  30

Ala Ile Gly Trp Tyr Arg Gln Ala Pro Gly Lys Gln Arg Glu Leu Val
            35                  40                  45

Ala Thr Ile Thr Leu Ser Ser Thr Asn Tyr Ala Asp Ser Val Lys
        50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
                100                 105                 110

Thr Gln Val Thr Val Ser Ser Ala His His Ser Glu Asp Pro Ser Ser
                115                 120                 125

Lys Ala Pro Lys Ala Pro Met Ala Gln Val Gln Leu Gln Glu Ser Gly
    130                 135                 140

Gly Gly Leu Val Gln Pro Gly Gly Ser Leu Arg Leu Ser Cys Ala Ala
145                 150                 155                 160

Ser Gly Asn Ile Phe Ser Ile Asn Ala Ile Gly Trp Tyr Arg Gln Ala
                165                 170                 175

Pro Gly Lys Gln Arg Glu Leu Val Ala Thr Ile Thr Leu Ser Gly Ser
            180                 185                 190

Thr Asn Tyr Ala Asp Ser Val Lys Gly Arg Phe Ser Ile Ser Arg Asp
        195                 200                 205

Asn Ala Lys Asn Thr Val Tyr Leu Gln Met Asn Ser Leu Lys Pro Glu
    210                 215                 220

Asp Thr Ala Val Tyr Tyr Cys Asn Ala Asn Thr Tyr Ser Asp Ser Asp
225                 230                 235                 240

Val Tyr Gly Tyr Trp Gly Gln Gly Thr Gln Val Thr Val Ser Ser His
                245                 250                 255

His His His His His
        260

<210> SEQ ID NO 8
<211> LENGTH: 133
<212> TYPE: PRT
<213> ORGANISM: Vicugna pacos

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
                20                  25                  30

Thr Val Ala Trp Phe Arg Gln Ala Pro Gly Lys Glu Arg Glu Gly Val
            35                  40                  45

Ser Cys Ile Ser Ser Ser Gly Gly Ser Thr Asn Tyr Ala Asp Ser Val
        50                  55                  60

Lys Gly Arg Phe Thr Ile Ser Arg Asp Asn Ser Lys Lys Ser Val Tyr
65                  70                  75                  80

Leu Gln Met Asn Ser Leu Lys Pro Glu Asp Thr Ala Ile Tyr Thr Cys
                85                  90                  95

Ala Ala Glu Arg Ala Pro Pro Tyr Tyr Ser Gly Tyr Tyr Phe Phe Asp
                100                 105                 110

```
Ser Thr Cys Val Ala Ala Ser Tyr Asp Tyr Trp Gly Gln Gly Thr Gln
            115                 120                 125

Val Thr Val Ser Ser
    130

<210> SEQ ID NO 9
<211> LENGTH: 121
<212> TYPE: PRT
<213> ORGANISM: Vicugna pacos

<400> SEQUENCE: 9

Gln Val Gln Leu Gln Glu Ser Gly Gly Gly Leu Val Gln Pro Gly Gly
1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Gly Val Val Ala Trp Asp Gln Pro Tyr Asp Asn Tyr Trp Gly
            100                 105                 110

Gln Gly Thr Gln Val Thr Val Ser Ser
        115                 120

<210> SEQ ID NO 10
<211> LENGTH: 125
<212> TYPE: PRT
<213> ORGANISM: Vicugna pacos

<400> SEQUENCE: 10

Gln Val Gln Leu Gln Glu Ser Gly Gly Gly Leu Val Gln Ala Gly Asp
1               5                   10                  15

Ser Leu Ser Ile Ser Cys Ala Ala Ser Gly Asp Thr Phe Asn His Tyr
            20                  25                  30

Ser Trp Gly Trp Phe Arg Gln Ala Pro Gly Lys Ala Arg Glu Phe Val
        35                  40                  45

Ala Ala Ile Ser Trp Asn Gly Gly Ser Lys Tyr Ala Asp Ser Val Lys
    50                  55                  60

Gly Arg Phe Ala Ile Ser Arg Asp Ile Ala Lys Asn Thr Val Ser Leu
65                  70                  75                  80

Gln Met Asn Ser Leu Glu Pro Glu Asp Thr Ala Val Tyr Tyr Cys Ala
                85                  90                  95

Ala Asp Arg Arg Pro Tyr Asn Asp Trp Asp Asp Trp Ser Trp Trp
            100                 105                 110

Val Tyr Trp Gly Gln Gly Thr Gln Val Thr Val Ser Ser
            115                 120                 125

<210> SEQ ID NO 11
<211> LENGTH: 127
<212> TYPE: PRT
<213> ORGANISM: Vicugna pacos

<400> SEQUENCE: 11

Gln Val Gln Leu Gln Glu Ser Gly Gly Gly Leu Val Gln Pro Gly Glu
```

```
               1               5                  10                 15
Ser Leu Arg Leu Ser Cys Lys Leu Ser Gly Phe Thr Leu Asp Tyr Tyr
                20                  25                 30
Asp Ile Gly Trp Phe Arg Gln Ala Pro Gly Lys Glu Arg Glu Gly Val
            35                  40                 45
Ser Cys Ile Ser Ser Ile Gly Ser Ala Asn Tyr Ala Asp Ser Val
        50                  55                 60
Lys Gly Arg Phe Thr Ile Ser Arg Asp Asn Val Lys Asn Thr Val Tyr
 65                 70                  75                 80
Leu Gln Met Asn Ser Leu Lys Pro Glu Asp Thr Ala Ile Tyr Tyr Cys
                85                  90                 95
Ala Ala Glu Ala Gln Thr Pro Tyr Asn Asp Gly Asp Cys Thr Arg Ala
            100                 105                110
Ser Tyr Asp Tyr Trp Gly Gln Gly Ile Gln Val Thr Val Ser Ser
        115                 120                125

<210> SEQ ID NO 12
<211> LENGTH: 118
<212> TYPE: PRT
<213> ORGANISM: Vicugna pacos

<400> SEQUENCE: 12

Gln Val Gln Leu Gln Glu Ser Gly Gly Gly Leu Val Gln Pro Gly Gly
 1               5                  10                 15
Ser Leu Arg Leu Ser Cys Ala Ala Ser Gly Phe Thr Leu Asp Tyr Tyr
                20                  25                 30
Ala Ile Gly Trp Phe Arg Gln Ala Pro Gly Lys Glu Arg Glu Gly Ile
            35                  40                 45
Ser Cys Ile Ser Tyr Lys Gly Gly Ser Thr Thr Tyr Ala Asp Ser Val
        50                  55                 60
Lys Gly Arg Phe Thr Ile Ser Lys Asp Asn Ala Lys Asn Thr Ala Tyr
 65                 70                  75                 80
Leu Gln Met Asn Asn Leu Lys Pro Glu Asp Thr Gly Ile Tyr Tyr Cys
                85                  90                 95
Ala Ala Gly Phe Val Cys Tyr Asn Tyr Asp Tyr Trp Gly Pro Gly Thr
            100                 105                110
Gln Val Thr Val Ser Ser
        115

<210> SEQ ID NO 13
<211> LENGTH: 131
<212> TYPE: PRT
<213> ORGANISM: Vicugna pacos

<400> SEQUENCE: 13

Gln Val Gln Leu Gln Glu Ser Gly Gly Gly Leu Val Gln Ala Gly Gly
 1               5                  10                 15
Ser Leu Arg Leu Ser Cys Ala Ala Ser Gly Phe Thr Asp Asp Asp Tyr
                20                  25                 30
Asp Ile Gly Trp Phe Arg Gln Ala Pro Gly Lys Glu Arg Glu Gly Val
            35                  40                 45
Ser Cys Ile Ser Ser Ser Asp Gly Ser Thr Tyr Tyr Ala Asp Ser Val
        50                  55                 60
Lys Gly Arg Phe Thr Ile Ser Ser Asp Asn Ala Lys Asn Thr Val Tyr
 65                 70                  75                 80
Leu Gln Met Asn Ser Leu Lys Pro Glu Asp Thr Ala Val Tyr Tyr Cys
```

```
                     85                  90                  95

Ala Ala Asp Phe Phe Arg Trp Asp Ser Gly Ser Tyr Tyr Val Arg Gly
                100                 105                 110

Cys Arg His Ala Thr Tyr Asp Tyr Trp Gly Gln Gly Thr Gln Val Thr
            115                 120                 125

Val Ser Ser
    130

<210> SEQ ID NO 14
<211> LENGTH: 119
<212> TYPE: PRT
<213> ORGANISM: Vicugna pacos

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Val Val Ser Gly Ser Phe Leu Ser Ile Asn
            20                  25                  30

His Met Gly Trp Tyr Arg Gln Val Ser Gly Glu Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ala Leu Thr Met Leu Pro Pro Phe Asp Phe Trp Gly Gln Gly
                100                 105                 110

Thr Gln Val Thr Val Ser Ser
        115

<210> SEQ ID NO 15
<211> LENGTH: 120
<212> TYPE: PRT
<213> ORGANISM: Vicugna pacos

<400> SEQUENCE: 15

Gln Val Gln Leu Gln Glu Ser Gly Gly Gly Leu Val Gln Pro Gly Gly
1               5                   10                  15

Ser Leu Met Leu Ser Cys Ala Ala Ser Gly Asn Ile Phe Thr Ile Asn
            20                  25                  30

Arg Met Gly Trp Tyr Arg Gln Ala Pro Gly Lys Gln Arg Glu Leu Val
        35                  40                  45

Ala Ala Ile Thr Ser Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Ile Val Thr Met Thr Ser Pro Tyr Ser Asp Tyr Trp Gly Gln
                100                 105                 110

Gly Thr Gln Val Thr Val Ser Ser
        115                 120

<210> SEQ ID NO 16
<211> LENGTH: 112
<212> TYPE: PRT
```

```
<213> ORGANISM: Vicugna pacos

<400> SEQUENCE: 16

Gln Val Gln Leu Gln Glu Ser Gly Gly Thr Leu Val Gln Pro Gly Gly
1               5                   10                  15

Ser Leu Arg Leu Ser Cys Ala Ala Ser Gly Ser Thr Phe Ser Ile Asn
            20                  25                  30

Asn Met Gly Trp Tyr Arg Gln Ala Pro Gly Lys Gln Arg Glu Leu Val
        35                  40                  45

Ala Gly Ile Thr Gly Gly Asn Thr His Tyr Ala Asp Ser Val Lys Gly
    50                  55                  60

Arg Phe Thr Ile Ser Arg Asp Asn Ala Lys Asn Thr Met Tyr Leu Gln
65                  70                  75                  80

Met Asn Gly Leu Lys Pro Glu Asp Thr Ala Val Tyr Tyr Cys Asn Ala
                85                  90                  95

Asn Trp Gly Ala Tyr Trp Gly Gln Gly Thr Gln Val Thr Val Ser Ser
            100                 105                 110

<210> SEQ ID NO 17
<211> LENGTH: 121
<212> TYPE: PRT
<213> ORGANISM: Vicugna pacos

<400> SEQUENCE: 17

Gln Val Gln Leu Gln Glu Ser Gly Gly Gly Leu Val Gln Pro Gly Gly
1               5                   10                  15

Ser Leu Gly Leu Ser Cys Ala Ala Ser Gly Arg Ile Ala Ser Ile Ser
            20                  25                  30

Ala Met Gly Trp Tyr Arg Gln Ala Pro Gly Lys Gln Arg Glu Leu Val
        35                  40                  45

Ala Ala Ile Thr Gly Ser Gly Arg Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Leu Met Val Asp Tyr Gly Leu Gly Leu Gly Thr Asp Tyr Trp Gly
            100                 105                 110

Gln Gly Thr Gln Val Thr Val Ser Ser
            115                 120

<210> SEQ ID NO 18
<211> LENGTH: 130
<212> TYPE: PRT
<213> ORGANISM: Vicugna pacos

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Ala Ser Gly Pro Gly Phe Lys Leu Asp
            20                  25                  30

Tyr Tyr Ala Ile Ala Trp Phe Arg Gln Ala Pro Gly Lys Glu Arg Glu
        35                  40                  45

Gly Val Ser Cys Ile Gly Gly Ser Gly Ser Leu Thr Thr Tyr Val
    50                  55                  60

Glu Asn Ser Val Lys Asp Arg Phe Thr Ile Ser Arg Asp Asn Ala Gln
65                  70                  75                  80
```

-continued

Asn Thr Val Tyr Leu His Met Asn Ser Leu Lys Pro Glu Asp Thr Gly
                85                  90                  95

Ile Tyr Tyr Cys Ala Ala Asp Thr Tyr Tyr Cys Ser Lys Arg Val
            100                 105                 110

Trp Arg Asn Asp Tyr Gly Ser Trp Gly Gln Gly Thr Gln Val Thr Val
        115                 120                 125

Ser Ser
    130

<210> SEQ ID NO 19
<211> LENGTH: 122
<212> TYPE: PRT
<213> ORGANISM: Vicugna pacos

<400> SEQUENCE: 19

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
            20                  25                  30

Tyr Met Gly Trp Tyr Arg Gln Ala Pro Gly Lys Gln Arg Glu Leu Val
        35                  40                  45

Ala Ala Ile Thr Ser Gly Ser Gly Ser Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Asp Met Asp Ser Ser Leu Ser Gly Gly Tyr Val Asp Val Trp
            100                 105                 110

Gly Gln Gly Thr Gln Val Thr Val Ser Ser
        115                 120

<210> SEQ ID NO 20
<211> LENGTH: 125
<212> TYPE: PRT
<213> ORGANISM: Vicugna pacos

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Thr Phe Asp Asp Ser
            20                  25                  30

Val Ile Gly Trp Phe Arg Gln Ala Pro Gly Lys Glu Arg Glu Gly Val
        35                  40                  45

Ser Cys Ile Ser Ser Asn Asp Gly Thr Thr His Tyr Ala Ser Pro Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Thr Pro Ser Ile Gly Ser Pro Cys Thr Ser Ala Ser Tyr
            100                 105                 110

Asp Tyr Trp Gly Gln Gly Thr Gln Val Thr Val Ser Ser
        115                 120                 125

<210> SEQ ID NO 21

```
<211> LENGTH: 125
<212> TYPE: PRT
<213> ORGANISM: Vicugna pacos

<400> SEQUENCE: 21

Gln Val Gln Leu Gln Glu Ser Gly Gly Gly Leu Val Gln Pro Gly Gly
1               5                   10                  15

Ser Leu Arg Leu Ser Cys Thr Ala Thr Gly Phe Thr Leu Lys Asn His
            20                  25                  30

His Ile Gly Trp Leu Arg Gln Ala Pro Gly Lys Glu Arg Glu Gly Val
        35                  40                  45

Ala Ser Ile Asn Ser Ser Gly Gly Ser Thr Asn Tyr Ala Asp Ser Val
    50                  55                  60

Gln Gly Arg Phe Thr Ile Ser Arg Asp Asn Ala Lys Asn Thr Val Phe
65                  70                  75                  80

Leu Gln Met Asn Ser Leu Lys Ser Glu Asp Thr Ala Val Tyr Tyr Cys
                85                  90                  95

Ala Arg Leu Arg Arg Tyr Tyr Gly Leu Asn Leu Asp Pro Gly Ser Tyr
            100                 105                 110

Asp Tyr Trp Gly Gln Gly Thr Gln Val Thr Val Ser Ser
        115                 120                 125

<210> SEQ ID NO 22
<211> LENGTH: 124
<212> TYPE: PRT
<213> ORGANISM: Vicugna pacos

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ala Tyr
            20                  25                  30

Ala Met Gly Trp Phe Arg Gln Ala Pro Gly Lys Glu Arg Glu Phe Val
        35                  40                  45

Ala Ala Ile Ser Arg Ser Gly Asp Ser Thr Asp Tyr Ala Asp Ser Val
    50                  55                  60

Lys Gly Arg Phe Thr Ile Ser Arg Asp Ser Ala Lys Asn Met Val Tyr
65                  70                  75                  80

Leu Gln Met Asn Ser Leu Lys Pro Glu Asp Thr Ala Leu Tyr His Cys
                85                  90                  95

Ala Ala Arg Thr Val Ser Ala Pro Pro Ser Ala Ala Trp Gly Tyr Gly
            100                 105                 110

Tyr Trp Gly Gln Gly Thr Gln Val Thr Val Ser Ser
        115                 120

<210> SEQ ID NO 23
<211> LENGTH: 118
<212> TYPE: PRT
<213> ORGANISM: Vicugna pacos

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Tyr
            20                  25                  30

Ala Ile Gly Trp Phe Arg Gln Ala Pro Gly Lys Glu Arg Glu Gly Ile
        35                  40                  45
```

```
Ser Cys Ile Ser Tyr Lys Gly Gly Ser Thr Thr Tyr Ala Asp Ser Val
    50                  55                  60

Lys Gly Arg Phe Thr Ile Ser Lys Asp Asn Ala Lys Asn Thr Ala Tyr
65                  70                  75                  80

Leu Gln Met Asn Ser Leu Lys Pro Glu Asp Thr Gly Ile Tyr Ser Cys
                    85                  90                  95

Ala Ala Gly Phe Val Cys Tyr Asn Tyr Asp Tyr Trp Gly Gln Gly Thr
                100                 105                 110

Gln Val Thr Val Ser Ser
            115
```

<210> SEQ ID NO 24
<211> LENGTH: 130
<212> TYPE: PRT
<213> ORGANISM: Vicugna pacos

<400> SEQUENCE: 24

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
            20                  25                  30

Val Asn Tyr Ala Met Gly Trp Phe Arg Gln Phe Pro Gly Lys Glu Arg
            35                  40                  45

Glu Phe Val Ala Ser Ile Ser Trp Ser Ser Val Thr Thr Tyr Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala His Leu Ala Gln Tyr Ser Asp Tyr Ala Tyr Arg
                100                 105                 110

Asp Pro His Gln Phe Gly Ala Trp Gly Gln Gly Thr Gln Val Thr Val
            115                 120                 125

Ser Ser
    130
```

<210> SEQ ID NO 25
<211> LENGTH: 117
<212> TYPE: PRT
<213> ORGANISM: Vicugna pacos

<400> SEQUENCE: 25

```
Gln Val Gln Leu Gln Glu Ser Gly Gly Gly Leu Val Gln Ala Gly Gly
1               5                   10                  15

Ser Leu Arg Leu Ser Cys Leu Ala Ser Gly Asp Thr Phe Ser Asn Tyr
            20                  25                  30

Val Met Ala Trp Phe Arg Gln Ala Pro Gly Lys Glu Arg Glu Ile Val
            35                  40                  45

Ala Ala Ile Arg Leu Ser Gly Ala Arg Tyr Val Pro Asp Ser Val Lys
    50                  55                  60

Gly Arg Phe Thr Ile Ser Arg Asp Asn Ala Lys Asn Ala Met Tyr Leu
65                  70                  75                  80

Gln Met Thr Ser Leu Lys Pro Glu Asp Thr Ala Arg Tyr Tyr Cys Ala
                85                  90                  95

Ala Gly His Thr Trp Gly Gln Tyr Ala Tyr Trp Gly Gln Gly Thr Gln
                100                 105                 110
```

```
Val Thr Val Ser Ser
        115

<210> SEQ ID NO 26
<211> LENGTH: 119
<212> TYPE: PRT
<213> ORGANISM: Vicugna pacos

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ala
            20                  25                  30

Ala Met Gly Trp Phe Arg Gln Ala Pro Gly Lys Glu Arg Glu Pro Val
        35                  40                  45

Ala Leu Ile Asn Leu Asp Asp Gly Glu Thr Tyr Tyr Ala Asp Ile Ala
    50                  55                  60

Lys Gly Arg Phe Thr Leu Ser Lys Asp Asn Ala Lys Asn Ser Val Tyr
65                  70                  75                  80

Leu Gln Met Asn Ser Leu Lys Pro Glu Asp Thr Ala Val Tyr Tyr Cys
                85                  90                  95

Ala Val Arg Gly Arg Phe Asp Asp Asn Tyr Glu Tyr Trp Gly Gln Gly
            100                 105                 110

Thr Gln Val Thr Val Ser Ser
        115

<210> SEQ ID NO 27
<211> LENGTH: 122
<212> TYPE: PRT
<213> ORGANISM: Vicugna pacos

<400> SEQUENCE: 27

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
            20                  25                  30

Tyr Met Gly Trp Tyr Arg Gln Ala Pro Gly Lys Gln Arg Glu Leu Val
        35                  40                  45

Ala Ala Ile Thr Ser Gly Ser Gly Ser Thr Asn Tyr Ala Asp Ser Val
    50                  55                  60

Lys Gly Arg Phe Thr Ile Ser Arg Asp Asn Ala Lys Lys Thr Met Tyr
65                  70                  75                  80

Leu Gln Met Asn Ser Leu Lys Pro Glu Asp Thr Ala Val Tyr Tyr Cys
                85                  90                  95

Asn Ala Asp Met Asp Ser Ser Leu Ser Gly Gly Tyr Val Asp Val Trp
            100                 105                 110

Gly Gln Gly Thr Gln Val Thr Val Ser Ser
        115                 120

<210> SEQ ID NO 28
<211> LENGTH: 112
<212> TYPE: PRT
<213> ORGANISM: Vicugna pacos

<400> SEQUENCE: 28

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Asn
```

```
                20                  25                  30
Asn Met Gly Trp Tyr Arg Gln Ala Pro Gly Lys Gln Arg Glu Leu Val
            35                  40                  45

Ala Gly Ile Thr Gly Gly Asn Thr His Tyr Ala Asp Ser Val Lys Gly
        50                  55                  60

Arg Phe Thr Ile Ser Arg Asp Asn Ala Lys Asn Thr Met Tyr Leu Gln
65                  70                  75                  80

Met Asn Ser Leu Lys Pro Glu Asp Thr Ala Val Tyr Tyr Cys Asn Ala
            85                  90                  95

Asn Trp Gly Ala Tyr Trp Gly Gln Gly Thr Gln Val Thr Val Ser Ser
            100                 105                 110
```

<210> SEQ ID NO 29
<211> LENGTH: 119
<212> TYPE: PRT
<213> ORGANISM: Vicugna pacos

<400> SEQUENCE: 29

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Val Ser Ile Asn
            20                  25                  30

Ala Met Gly Trp Tyr Arg Gln Ala Pro Gly Lys Gln Arg Glu Leu Val
            35                  40                  45

Ala Leu Val Thr Gly Ser Gly Arg Thr Asn Leu Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Val Leu Val Ile Gly Pro Leu Glu Gly Tyr Asp Tyr Trp Gly Gln Gly
            100                 105                 110

Thr Gln Val Thr Val Ser Ser
        115
```

<210> SEQ ID NO 30
<211> LENGTH: 121
<212> TYPE: PRT
<213> ORGANISM: Vicugna pacos

<400> SEQUENCE: 30

```
Gln Val Gln Leu Gln Glu Ser Gly Gly Gly Leu Val Gln Pro Gly Gly
1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
            35                  40                  45

Ala Ala Val Ser Ser Gly Gly Ser Thr Asn Tyr Ala Asp Ser Val Lys
        50                  55                  60

Gly Arg Phe Thr Ile Ser Arg Asp Asn Ala Lys Asn Ala Val Tyr Leu
65                  70                  75                  80

Gln Met Asn Ser Leu Lys Pro Glu Asp Thr Ala Val Tyr Tyr Cys Asn
            85                  90                  95

Ala Asp Gly Val Val Ala Trp Asp Gln Pro Tyr Asp Asn Tyr Trp Gly
            100                 105                 110

Gln Gly Thr Gln Val Thr Val Ser Ser
```

```
              115                 120
```

<210> SEQ ID NO 31
<211> LENGTH: 118
<212> TYPE: PRT
<213> ORGANISM: Vicugna pacos

<400> SEQUENCE: 31

```
Gln Val Gln Leu Gln Glu Ser Gly Gly Gly Leu Val Gln Ala Gly Gly
1               5                   10                  15

Ser Leu Arg Leu Ser Cys Val Asp Gln Gly Arg Thr Phe Ser Val Asn
            20                  25                  30

Ala Met Ala Trp Tyr Arg Gln Ala Pro Gly Lys Gln Arg Glu Leu Val
        35                  40                  45

Ala Ser Ile Thr Ser Ser Gly Leu Asp Thr Gln Tyr Ala Glu Gly Met
    50                  55                  60

Lys Gly Arg Phe Thr Ile Ser Lys Gly Asn Asp Lys Phe Ser Thr Tyr
65                  70                  75                  80

Leu Gln Met Asn Asn Leu Lys Pro Asp Asp Thr Ala Val Tyr Tyr Cys
                85                  90                  95

Asn Ala Glu Arg Trp Asp Asn Gly Met Val Tyr Trp Gly Lys Gly Thr
            100                 105                 110

Gln Val Thr Val Ser Ser
        115
```

<210> SEQ ID NO 32
<211> LENGTH: 132
<212> TYPE: PRT
<213> ORGANISM: Vicugna pacos

<400> SEQUENCE: 32

```
Gln Val Gln Leu Gln Glu Ser Gly Gly Gly Leu Val Gln Ala Gly Asp
1               5                   10                  15

Ser Leu Arg Leu Ser Cys Leu Ala Thr Gly Ser Met Phe Ser Ile Asn
            20                  25                  30

Ala Trp Gly Trp Tyr Arg Gln Ala Pro Gly Lys Gln Arg Glu Leu Val
        35                  40                  45

Ala Ser Ile Thr Ser Gly Gly Ser Thr Glu Tyr Ala Glu Ser Val
    50                  55                  60

Lys Gly Arg Phe Thr Ile Ser Arg Asp Ser Ala Lys Asn Met Leu Tyr
65                  70                  75                  80

Leu Gln Met Asn Ser Leu Arg Pro Glu Asp Thr Ala Val Tyr Tyr Cys
                85                  90                  95

Asn Ala Glu Arg Trp Asp Gly Tyr Ala Leu Gly Tyr Ser Pro Asn His
            100                 105                 110

Gly Ser Gly His Arg Pro Tyr Asn Tyr Trp Gly Gln Gly Thr Gln Val
        115                 120                 125

Thr Val Ser Ser
        130
```

<210> SEQ ID NO 33
<211> LENGTH: 120
<212> TYPE: PRT
<213> ORGANISM: Vicugna pacos

<400> SEQUENCE: 33

```
Gln Val Gln Leu Gln Glu Ser Gly Gly Gly Leu Val Gln Pro Gly Gly
1               5                   10                  15
```

Ser Leu Arg Leu Ser Cys Ala Ala Ser Gly Ser Ile Phe Ser Ile Asn
            20                  25                  30

Ala Trp Gly Trp Tyr Arg Gln Ala Pro Gly Lys Gln Arg Glu Leu Val
        35                  40                  45

Ala Glu Ile Thr Ser Ser Gly Ser Thr Asn Tyr Ala Asp Ser Val Lys
    50                  55                  60

Gly Arg Phe Thr Ile Ser Gly Asp Asn Ala Lys Asn Ser Val Tyr Leu
65                  70                  75                  80

His Met Asn Asn Leu Glu Pro Glu Asp Thr Ala Val Tyr Tyr Cys Lys
                85                  90                  95

Ala Val Ala Val Thr Phe Thr Thr Pro Arg Ser Asp Tyr Trp Gly Arg
            100                 105                 110

Gly Thr Gln Val Thr Val Ser Ser
            115                 120

<210> SEQ ID NO 34
<211> LENGTH: 116
<212> TYPE: PRT
<213> ORGANISM: Vicugna pacos

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Ala Pro Ser Gly Ser Ile Ile Ser Ile Asn
            20                  25                  30

Ala Met Ala Trp Tyr Arg Gln Ala Pro Gly Lys Glu Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Gly Asp Ile Ala Lys Asn Leu Leu Trp Leu
65                  70                  75                  80

Gln Met Asn Ser Leu Lys Pro Glu Asp Thr Ala Met Tyr Tyr Cys Ala
                85                  90                  95

Pro Gly Gly Gly Trp Arg Pro Gly Ala Trp Gly Gln Gly Thr Gln Val
            100                 105                 110

Thr Val Ser Ser
            115

<210> SEQ ID NO 35
<211> LENGTH: 116
<212> TYPE: PRT
<213> ORGANISM: Vicugna pacos

<400> SEQUENCE: 35

Gln Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Val Ser Thr Ser
            20                  25                  30

Met Ile Asn Trp Ala Arg Gln Val Pro Gly Lys Glu Leu Glu Trp Leu
        35                  40                  45

Val Asp Val Leu Pro Ser Gly Thr Tyr Tyr Ala Asp Pro Val Lys
    50                  55                  60

Gly Arg Phe Thr Ile Ser Arg Asp Asn Ala Gln Asn Thr Ile Tyr Leu
65                  70                  75                  80

Gln Met Asn Tyr Leu Lys Pro Glu Asp Thr Ala Ile Tyr Tyr Cys Ala
                85                  90                  95

Ile Asn Arg Glu Thr Met Pro Pro Phe Arg Gly Gln Gly Thr Gln Val
            100                 105                 110

Thr Val Ser Ser
        115

<210> SEQ ID NO 36
<211> LENGTH: 121
<212> TYPE: PRT
<213> ORGANISM: Vicugna pacos

<400> SEQUENCE: 36

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Pro Phe Ser Ser Ala
            20                  25                  30

Pro Met Ser Trp Val Arg Gln Ala Pro Gly Lys Glu Leu Glu Trp Val
        35                  40                  45

Ser Tyr Ile Gly Tyr Thr Gly Thr Ile Thr Asp Tyr Ala Asn Ser Val
    50                  55                  60

Lys Gly Arg Phe Thr Ile Ser Arg Asp Asn Ala Lys Asn Arg Leu Tyr
65                  70                  75                  80

Leu Gln Met Asn Ser Leu Lys Pro Glu Asp Thr Ala Val Tyr Phe Cys
                85                  90                  95

Ala Gln Gly Tyr Ala Arg Leu Ile Ala Asp Ser Asp Leu Val Arg Gly
            100                 105                 110

Gln Gly Thr Gln Val Thr Val Ser Ser
        115                 120

<210> SEQ ID NO 37
<211> LENGTH: 121
<212> TYPE: PRT
<213> ORGANISM: Vicugna pacos

<400> SEQUENCE: 37

Gln Val Gln Leu Gln Glu Ser Gly Gly Arg Leu Gly Ala Ala Gly Gly
1               5                   10                  15

Ser Leu Arg Leu Ser Cys Thr Ala Ser Gly Phe Pro Phe Asn Ile Tyr
            20                  25                  30

Pro Met Ser Trp Val Arg Gln Ala Pro Gly Lys Gly Phe Glu Trp Val
        35                  40                  45

Ser Tyr Ile Ser His Gly Gly Thr Thr Thr Asp Tyr Ser Asp Ala Val
    50                  55                  60

Lys Gly Arg Phe Thr Ile Ser Arg Asp Asn Ala Lys Asn Arg Leu Tyr
65                  70                  75                  80

Leu Gln Met Asp Ser Leu Lys Pro Glu Asp Thr Ala Val Tyr Phe Cys
                85                  90                  95

Ala Gln Gly Tyr Ala Arg Leu Met Thr Asp Ser Glu Leu Val Arg Gly
            100                 105                 110

Gln Gly Thr Gln Val Thr Val Ser Ser
        115                 120

<210> SEQ ID NO 38
<211> LENGTH: 11
<212> TYPE: PRT
<213> ORGANISM: Vicugna pacos

<400> SEQUENCE: 38

```
Ser Gly Asn Ile Phe Ser Ile Asn Ala Ile Gly
1               5                   10
```

<210> SEQ ID NO 39
<211> LENGTH: 11
<212> TYPE: PRT
<213> ORGANISM: Vicugna pacos

<400> SEQUENCE: 39

```
Ser Gly Arg Thr Phe Ser Arg Asp Ala Met Gly
1               5                   10
```

<210> SEQ ID NO 40
<211> LENGTH: 10
<212> TYPE: PRT
<213> ORGANISM: Vicugna pacos

<400> SEQUENCE: 40

```
Gly Phe Thr Leu Asp Asn Tyr Thr Val Ala
1               5                   10
```

<210> SEQ ID NO 41
<211> LENGTH: 10
<212> TYPE: PRT
<213> ORGANISM: Vicugna pacos

<400> SEQUENCE: 41

```
Gly Ser Ile Phe Ser Ile Lys Thr Met Gly
1               5                   10
```

<210> SEQ ID NO 42
<211> LENGTH: 10
<212> TYPE: PRT
<213> ORGANISM: Vicugna pacos

<400> SEQUENCE: 42

```
Gly Asp Thr Phe Asn His Tyr Ser Trp Gly
1               5                   10
```

<210> SEQ ID NO 43
<211> LENGTH: 10
<212> TYPE: PRT
<213> ORGANISM: Vicugna pacos

<400> SEQUENCE: 43

```
Gly Phe Thr Leu Asp Tyr Tyr Asp Ile Gly
1               5                   10
```

<210> SEQ ID NO 44
<211> LENGTH: 10
<212> TYPE: PRT
<213> ORGANISM: Vicugna pacos

<400> SEQUENCE: 44

```
Gly Phe Thr Leu Asp Tyr Tyr Ala Ile Gly
1               5                   10
```

<210> SEQ ID NO 45
<211> LENGTH: 10
<212> TYPE: PRT
<213> ORGANISM: Vicugna pacos

<400> SEQUENCE: 45

```
Gly Phe Thr Asp Asp Asp Tyr Asp Ile Gly
1               5                   10
```

```
<210> SEQ ID NO 46
<211> LENGTH: 10
<212> TYPE: PRT
<213> ORGANISM: Vicugna pacos

<400> SEQUENCE: 46

Gly Ser Phe Leu Ser Ile Asn His Met Gly
1               5                   10

<210> SEQ ID NO 47
<211> LENGTH: 10
<212> TYPE: PRT
<213> ORGANISM: Vicugna pacos

<400> SEQUENCE: 47

Gly Asn Ile Phe Thr Ile Asn Arg Met Gly
1               5                   10

<210> SEQ ID NO 48
<211> LENGTH: 10
<212> TYPE: PRT
<213> ORGANISM: Vicugna pacos

<400> SEQUENCE: 48

Gly Ser Thr Phe Ser Ile Asn Asn Met Gly
1               5                   10

<210> SEQ ID NO 49
<211> LENGTH: 10
<212> TYPE: PRT
<213> ORGANISM: Vicugna pacos

<400> SEQUENCE: 49

Gly Arg Ile Ala Ser Ile Ser Ala Met Gly
1               5                   10

<210> SEQ ID NO 50
<211> LENGTH: 11
<212> TYPE: PRT
<213> ORGANISM: Vicugna pacos

<400> SEQUENCE: 50

Pro Gly Phe Lys Leu Asp Tyr Tyr Ala Ile Ala
1               5                   10

<210> SEQ ID NO 51
<211> LENGTH: 10
<212> TYPE: PRT
<213> ORGANISM: Vicugna pacos

<400> SEQUENCE: 51

Gly Arg Thr Phe Ser Ile Asn Tyr Met Gly
1               5                   10

<210> SEQ ID NO 52
<211> LENGTH: 10
<212> TYPE: PRT
<213> ORGANISM: Vicugna pacos

<400> SEQUENCE: 52

Gly Gly Thr Phe Asp Asp Ser Val Ile Gly
1               5                   10
```

```
<210> SEQ ID NO 53
<211> LENGTH: 10
<212> TYPE: PRT
<213> ORGANISM: Vicugna pacos

<400> SEQUENCE: 53

Gly Phe Thr Leu Lys Asn His His Ile Gly
1               5                   10

<210> SEQ ID NO 54
<211> LENGTH: 10
<212> TYPE: PRT
<213> ORGANISM: Vicugna pacos

<400> SEQUENCE: 54

Gly Arg Ile Phe Ser Ala Tyr Ala Met Gly
1               5                   10

<210> SEQ ID NO 55
<211> LENGTH: 10
<212> TYPE: PRT
<213> ORGANISM: Vicugna pacos

<400> SEQUENCE: 55

Gly Phe Ser Leu Asp Tyr Tyr Ala Ile Gly
1               5                   10

<210> SEQ ID NO 56
<211> LENGTH: 13
<212> TYPE: PRT
<213> ORGANISM: Vicugna pacos

<400> SEQUENCE: 56

Gly Arg Thr Phe Ser Asn Tyr Val Asn Tyr Ala Met Gly
1               5                   10

<210> SEQ ID NO 57
<211> LENGTH: 10
<212> TYPE: PRT
<213> ORGANISM: Vicugna pacos

<400> SEQUENCE: 57

Gly Asp Thr Phe Ser Asn Tyr Val Met Ala
1               5                   10

<210> SEQ ID NO 58
<211> LENGTH: 10
<212> TYPE: PRT
<213> ORGANISM: Vicugna pacos

<400> SEQUENCE: 58

Gly Arg Thr Phe Ser Ser Ala Ala Met Gly
1               5                   10

<210> SEQ ID NO 59
<211> LENGTH: 10
<212> TYPE: PRT
<213> ORGANISM: Vicugna pacos

<400> SEQUENCE: 59

Gly Arg Thr Phe Ser Ile Asn Tyr Met Gly
1               5                   10

<210> SEQ ID NO 60
<211> LENGTH: 10
```

```
<212> TYPE: PRT
<213> ORGANISM: Vicugna pacos

<400> SEQUENCE: 60

Gly Ser Thr Phe Ser Ile Asn Asn Met Gly
1               5                   10

<210> SEQ ID NO 61
<211> LENGTH: 10
<212> TYPE: PRT
<213> ORGANISM: Vicugna pacos

<400> SEQUENCE: 61

Gly Ser Ile Val Ser Ile Asn Ala Met Gly
1               5                   10

<210> SEQ ID NO 62
<211> LENGTH: 10
<212> TYPE: PRT
<213> ORGANISM: Vicugna pacos

<400> SEQUENCE: 62

Gly Ser Ile Phe Ser Ile Lys Thr Met Gly
1               5                   10

<210> SEQ ID NO 63
<211> LENGTH: 10
<212> TYPE: PRT
<213> ORGANISM: Vicugna pacos

<400> SEQUENCE: 63

Gly Arg Thr Phe Ser Val Asn Ala Met Ala
1               5                   10

<210> SEQ ID NO 64
<211> LENGTH: 10
<212> TYPE: PRT
<213> ORGANISM: Vicugna pacos

<400> SEQUENCE: 64

Gly Ser Met Phe Ser Ile Asn Ala Trp Gly
1               5                   10

<210> SEQ ID NO 65
<211> LENGTH: 10
<212> TYPE: PRT
<213> ORGANISM: Vicugna pacos

<400> SEQUENCE: 65

Gly Ser Ile Phe Ser Ile Asn Ala Trp Gly
1               5                   10

<210> SEQ ID NO 66
<211> LENGTH: 10
<212> TYPE: PRT
<213> ORGANISM: Vicugna pacos

<400> SEQUENCE: 66

Gly Ser Ile Ile Ser Ile Asn Ala Met Ala
1               5                   10

<210> SEQ ID NO 67
<211> LENGTH: 10
<212> TYPE: PRT
<213> ORGANISM: Vicugna pacos
```

<400> SEQUENCE: 67

Gly Phe Thr Val Ser Thr Ser Met Ile Asn
1               5                   10

<210> SEQ ID NO 68
<211> LENGTH: 10
<212> TYPE: PRT
<213> ORGANISM: Vicugna pacos

<400> SEQUENCE: 68

Gly Phe Pro Phe Ser Ser Ala Pro Met Ser
1               5                   10

<210> SEQ ID NO 69
<211> LENGTH: 10
<212> TYPE: PRT
<213> ORGANISM: Vicugna pacos

<400> SEQUENCE: 69

Gly Phe Pro Phe Asn Ile Tyr Pro Met Ser
1               5                   10

<210> SEQ ID NO 70
<211> LENGTH: 9
<212> TYPE: PRT
<213> ORGANISM: Vicugna pacos

<400> SEQUENCE: 70

Thr Ile Thr Leu Ser Gly Ser Thr Asn
1               5

<210> SEQ ID NO 71
<211> LENGTH: 9
<212> TYPE: PRT
<213> ORGANISM: Vicugna pacos

<400> SEQUENCE: 71

Gly Ile Ser Trp Ser Gly Gly Ser Thr
1               5

<210> SEQ ID NO 72
<211> LENGTH: 9
<212> TYPE: PRT
<213> ORGANISM: Vicugna pacos

<400> SEQUENCE: 72

Cys Ile Ser Ser Ser Gly Gly Ser Thr
1               5

<210> SEQ ID NO 73
<211> LENGTH: 8
<212> TYPE: PRT
<213> ORGANISM: Vicugna pacos

<400> SEQUENCE: 73

Ala Ile Thr Ser Gly Gly Ser Thr
1               5

<210> SEQ ID NO 74
<211> LENGTH: 8
<212> TYPE: PRT
<213> ORGANISM: Vicugna pacos

<400> SEQUENCE: 74

Ala Ile Ser Trp Asn Gly Gly Ser
1               5

<210> SEQ ID NO 75
<211> LENGTH: 9
<212> TYPE: PRT
<213> ORGANISM: Vicugna pacos

<400> SEQUENCE: 75

Cys Ile Ser Ser Ile Gly Gly Ser Ala
1               5

<210> SEQ ID NO 76
<211> LENGTH: 9
<212> TYPE: PRT
<213> ORGANISM: Vicugna pacos

<400> SEQUENCE: 76

Cys Ile Ser Tyr Lys Gly Gly Ser Thr
1               5

<210> SEQ ID NO 77
<211> LENGTH: 9
<212> TYPE: PRT
<213> ORGANISM: Vicugna pacos

<400> SEQUENCE: 77

Cys Ile Ser Ser Ser Asp Gly Ser Thr
1               5

<210> SEQ ID NO 78
<211> LENGTH: 8
<212> TYPE: PRT
<213> ORGANISM: Vicugna pacos

<400> SEQUENCE: 78

Ala Ile Thr Ser Gly Gly Ser Thr
1               5

<210> SEQ ID NO 79
<211> LENGTH: 8
<212> TYPE: PRT
<213> ORGANISM: Vicugna pacos

<400> SEQUENCE: 79

Ala Ile Thr Ser Gly Gly Asn Thr
1               5

<210> SEQ ID NO 80
<211> LENGTH: 7
<212> TYPE: PRT
<213> ORGANISM: Vicugna pacos

<400> SEQUENCE: 80

Gly Ile Thr Gly Gly Asn Thr
1               5

<210> SEQ ID NO 81
<211> LENGTH: 8
<212> TYPE: PRT
<213> ORGANISM: Vicugna pacos

<400> SEQUENCE: 81

Ala Ile Thr Gly Ser Gly Arg Thr

```
<210> SEQ ID NO 82
<211> LENGTH: 10
<212> TYPE: PRT
<213> ORGANISM: Vicugna pacos

<400> SEQUENCE: 82

Cys Ile Gly Gly Ser Gly Ser Gly Leu Thr
1               5                   10

<210> SEQ ID NO 83
<211> LENGTH: 9
<212> TYPE: PRT
<213> ORGANISM: Vicugna pacos

<400> SEQUENCE: 83

Ala Ile Thr Ser Gly Ser Gly Ser Thr
1               5

<210> SEQ ID NO 84
<211> LENGTH: 9
<212> TYPE: PRT
<213> ORGANISM: Vicugna pacos

<400> SEQUENCE: 84

Cys Ile Ser Ser Asn Asp Gly Thr Thr
1               5

<210> SEQ ID NO 85
<211> LENGTH: 9
<212> TYPE: PRT
<213> ORGANISM: Vicugna pacos

<400> SEQUENCE: 85

Ser Ile Asn Ser Ser Gly Gly Ser Thr
1               5

<210> SEQ ID NO 86
<211> LENGTH: 9
<212> TYPE: PRT
<213> ORGANISM: Vicugna pacos

<400> SEQUENCE: 86

Ala Ile Ser Arg Ser Gly Asp Ser Thr
1               5

<210> SEQ ID NO 87
<211> LENGTH: 9
<212> TYPE: PRT
<213> ORGANISM: Vicugna pacos

<400> SEQUENCE: 87

Cys Ile Ser Tyr Lys Gly Gly Ser Thr
1               5

<210> SEQ ID NO 88
<211> LENGTH: 9
<212> TYPE: PRT
<213> ORGANISM: Vicugna pacos

<400> SEQUENCE: 88

Ser Ile Ser Trp Ser Ser Val Thr Thr
1               5
```

-continued

<210> SEQ ID NO 89
<211> LENGTH: 8
<212> TYPE: PRT
<213> ORGANISM: Vicugna pacos

<400> SEQUENCE: 89

Ala Ile Arg Leu Ser Gly Ala Arg
1               5

<210> SEQ ID NO 90
<211> LENGTH: 9
<212> TYPE: PRT
<213> ORGANISM: Vicugna pacos

<400> SEQUENCE: 90

Leu Ile Asn Leu Asp Asp Gly Glu Thr
1               5

<210> SEQ ID NO 91
<211> LENGTH: 9
<212> TYPE: PRT
<213> ORGANISM: Vicugna pacos

<400> SEQUENCE: 91

Ala Ile Thr Ser Gly Ser Gly Ser Thr
1               5

<210> SEQ ID NO 92
<211> LENGTH: 7
<212> TYPE: PRT
<213> ORGANISM: Vicugna pacos

<400> SEQUENCE: 92

Gly Ile Thr Gly Gly Asn Thr
1               5

<210> SEQ ID NO 93
<211> LENGTH: 8
<212> TYPE: PRT
<213> ORGANISM: Vicugna pacos

<400> SEQUENCE: 93

Leu Val Thr Gly Ser Gly Arg Thr
1               5

<210> SEQ ID NO 94
<211> LENGTH: 8
<212> TYPE: PRT
<213> ORGANISM: Vicugna pacos

<400> SEQUENCE: 94

Ala Val Ser Ser Gly Gly Ser Thr
1               5

<210> SEQ ID NO 95
<211> LENGTH: 9
<212> TYPE: PRT
<213> ORGANISM: Vicugna pacos

<400> SEQUENCE: 95

Ser Ile Thr Ser Ser Gly Leu Asp Thr
1               5

<210> SEQ ID NO 96

```
<211> LENGTH: 9
<212> TYPE: PRT
<213> ORGANISM: Vicugna pacos

<400> SEQUENCE: 96

Ser Ile Thr Ser Gly Gly Gly Ser Thr
1               5

<210> SEQ ID NO 97
<211> LENGTH: 8
<212> TYPE: PRT
<213> ORGANISM: Vicugna pacos

<400> SEQUENCE: 97

Glu Ile Thr Ser Ser Gly Ser Thr
1               5

<210> SEQ ID NO 98
<211> LENGTH: 8
<212> TYPE: PRT
<213> ORGANISM: Vicugna pacos

<400> SEQUENCE: 98

Ala Ile Ser Ser Gly Gly Ser Thr
1               5

<210> SEQ ID NO 99
<211> LENGTH: 8
<212> TYPE: PRT
<213> ORGANISM: Vicugna pacos

<400> SEQUENCE: 99

Asp Val Leu Pro Ser Gly Ser Thr
1               5

<210> SEQ ID NO 100
<211> LENGTH: 9
<212> TYPE: PRT
<213> ORGANISM: Vicugna pacos

<400> SEQUENCE: 100

Tyr Ile Gly Tyr Thr Gly Thr Ile Thr
1               5

<210> SEQ ID NO 101
<211> LENGTH: 9
<212> TYPE: PRT
<213> ORGANISM: Vicugna pacos

<400> SEQUENCE: 101

Tyr Ile Ser His Gly Gly Thr Thr Thr
1               5

<210> SEQ ID NO 102
<211> LENGTH: 11
<212> TYPE: PRT
<213> ORGANISM: Vicugna pacos

<400> SEQUENCE: 102

Asn Thr Tyr Ser Asp Ser Asp Val Tyr Gly Tyr
1               5                   10

<210> SEQ ID NO 103
<211> LENGTH: 15
<212> TYPE: PRT
```

<210> SEQ ID NO 103
<211> LENGTH: (not shown)
<212> TYPE: PRT
<213> ORGANISM: Vicugna pacos

<400> SEQUENCE: 103

Ser Ser Ile Tyr Gly Ser Ala Val Val Asp Gly Leu Tyr Asp Tyr
1               5                   10                  15

<210> SEQ ID NO 104
<211> LENGTH: 24
<212> TYPE: PRT
<213> ORGANISM: Vicugna pacos

<400> SEQUENCE: 104

Glu Arg Ala Pro Pro Tyr Tyr Ser Gly Tyr Tyr Phe Phe Asp Ser Thr
1               5                   10                  15

Cys Val Ala Ala Ser Tyr Asp Tyr
            20

<210> SEQ ID NO 105
<211> LENGTH: 13
<212> TYPE: PRT
<213> ORGANISM: Vicugna pacos

<400> SEQUENCE: 105

Asp Gly Val Val Ala Trp Asp Gln Pro Tyr Asp Asn Tyr
1               5                   10

<210> SEQ ID NO 106
<211> LENGTH: 17
<212> TYPE: PRT
<213> ORGANISM: Vicugna pacos

<400> SEQUENCE: 106

Asp Arg Arg Pro Tyr Asn Asp Trp Trp Asp Asp Trp Ser Trp Trp Val
1               5                   10                  15

Tyr

<210> SEQ ID NO 107
<211> LENGTH: 18
<212> TYPE: PRT
<213> ORGANISM: Vicugna pacos

<400> SEQUENCE: 107

Glu Ala Gln Thr Pro Tyr Asn Asp Gly Asp Cys Thr Arg Ala Ser Tyr
1               5                   10                  15

Asp Tyr

<210> SEQ ID NO 108
<211> LENGTH: 9
<212> TYPE: PRT
<213> ORGANISM: Vicugna pacos

<400> SEQUENCE: 108

Gly Phe Val Cys Tyr Asn Tyr Asp Tyr
1               5

<210> SEQ ID NO 109
<211> LENGTH: 22
<212> TYPE: PRT
<213> ORGANISM: Vicugna pacos

<400> SEQUENCE: 109

Asp Phe Phe Arg Trp Asp Ser Gly Ser Tyr Tyr Val Arg Gly Cys Arg
1               5                   10                  15

His Ala Thr Tyr Asp Tyr
            20

<210> SEQ ID NO 110
<211> LENGTH: 11
<212> TYPE: PRT
<213> ORGANISM: Vicugna pacos

<400> SEQUENCE: 110

Asp Ala Leu Thr Met Leu Pro Pro Phe Asp Phe
1               5                   10

<210> SEQ ID NO 111
<211> LENGTH: 12
<212> TYPE: PRT
<213> ORGANISM: Vicugna pacos

<400> SEQUENCE: 111

Ala Ile Val Thr Met Thr Ser Pro Tyr Ser Asp Tyr
1               5                   10

<210> SEQ ID NO 112
<211> LENGTH: 5
<212> TYPE: PRT
<213> ORGANISM: Vicugna pacos

<400> SEQUENCE: 112

Asn Trp Gly Ala Tyr
1               5

<210> SEQ ID NO 113
<211> LENGTH: 13
<212> TYPE: PRT
<213> ORGANISM: Vicugna pacos

<400> SEQUENCE: 113

Leu Met Val Asp Tyr Gly Leu Gly Leu Gly Thr Asp Tyr
1               5                   10

<210> SEQ ID NO 114
<211> LENGTH: 17
<212> TYPE: PRT
<213> ORGANISM: Vicugna pacos

<400> SEQUENCE: 114

Asp Thr Tyr Tyr Tyr Cys Ser Lys Arg Val Trp Arg Asn Asp Tyr Gly
1               5                   10                  15

Ser

<210> SEQ ID NO 115
<211> LENGTH: 13
<212> TYPE: PRT
<213> ORGANISM: Vicugna pacos

<400> SEQUENCE: 115

Asp Met Asp Ser Ser Leu Ser Gly Gly Tyr Val Asp Val
1               5                   10

<210> SEQ ID NO 116
<211> LENGTH: 16
<212> TYPE: PRT
<213> ORGANISM: Vicugna pacos

<400> SEQUENCE: 116

Glu Thr Pro Ser Ile Gly Ser Pro Cys Thr Ser Ala Ser Tyr Asp Tyr
1               5                   10                  15

<210> SEQ ID NO 117
<211> LENGTH: 16
<212> TYPE: PRT
<213> ORGANISM: Vicugna pacos

<400> SEQUENCE: 117

Leu Arg Arg Tyr Tyr Gly Leu Asn Leu Asp Pro Gly Ser Tyr Asp Tyr
1               5                   10                  15

<210> SEQ ID NO 118
<211> LENGTH: 15
<212> TYPE: PRT
<213> ORGANISM: Vicugna pacos

<400> SEQUENCE: 118

Arg Thr Val Ser Ala Pro Pro Ser Ala Ala Trp Gly Tyr Gly Tyr
1               5                   10                  15

<210> SEQ ID NO 119
<211> LENGTH: 9
<212> TYPE: PRT
<213> ORGANISM: Vicugna pacos

<400> SEQUENCE: 119

Gly Phe Val Cys Tyr Asn Tyr Asp Tyr
1               5

<210> SEQ ID NO 120
<211> LENGTH: 18
<212> TYPE: PRT
<213> ORGANISM: Vicugna pacos

<400> SEQUENCE: 120

His Leu Ala Gln Tyr Ser Asp Tyr Ala Tyr Arg Asp Pro His Gln Phe
1               5                   10                  15

Gly Ala

<210> SEQ ID NO 121
<211> LENGTH: 9
<212> TYPE: PRT
<213> ORGANISM: Vicugna pacos

<400> SEQUENCE: 121

Gly His Thr Trp Gly Gln Tyr Ala Tyr
1               5

<210> SEQ ID NO 122
<211> LENGTH: 10
<212> TYPE: PRT
<213> ORGANISM: Vicugna pacos

<400> SEQUENCE: 122

Arg Gly Arg Phe Asp Asp Asn Tyr Glu Tyr
1               5                   10

<210> SEQ ID NO 123
<211> LENGTH: 13
<212> TYPE: PRT
<213> ORGANISM: Vicugna pacos

<400> SEQUENCE: 123

-continued

Asp Met Asp Ser Ser Leu Ser Gly Gly Tyr Val Asp Val
1               5                   10

<210> SEQ ID NO 124
<211> LENGTH: 5
<212> TYPE: PRT
<213> ORGANISM: Vicugna pacos

<400> SEQUENCE: 124

Asn Trp Gly Ala Tyr
1               5

<210> SEQ ID NO 125
<211> LENGTH: 11
<212> TYPE: PRT
<213> ORGANISM: Vicugna pacos

<400> SEQUENCE: 125

Leu Val Ile Gly Pro Leu Glu Gly Tyr Asp Tyr
1               5                   10

<210> SEQ ID NO 126
<211> LENGTH: 13
<212> TYPE: PRT
<213> ORGANISM: Vicugna pacos

<400> SEQUENCE: 126

Asp Gly Val Val Ala Trp Asp Gln Pro Tyr Asp Asn Tyr
1               5                   10

<210> SEQ ID NO 127
<211> LENGTH: 9
<212> TYPE: PRT
<213> ORGANISM: Vicugna pacos

<400> SEQUENCE: 127

Glu Arg Trp Asp Asn Gly Met Val Tyr
1               5

<210> SEQ ID NO 128
<211> LENGTH: 23
<212> TYPE: PRT
<213> ORGANISM: Vicugna pacos

<400> SEQUENCE: 128

Glu Arg Trp Asp Gly Tyr Ala Leu Gly Tyr Ser Pro Asn His Gly Ser
1               5                   10                  15

Gly His Arg Pro Tyr Asn Tyr
            20

<210> SEQ ID NO 129
<211> LENGTH: 12
<212> TYPE: PRT
<213> ORGANISM: Vicugna pacos

<400> SEQUENCE: 129

Val Ala Val Thr Phe Thr Thr Pro Arg Ser Asp Tyr
1               5                   10

<210> SEQ ID NO 130
<211> LENGTH: 8
<212> TYPE: PRT
<213> ORGANISM: Vicugna pacos

<400> SEQUENCE: 130

Gly Gly Gly Trp Arg Pro Gly Ala
1               5

<210> SEQ ID NO 131
<211> LENGTH: 8
<212> TYPE: PRT
<213> ORGANISM: Vicugna pacos

<400> SEQUENCE: 131

Asn Arg Glu Thr Met Pro Pro Phe
1               5

<210> SEQ ID NO 132
<211> LENGTH: 12
<212> TYPE: PRT
<213> ORGANISM: Vicugna pacos

<400> SEQUENCE: 132

Gly Tyr Ala Arg Leu Ile Ala Asp Ser Asp Leu Val
1               5                   10

<210> SEQ ID NO 133
<211> LENGTH: 12
<212> TYPE: PRT
<213> ORGANISM: Vicugna pacos

<400> SEQUENCE: 133

Gly Tyr Ala Arg Leu Met Thr Asp Ser Glu Leu Val
1               5                   10

<210> SEQ ID NO 134
<211> LENGTH: 375
<212> TYPE: DNA
<213> ORGANISM: Vicugna pacos

<400> SEQUENCE: 134
caggtgcagc tgcaggagtc tggaggaggc ttggtgcagc ctggggggtc tctgagactc      60
tcctgtgcag cctctggaaa catcttcagt atcaatgcca tcggctggta ccgccaggct     120
ccagggaagc agcgcgagtt ggtcgcaact attactctta gtggtagcac aaactatgca     180
gactccgtga aggccgatt ctccatctcc agagacaacg ccaagaacac ggtgtatctg      240
caaatgaaca gcctgaaacc tgaggacacg gccgtctatt actgtaatgc taacacctat     300
agcgactctg acgtttatgg ctactggggc caggggaccc aggtcaccgt ctcctcacac     360
caccatcacc atcac                                                     375

<210> SEQ ID NO 135
<211> LENGTH: 357
<212> TYPE: DNA
<213> ORGANISM: Vicugna pacos

<400> SEQUENCE: 135
caggtgcagc tgcaggagtc tggaggaggc ttggtgcagc ctggggggtc tctgagactc      60
tcctgtgcag cctctggaaa catcttcagt atcaatgcca tcggctggta ccgccaggct     120
ccagggaagc agcgcgagtt ggtcgcaact attactctta gtggtagcac aaactatgca     180
gactccgtga aggccgatt ctccatctcc agagacaacg ccaagaacac ggtgtatctg      240
caaatgaaca gcctgaaacc tgaggacacg gccgtctatt actgtaatgc taacacctat     300
agcgactctg acgtttatgg ctactggggc caggggaccc aggtcaccgt ctcctca        357

<210> SEQ ID NO 136
<211> LENGTH: 390
<212> TYPE: DNA
<213> ORGANISM: Vicugna pacos

<400> SEQUENCE: 136

```
caggtgcagc tgcaggagtc tggaggagga ttggtgcagg ctgggggctc tctgagactc      60
tcctgtgcag cctctggacg caccttcagt agagatgcca tgggctggtt ccgccaggct     120
ccagggaagg agcgtgagtt tgtagcaggt attagctgga gtggtggtag cacatactat     180
gcagactccg tgaagggccg attcaccatc tccagggacg cgccaagaa cacggtaaat      240
ctgcaaatga acagcctgaa acctgaggac acggccgttt attactgtgc agcatcgtcg     300
atttatggga gtgcggtagt agatgggctg tatgactact ggggccaggg gacccaggtc     360
accgtctcct cacaccacca tcaccatcac                                       390
```

<210> SEQ ID NO 137
<211> LENGTH: 372
<212> TYPE: DNA
<213> ORGANISM: Vicugna pacos

<400> SEQUENCE: 137

```
caggtgcagc tgcaggagtc tggaggagga ttggtgcagg ctgggggctc tctgagactc      60
tcctgtgcag cctctggacg caccttcagt agagatgcca tgggctggtt ccgccaggct     120
ccagggaagg agcgtgagtt tgtagcaggt attagctgga gtggtggtag cacatactat     180
gcagactccg tgaagggccg attcaccatc tccagggacg cgccaagaa cacggtaaat      240
ctgcaaatga acagcctgaa acctgaggac acggccgttt attactgtgc agcatcgtcg     300
atttatggga gtgcggtagt agatgggctg tatgactact ggggccaggg gacccaggtc     360
accgtctcct ca                                                          372
```

<210> SEQ ID NO 138
<211> LENGTH: 780
<212> TYPE: DNA
<213> ORGANISM: Vicugna pacos

<400> SEQUENCE: 138

```
caggtgcagc ttcaggagtc tggaggaggc ttggtgcagc ctgggggtc tctgagactc       60
tcctgtgcag cctctggaaa catcttcagt atcaatgcca tcggctggta ccgccaggct     120
ccagggaagc agcgcgagtt ggtcgcaact attactctta gtggtagcac aaactatgca     180
gactccgtga agggccgatt ctccatctcc agagacaacg ccaagaacac ggtgtatctg     240
caaatgaaca gcctgaaacc tgaggacacg gccgtctatt actgtaatgc taacacctat     300
agcgactctg acgtttatgg ctactggggc caggggaccc aggtcaccgt ctcctcaagc     360
ccatctacac ctcccacacc atcaccatcc acaccaccgg caagtcaggt gcagctgcag     420
gagtctggag gaggcttggt gcagcctggg gggtctctga ctctcctg tgcagcctct       480
ggaaacatct tcagtatcaa tgccatcggc tggtaccgcc aggctccagg aagcagcgc      540
gagttggtcg caactattac tcttagtggt agcacaaact atgcagactc cgtgaagggc     600
cgattctcca tctccagaga caacgccaag aacacggtgt atctgcaaat gaacagcctg     660
aaacctgagg acacggccgt ctattactgt aatgctaaca cctatagcga ctctgacgtt     720
tatggctact ggggccaggg gacccaggtc accgtctcct cacaccacca tcaccatcac     780
```

<210> SEQ ID NO 139
<211> LENGTH: 777
<212> TYPE: DNA
<213> ORGANISM: Vicugna pacos

<400> SEQUENCE: 139

| | | | | | |
|---|---|---|---|---|---|
| caggtgcagc | ttcaggagtc | tggaggaggc | ttggtgcagc | ctgggggtc | tctgagactc | 60 |
| tcctgtgcag | cctctggaaa | catcttcagt | atcaatgcca | tcggctggta | ccgccaggct | 120 |
| ccagggaagc | agcgcgagtt | ggtcgcaact | attactctta | gtggtagcac | aaactatgca | 180 |
| gactccgtga | agggccgatt | ctccatctcc | agagacaacg | ccaagaacac | ggtgtatctg | 240 |
| caaatgaaca | gcctgaaacc | tgaggacacg | gccgtctatt | actgtaatgc | taacacctat | 300 |
| agcgactctg | acgtttatgg | ctactggggc | caggggaccc | aggtcaccgt | ctcctcaggc | 360 |
| ggaggcggta | gtggcggagg | tggatctgga | ggcggcggta | gtcaggtgca | gctgcaggag | 420 |
| tctggaggag | gcttggtgca | gcctgggggg | tctctgagac | tctcctgtgc | agcctctgga | 480 |
| aacatcttca | gtatcaatgc | catcggctgg | taccgccagg | ctccagggaa | gcagcgcgag | 540 |
| ttggtcgcaa | ctattactct | tagtggtagc | acaaactatg | cagactccgt | gaagggccga | 600 |
| ttctccatct | ccagagacaa | cgccaagaac | acggtgtatc | tgcaaatgaa | cagcctgaaa | 660 |
| cctgaggaca | cggccgtcta | ttactgtaat | gctaacacct | atagcgactc | tgacgtttat | 720 |
| ggctactggg | gccaggggac | ccaggtcacc | gtctcctcac | accaccatca | ccatcac | 777 |

<210> SEQ ID NO 140
<211> LENGTH: 783
<212> TYPE: DNA
<213> ORGANISM: Vicugna pacos

<400> SEQUENCE: 140

| | | | | | |
|---|---|---|---|---|---|
| caggtgcagc | ttcaggagtc | tggaggaggc | ttggtgcagc | ctgggggtc | tctgagactc | 60 |
| tcctgtgcag | cctctggaaa | catcttcagt | atcaatgcca | tcggctggta | ccgccaggct | 120 |
| ccagggaagc | agcgcgagtt | ggtcgcaact | attactctta | gtggtagcac | aaactatgca | 180 |
| gactccgtga | agggccgatt | ctccatctcc | agagacaacg | ccaagaacac | ggtgtatctg | 240 |
| caaatgaaca | gcctgaaacc | tgaggacacg | gccgtctatt | actgtaatgc | taacacctat | 300 |
| agcgactctg | acgtttatgg | ctactggggc | caggggaccc | aggtcaccgt | ctcctcagcg | 360 |
| caccacagcg | aagaccccag | ctccaaagct | cccaaagctc | caatggcaca | ggtgcagctg | 420 |
| caggagtctg | gaggaggctt | ggtgcagcct | gggggtctc | tgagactctc | ctgtgcagcc | 480 |
| tctggaaaca | tcttcagtat | caatgccatc | ggctggtacc | gccaggctcc | agggaagcag | 540 |
| cgcgagttgg | tcgcaactat | tactcttagt | ggtagcacaa | actatgcaga | ctccgtgaag | 600 |
| ggccgattct | ccatctccag | agacaacgcc | aagaacacgg | tgtatctgca | aatgaacagc | 660 |
| ctgaaacctg | aggacacggc | cgtctattac | tgtaatgcta | acacctatag | cgactctgac | 720 |
| gtttatggct | actggggcca | ggggacccag | gtcaccgtct | cctcacacca | ccatcaccat | 780 |
| cac | | | | | | 783 |

<210> SEQ ID NO 141
<211> LENGTH: 1456
<212> TYPE: PRT
<213> ORGANISM: Homo sapiens

<400> SEQUENCE: 141

Met Arg Leu Pro Leu Leu Leu Val Phe Ala Ser Val Ile Pro Gly Ala

-continued

```
1               5                   10                  15
Val Leu Leu Leu Asp Thr Arg Gln Phe Leu Ile Tyr Asn Glu Asp His
            20                  25                  30
Lys Arg Cys Val Asp Ala Val Ser Pro Ser Ala Val Gln Thr Ala Ala
            35                  40                  45
Cys Asn Gln Asp Ala Glu Ser Gln Lys Phe Arg Trp Val Ser Glu Ser
    50                  55                  60
Gln Ile Met Ser Val Ala Phe Lys Leu Cys Leu Gly Val Pro Ser Lys
65                  70                  75                  80
Thr Asp Trp Val Ala Ile Thr Leu Tyr Ala Cys Asp Ser Lys Ser Glu
                85                  90                  95
Phe Gln Lys Trp Glu Cys Lys Asn Asp Thr Leu Leu Gly Ile Lys Gly
                100                 105                 110
Glu Asp Leu Phe Phe Asn Tyr Gly Asn Arg Gln Glu Lys Asn Ile Met
            115                 120                 125
Leu Tyr Lys Gly Ser Gly Leu Trp Ser Arg Trp Lys Ile Tyr Gly Thr
        130                 135                 140
Thr Asp Asn Leu Cys Ser Arg Gly Tyr Glu Ala Met Tyr Thr Leu Leu
145                 150                 155                 160
Gly Asn Ala Asn Gly Ala Thr Cys Ala Phe Pro Phe Lys Phe Glu Asn
                165                 170                 175
Lys Trp Tyr Ala Asp Cys Thr Ser Ala Gly Arg Ser Asp Gly Trp Leu
                180                 185                 190
Trp Cys Gly Thr Thr Thr Asp Tyr Asp Thr Asp Lys Leu Phe Gly Tyr
            195                 200                 205
Cys Pro Leu Lys Phe Glu Gly Ser Glu Ser Leu Trp Asn Lys Asp Pro
210                 215                 220
Leu Thr Ser Val Ser Tyr Gln Ile Asn Ser Lys Ser Ala Leu Thr Trp
225                 230                 235                 240
His Gln Ala Arg Lys Ser Cys Gln Gln Asn Ala Glu Leu Leu Ser
                245                 250                 255
Ile Thr Glu Ile His Glu Gln Thr Tyr Leu Thr Gly Leu Thr Ser Ser
            260                 265                 270
Leu Thr Ser Gly Leu Trp Ile Gly Leu Asn Ser Leu Ser Phe Asn Ser
        275                 280                 285
Gly Trp Gln Trp Ser Asp Arg Ser Pro Phe Arg Tyr Leu Asn Trp Leu
    290                 295                 300
Pro Gly Ser Pro Ser Ala Glu Pro Gly Lys Ser Cys Val Ser Leu Asn
305                 310                 315                 320
Pro Gly Lys Asn Ala Lys Trp Glu Asn Leu Glu Cys Val Gln Lys Leu
                325                 330                 335
Gly Tyr Ile Cys Lys Lys Gly Asn Thr Thr Leu Asn Ser Phe Val Ile
            340                 345                 350
Pro Ser Glu Ser Asp Val Pro Thr His Cys Pro Ser Gln Trp Trp Pro
        355                 360                 365
Tyr Ala Gly His Cys Tyr Lys Ile His Arg Asp Glu Lys Lys Ile Gln
    370                 375                 380
Arg Asp Ala Leu Thr Thr Cys Arg Lys Glu Gly Gly Asp Leu Thr Ser
385                 390                 395                 400
Ile His Thr Ile Glu Glu Leu Asp Phe Ile Ile Ser Gln Leu Gly Tyr
            405                 410                 415
Glu Pro Asn Asp Glu Leu Trp Ile Gly Leu Asn Asp Ile Lys Ile Gln
        420                 425                 430
```

-continued

```
Met Tyr Phe Glu Trp Ser Asp Gly Thr Pro Val Thr Phe Thr Lys Trp
            435                 440                 445

Leu Arg Gly Glu Pro Ser His Glu Asn Asn Arg Gln Glu Asp Cys Val
450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
            500                 505                 510

Phe Tyr Cys Tyr Met Ile Gly His Thr Leu Ser Thr Phe Ala Glu Ala
            515                 520                 525

Asn Gln Thr Cys Asn Asn Glu Asn Ala Tyr Leu Thr Thr Ile Glu Asp
530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
            595                 600                 605

Gly Gly Leu Trp Asp Val Leu Lys Cys Asp Glu Lys Ala Lys Phe Val
            610                 615                 620

Cys Lys His Trp Ala Glu Gly Val Thr His Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
            675                 680                 685

Ser Ile Asn Asn Lys Glu Glu Gln Gln Thr Ile Trp Arg Leu Ile Thr
            690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Thr Met Ser Trp Asn Asp Ile Asn
            755                 760                 765

Cys Glu His Leu Asn Asn Trp Ile Cys Gln Ile Gln Lys Gly Gln Thr
            770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
                805                 810                 815

Glu Lys Glu Thr Met Asp Asn Ala Arg Ala Phe Cys Lys Arg Asn Phe
            820                 825                 830

Gly Asp Leu Val Ser Ile Gln Ser Glu Ser Glu Lys Lys Phe Leu Trp
            835                 840                 845
```

-continued

```
Lys Tyr Val Asn Arg Asn Asp Ala Gln Ser Ala Tyr Phe Ile Gly Leu
    850             855             860

Leu Ile Ser Leu Asp Lys Lys Phe Ala Trp Met Asp Gly Ser Lys Val
865             870             875             880

Asp Tyr Val Ser Trp Ala Thr Gly Glu Pro Asn Phe Ala Asn Glu Asp
            885             890             895

Glu Asn Cys Val Thr Met Tyr Ser Asn Ser Gly Phe Trp Asn Asp Ile
            900             905             910

Asn Cys Gly Tyr Pro Asn Ala Phe Ile Cys Gln Arg His Asn Ser Ser
            915             920             925

Ile Asn Ala Thr Thr Val Met Pro Thr Met Pro Ser Val Pro Ser Gly
    930             935             940

Cys Lys Glu Gly Trp Asn Phe Tyr Ser Asn Lys Cys Phe Lys Ile Phe
945             950             955             960

Gly Phe Met Glu Glu Glu Arg Lys Asn Trp Gln Glu Ala Arg Lys Ala
            965             970             975

Cys Ile Gly Phe Gly Gly Asn Leu Val Ser Ile Gln Asn Glu Lys Glu
            980             985             990

Gln Ala Phe Leu Thr Tyr His Met Lys Asp Ser Thr Phe Ser Ala Trp
            995             1000            1005

Thr Gly Leu Asn Asp Val Asn Ser Glu His Thr Phe Leu Trp Thr
    1010            1015            1020

Asp Gly Arg Gly Val His Tyr Thr Asn Trp Gly Lys Gly Tyr Pro
    1025            1030            1035

Gly Gly Arg Arg Ser Ser Leu Ser Tyr Glu Asp Ala Asp Cys Val
    1040            1045            1050

Val Ile Ile Gly Gly Ala Ser Asn Glu Ala Gly Lys Trp Met Asp
    1055            1060            1065

Asp Thr Cys Asp Ser Lys Arg Gly Tyr Ile Cys Gln Thr Arg Ser
    1070            1075            1080

Asp Pro Ser Leu Thr Asn Pro Pro Ala Thr Ile Gln Thr Asp Gly
    1085            1090            1095

Phe Val Lys Tyr Gly Lys Ser Ser Tyr Ser Leu Met Arg Gln Lys
    1100            1105            1110

Phe Gln Trp His Glu Ala Glu Thr Tyr Cys Lys Leu His Asn Ser
    1115            1120            1125

Leu Ile Ala Ser Ile Leu Asp Pro Tyr Ser Asn Ala Phe Ala Trp
    1130            1135            1140

Leu Gln Met Glu Thr Ser Asn Glu Arg Val Trp Ile Ala Leu Asn
    1145            1150            1155

Ser Asn Leu Thr Asp Asn Gln Tyr Thr Trp Thr Asp Lys Trp Arg
    1160            1165            1170

Val Arg Tyr Thr Asn Trp Ala Ala Asp Glu Pro Lys Leu Lys Ser
    1175            1180            1185

Ala Cys Val Tyr Leu Asp Leu Asp Gly Tyr Trp Lys Thr Ala His
    1190            1195            1200

Cys Asn Glu Ser Phe Tyr Phe Leu Cys Lys Arg Ser Asp Glu Ile
    1205            1210            1215

Pro Ala Thr Glu Pro Pro Gln Leu Pro Gly Arg Cys Pro Glu Ser
    1220            1225            1230

Asp His Thr Ala Trp Ile Pro Phe His Gly His Cys Tyr Tyr Ile
    1235            1240            1245

Glu Ser Ser Tyr Thr Arg Asn Trp Gly Gln Ala Ser Leu Glu Cys
```

```
                    1250                1255                1260
Leu Arg Met Gly Ser Ser Leu Val Ser Ile Glu Ser Ala Ala Glu
            1265                1270                1275
Ser Ser Phe Leu Ser Tyr Arg Val Glu Pro Leu Lys Ser Lys Thr
        1280                1285                1290
Asn Phe Trp Ile Gly Leu Phe Arg Asn Val Glu Gly Thr Trp Leu
    1295                1300                1305
Trp Ile Asn Asn Ser Pro Val Ser Phe Val Asn Trp Asn Thr Gly
1310                1315                1320
Asp Pro Ser Gly Glu Arg Asn Asp Cys Val Ala Leu His Ala Ser
    1325                1330                1335
Ser Gly Phe Trp Ser Asn Ile His Cys Ser Ser Tyr Lys Gly Tyr
        1340                1345                1350
Ile Cys Lys Arg Pro Lys Ile Ile Asp Ala Lys Pro Thr His Glu
            1355                1360                1365
Leu Leu Thr Thr Lys Ala Asp Thr Arg Lys Met Asp Pro Ser Lys
                1370                1375                1380
Pro Ser Ser Asn Val Ala Gly Val Val Ile Ile Val Ile Leu Leu
                    1385                1390                1395
Ile Leu Thr Gly Ala Gly Leu Ala Ala Tyr Phe Phe Tyr Lys Lys
                        1400                1405                1410
Arg Arg Val His Leu Pro Gln Glu Gly Ala Phe Glu Asn Thr Leu
                            1415                1420                1425
Tyr Phe Asn Ser Gln Ser Ser Pro Gly Thr Ser Asp Met Lys Asp
                                1430                1435                1440
Leu Val Gly Asn Ile Glu Gln Asn Glu His Ser Val Ile
                                    1445                1450                1455

<210> SEQ ID NO 142
<211> LENGTH: 1371
<212> TYPE: PRT
<213> ORGANISM: Homo sapiens

<400> SEQUENCE: 142

Leu Leu Asp Thr Arg Gln Phe Leu Ile Tyr Asn Glu Asp His Lys Arg
1               5                   10                  15
Cys Val Asp Ala Val Ser Pro Ser Ala Val Gln Thr Ala Ala Cys Asn
            20                  25                  30
Gln Asp Ala Glu Ser Gln Lys Phe Arg Trp Val Ser Glu Ser Gln Ile
        35                  40                  45
Met Ser Val Ala Phe Lys Leu Cys Leu Gly Val Pro Ser Lys Thr Asp
    50                  55                  60
Trp Val Ala Ile Thr Leu Tyr Ala Cys Asp Ser Lys Ser Glu Phe Gln
65                  70                  75                  80
Lys Trp Glu Cys Lys Asn Asp Thr Leu Leu Gly Ile Lys Gly Glu Asp
                85                  90                  95
Leu Phe Phe Asn Tyr Gly Asn Arg Gln Glu Lys Asn Ile Met Leu Tyr
            100                 105                 110
Lys Gly Ser Gly Leu Trp Ser Arg Trp Lys Ile Tyr Gly Thr Thr Asp
        115                 120                 125
Asn Leu Cys Ser Arg Gly Tyr Glu Ala Met Tyr Thr Leu Leu Gly Asn
    130                 135                 140
Ala Asn Gly Ala Thr Cys Ala Phe Pro Phe Lys Phe Glu Asn Lys Trp
145                 150                 155                 160
```

```
Tyr Ala Asp Cys Thr Ser Ala Gly Arg Ser Asp Gly Trp Leu Trp Cys
                165                 170                 175
Gly Thr Thr Thr Asp Tyr Asp Thr Asp Lys Leu Phe Gly Tyr Cys Pro
            180                 185                 190
Leu Lys Phe Glu Gly Ser Glu Ser Leu Trp Asn Lys Asp Pro Leu Thr
        195                 200                 205
Ser Val Ser Tyr Gln Ile Asn Ser Lys Ser Ala Leu Thr Trp His Gln
    210                 215                 220
Ala Arg Lys Ser Cys Gln Gln Gln Asn Ala Glu Leu Leu Ser Ile Thr
225                 230                 235                 240
Glu Ile His Glu Gln Thr Tyr Leu Thr Gly Leu Thr Ser Ser Leu Thr
                245                 250                 255
Ser Gly Leu Trp Ile Gly Leu Asn Ser Leu Ser Phe Asn Ser Gly Trp
            260                 265                 270
Gln Trp Ser Asp Arg Ser Pro Phe Arg Tyr Leu Asn Trp Leu Pro Gly
        275                 280                 285
Ser Pro Ser Ala Glu Pro Gly Lys Ser Cys Val Ser Leu Asn Pro Gly
    290                 295                 300
Lys Asn Ala Lys Trp Glu Asn Leu Glu Cys Val Gln Lys Leu Gly Tyr
305                 310                 315                 320
Ile Cys Lys Lys Gly Asn Thr Thr Leu Asn Ser Phe Val Ile Pro Ser
                325                 330                 335
Glu Ser Asp Val Pro Thr His Cys Pro Ser Gln Trp Trp Pro Tyr Ala
            340                 345                 350
Gly His Cys Tyr Lys Ile His Arg Asp Glu Lys Lys Ile Gln Arg Asp
        355                 360                 365
Ala Leu Thr Thr Cys Arg Lys Glu Gly Gly Asp Leu Ala Ser Ile His
    370                 375                 380
Thr Ile Glu Glu Phe Asp Phe Ile Ile Ser Gln Leu Gly Tyr Glu Pro
385                 390                 395                 400
Asn Asp Glu Leu Trp Ile Gly Leu Asn Asp Ile Lys Ile Gln Met Tyr
                405                 410                 415
Phe Glu Trp Ser Asp Gly Thr Pro Val Thr Phe Thr Lys Trp Leu Arg
            420                 425                 430
Gly Glu Pro Ser His Glu Asn Asn Arg Gln Glu Asp Cys Val Val Met
        435                 440                 445
Lys Gly Lys Asp Gly Tyr Trp Ala Asp Arg Gly Cys Glu Trp Pro Leu
    450                 455                 460
Gly Tyr Ile Cys Lys Met Lys Ser Arg Ser Gln Gly Pro Glu Ile Val
465                 470                 475                 480
Glu Val Glu Lys Gly Cys Arg Lys Gly Trp Lys Lys His His Phe Tyr
                485                 490                 495
Cys Tyr Met Ile Gly His Thr Leu Ser Thr Phe Ala Glu Ala Asn Gln
            500                 505                 510
Thr Cys Asn Asn Glu Asn Ala Tyr Leu Thr Thr Ile Glu Asp Arg Tyr
        515                 520                 525
Glu Gln Ala Phe Leu Thr Ser Phe Val Gly Leu Arg Pro Glu Lys Tyr
    530                 535                 540
Phe Trp Thr Gly Leu Ser Asp Ile Gln Thr Lys Gly Thr Phe Gln Trp
545                 550                 555                 560
Thr Ile Glu Glu Glu Val Arg Phe Thr His Trp Asn Ser Asp Met Pro
                565                 570                 575
Gly Arg Lys Pro Gly Cys Val Ala Met Arg Thr Gly Ile Ala Gly Gly
```

-continued

```
            580                 585                 590
Leu Trp Asp Val Leu Lys Cys Asp Glu Lys Ala Lys Phe Val Cys Lys
            595                 600                 605
His Trp Ala Glu Gly Val Thr His Pro Pro Lys Pro Thr Thr Thr Pro
            610                 615                 620
Glu Pro Lys Cys Pro Glu Asp Trp Gly Ala Ser Ser Arg Thr Ser Leu
625                 630                 635                 640
Cys Phe Lys Leu Tyr Ala Lys Gly Lys His Glu Lys Lys Thr Trp Phe
            645                 650                 655
Glu Ser Arg Asp Phe Cys Arg Ala Leu Gly Gly Asp Leu Ala Ser Ile
            660                 665                 670
Asn Asn Lys Glu Glu Gln Gln Thr Ile Trp Arg Leu Ile Thr Ala Ser
            675                 680                 685
Gly Ser Tyr His Lys Leu Phe Trp Leu Gly Leu Thr Tyr Gly Ser Pro
            690                 695                 700
Ser Glu Gly Phe Thr Trp Ser Asp Gly Ser Pro Val Ser Tyr Glu Asn
705                 710                 715                 720
Trp Ala Tyr Gly Glu Pro Asn Asn Tyr Gln Asn Val Glu Tyr Cys Gly
            725                 730                 735
Glu Leu Lys Gly Asp Pro Thr Met Ser Trp Asn Asp Ile Asn Cys Glu
            740                 745                 750
His Leu Asn Asn Trp Ile Cys Gln Ile Gln Lys Gly Gln Thr Pro Lys
            755                 760                 765
Pro Glu Pro Thr Pro Ala Pro Gln Asp Asn Pro Pro Val Thr Glu Asp
            770                 775                 780
Gly Trp Val Ile Tyr Lys Asp Tyr Gln Tyr Tyr Phe Ser Lys Glu Lys
785                 790                 795                 800
Glu Thr Met Asp Asn Ala Arg Ala Phe Cys Lys Arg Asn Phe Gly Asp
            805                 810                 815
Leu Val Ser Ile Gln Ser Glu Ser Glu Lys Lys Phe Leu Trp Lys Tyr
            820                 825                 830
Val Asn Arg Asn Asp Ala Gln Ser Ala Tyr Phe Ile Gly Leu Leu Ile
            835                 840                 845
Ser Leu Asp Lys Lys Phe Ala Trp Met Asp Gly Ser Lys Val Asp Tyr
            850                 855                 860
Val Ser Trp Ala Thr Gly Glu Pro Asn Phe Ala Asn Glu Asp Glu Asn
865                 870                 875                 880
Cys Val Thr Met Tyr Ser Asn Ser Gly Phe Trp Asn Asp Ile Asn Cys
                        885                 890                 895
Gly Tyr Pro Asn Ala Phe Ile Cys Gln Arg His Asn Ser Ser Ile Asn
            900                 905                 910
Ala Thr Thr Val Met Pro Thr Met Pro Ser Val Pro Ser Gly Cys Lys
            915                 920                 925
Glu Gly Trp Asn Phe Tyr Ser Asn Lys Cys Phe Lys Ile Phe Gly Phe
            930                 935                 940
Met Glu Glu Glu Arg Lys Asn Trp Gln Glu Ala Arg Lys Ala Cys Ile
945                 950                 955                 960
Gly Phe Gly Gly Asn Leu Val Ser Ile Gln Asn Glu Lys Glu Gln Ala
                        965                 970                 975
Phe Leu Thr Tyr His Met Lys Asp Ser Thr Phe Ser Ala Trp Thr Gly
            980                 985                 990
Leu Asn Asp Val Asn Ser Glu His  Thr Phe Leu Trp Thr Asp Gly Arg
            995                     1000                1005
```

Gly Val His Tyr Thr Asn Trp Gly Lys Gly Tyr Pro Gly Gly Arg
1010                1015                1020

Arg Ser Ser Leu Ser Tyr Glu Asp Ala Asp Cys Val Val Ile Ile
    1025                1030                1035

Gly Gly Ala Ser Asn Glu Ala Gly Lys Trp Met Asp Asp Thr Cys
1040                1045                1050

Asp Ser Lys Arg Gly Tyr Ile Cys Gln Thr Arg Ser Asp Pro Ser
    1055                1060                1065

Leu Thr Asn Pro Pro Ala Thr Ile Gln Thr Asp Gly Phe Val Lys
1070                1075                1080

Tyr Gly Lys Ser Ser Tyr Ser Leu Met Arg Gln Lys Phe Gln Trp
    1085                1090                1095

His Glu Ala Glu Thr Tyr Cys Lys Leu His Asn Ser Leu Ile Ala
1100                1105                1110

Ser Ile Leu Asp Pro Tyr Ser Asn Ala Phe Ala Trp Leu Gln Met
    1115                1120                1125

Glu Thr Ser Asn Glu Arg Val Trp Ile Ala Leu Asn Ser Asn Leu
1130                1135                1140

Thr Asp Asn Gln Tyr Thr Trp Thr Asp Lys Trp Arg Val Arg Tyr
    1145                1150                1155

Thr Asn Trp Ala Ala Asp Glu Pro Lys Leu Lys Ser Ala Cys Val
1160                1165                1170

Tyr Leu Asp Leu Asp Gly Tyr Trp Lys Thr Ala His Cys Asn Glu
    1175                1180                1185

Ser Phe Tyr Phe Leu Cys Lys Arg Ser Asp Glu Ile Pro Ala Thr
1190                1195                1200

Glu Pro Pro Gln Leu Pro Gly Arg Cys Pro Glu Ser Asp His Thr
    1205                1210                1215

Ala Trp Ile Pro Phe His Gly His Cys Tyr Tyr Ile Glu Ser Ser
1220                1225                1230

Tyr Thr Arg Asn Trp Gly Gln Ala Ser Leu Glu Cys Leu Arg Met
    1235                1240                1245

Gly Ser Ser Leu Val Ser Ile Glu Ser Ala Ala Glu Ser Ser Phe
1250                1255                1260

Leu Ser Tyr Arg Val Glu Pro Leu Lys Ser Lys Thr Asn Phe Trp
    1265                1270                1275

Ile Gly Leu Phe Arg Asn Val Glu Gly Thr Trp Leu Trp Ile Asn
1280                1285                1290

Asn Ser Pro Val Ser Phe Val Asn Trp Asn Thr Gly Asp Pro Ser
    1295                1300                1305

Gly Glu Arg Asn Asp Cys Val Ala Leu His Ala Ser Ser Gly Phe
1310                1315                1320

Trp Ser Asn Ile His Cys Ser Ser Tyr Lys Gly Tyr Ile Cys Lys
    1325                1330                1335

Arg Pro Lys Ile Ile Asp Ala Lys Pro Thr His Glu Leu Leu Thr
1340                1345                1350

Thr Lys Ala Asp Thr Arg Lys Met Asp Pro Ser Lys His His His
    1355                1360                1365

His His His
1370

<210> SEQ ID NO 143
<211> LENGTH: 1456

<212> TYPE: PRT
<213> ORGANISM: Mus musculus

<400> SEQUENCE: 143

```
Met Arg Leu Leu Leu Leu Ala Phe Ile Ser Val Ile Pro Val Ser
1               5                   10                  15

Val Gln Leu Leu Asp Ala Arg Gln Phe Leu Ile Tyr Asn Glu Asp His
            20                  25                  30

Lys Arg Cys Val Asp Ala Leu Ser Ala Ile Ser Val Gln Thr Ala Thr
        35                  40                  45

Cys Asn Pro Glu Ala Glu Ser Gln Lys Phe Arg Trp Val Ser Asp Ser
    50                  55                  60

Gln Ile Met Ser Val Ala Phe Lys Leu Cys Leu Gly Val Pro Ser Lys
65                  70                  75                  80

Thr Asp Trp Ala Ser Val Thr Leu Tyr Ala Cys Asp Ser Lys Ser Glu
                85                  90                  95

Tyr Gln Lys Trp Glu Cys Lys Asn Asp Thr Leu Phe Gly Ile Lys Gly
            100                 105                 110

Thr Glu Leu Tyr Phe Asn Tyr Gly Asn Arg Gln Glu Lys Asn Ile Lys
        115                 120                 125

Leu Tyr Lys Gly Ser Gly Leu Trp Ser Arg Trp Lys Val Tyr Gly Thr
    130                 135                 140

Thr Asp Asp Leu Cys Ser Arg Gly Tyr Glu Ala Met Tyr Ser Leu Leu
145                 150                 155                 160

Gly Asn Ala Asn Gly Ala Val Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Asp Tyr Asp Lys Asp Lys Leu Phe Gly Phe
        195                 200                 205

Cys Pro Leu His Phe Glu Gly Ser Glu Arg Leu Trp Asn Lys Asp Pro
    210                 215                 220

Leu Thr Gly Ile Leu Tyr Gln Ile Asn Ser Lys Ser Ala Leu Thr Trp
225                 230                 235                 240

His Gln Ala Arg Ala Ser Cys Lys Gln Gln Asn Ala Asp Leu Leu Ser
                245                 250                 255

Val Thr Glu Ile His Glu Gln Met Tyr Leu Thr Gly Leu Thr Ser Ser
            260                 265                 270

Leu Ser Ser Gly Leu Trp Ile Gly Leu Asn Ser Leu Ser Val Arg Ser
        275                 280                 285

Gly Trp Gln Trp Ala Gly Gly Ser Pro Phe Arg Tyr Leu Asn Trp Leu
    290                 295                 300

Pro Gly Ser Pro Ser Glu Pro Gly Lys Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Asn Thr Leu Asn Pro Phe Ile Ile
            340                 345                 350

Pro Ser Ala Ser Asp Val Pro Thr Gly Cys Pro Asn Gln Trp Trp Pro
        355                 360                 365

Tyr Ala Gly His Cys Tyr Arg Ile His Arg Glu Glu Lys Ile Gln
    370                 375                 380

Lys Tyr Ala Leu Gln Ala Cys Arg Lys Glu Gly Gly Asp Leu Ala Ser
385                 390                 395                 400
```

-continued

```
Ile His Ser Ile Glu Glu Phe Asp Phe Ile Phe Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
        435                 440                 445

Leu Pro Gly Glu Pro Ser His Glu Asn Asn Arg Gln Glu Asp Cys Val
    450                 455                 460

Val Met Lys Gly Lys Asp Gly Tyr Trp Ala Asp Arg Ala Cys Glu Gln
465                 470                 475                 480

Pro Leu Gly Tyr Ile Cys Lys Met Val Ser Gln Ser His Ala Val Val
                485                 490                 495

Pro Glu Gly Ala Asp Lys Gly Cys Arg Lys Gly Trp Lys Arg His Gly
            500                 505                 510

Phe Tyr Cys Tyr Leu Ile Gly Ser Thr Leu Ser Thr Phe Thr Asp Ala
        515                 520                 525

Asn His Thr Cys Thr Asn Glu Lys Ala Tyr Leu Thr Thr Val Glu Asp
    530                 535                 540

Arg Tyr Glu Gln Ala Phe Leu Thr Ser Leu Val Gly Leu Arg Pro Glu
545                 550                 555                 560

Lys Tyr Phe Trp Thr Gly Leu Ser Asp Val Gln Asn Lys Gly Thr Phe
                565                 570                 575

Arg Trp Thr Val Asp Glu Gln Val Gln Phe Thr His Trp Asn Ala Asp
            580                 585                 590

Met Pro Gly Arg Lys Ala Gly Cys Val Ala Met Lys Thr Gly Val Ala
        595                 600                 605

Gly Gly Leu Trp Asp Val Leu Ser Cys Glu Glu Lys Ala Lys Phe Val
    610                 615                 620

Cys Lys His Trp Ala Glu Gly Val Thr Arg Pro Pro Glu Pro Thr Thr
625                 630                 635                 640

Thr Pro Glu Pro Lys Cys Pro Glu Asn Trp Gly Thr Thr Ser Lys Thr
                645                 650                 655

Ser Met Cys Phe Lys Leu Tyr Ala Lys Gly Lys His Glu Lys Lys Thr
            660                 665                 670

Trp Phe Glu Ser Arg Asp Phe Cys Lys Ala Ile Gly Gly Glu Leu Ala
        675                 680                 685

Ser Ile Lys Ser Lys Asp Glu Gln Gln Val Ile Trp Arg Leu Ile Thr
    690                 695                 700

Ser Ser Gly Ser Tyr His Glu Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Gly Met Ser Trp Asn Asp Ile Asn
        755                 760                 765

Cys Glu His Leu Asn Asn Trp Ile Cys Gln Ile Gln Lys Gly Lys Thr
    770                 775                 780

Leu Leu Pro Glu Pro Thr Pro Ala Pro Gln Asp Asn Pro Pro Val Thr
785                 790                 795                 800

Ala Asp Gly Trp Val Ile Tyr Lys Asp Tyr Gln Tyr Tyr Phe Ser Lys
                805                 810                 815
```

-continued

```
Glu Lys Glu Thr Met Asp Asn Ala Arg Ala Phe Cys Lys Lys Asn Phe
            820                 825                 830
Gly Asp Leu Ala Thr Ile Lys Ser Glu Ser Glu Lys Lys Phe Leu Trp
            835                 840                 845
Lys Tyr Ile Asn Lys Asn Gly Gly Gln Ser Pro Tyr Phe Ile Gly Met
            850                 855                 860
Leu Ile Ser Met Asp Lys Lys Phe Ile Trp Met Asp Gly Ser Lys Val
865                 870                 875                 880
Asp Phe Val Ala Trp Ala Thr Gly Glu Pro Asn Phe Ala Asn Asp Asp
            885                 890                 895
Glu Asn Cys Val Thr Met Tyr Thr Asn Ser Gly Phe Trp Asn Asp Ile
            900                 905                 910
Asn Cys Gly Tyr Pro Asn Asn Phe Ile Cys Gln Arg His Asn Ser Ser
            915                 920                 925
Ile Asn Ala Thr Ala Met Pro Thr Thr Pro Thr Thr Pro Gly Gly Cys
            930                 935                 940
Lys Glu Gly Trp His Leu Tyr Lys Asn Lys Cys Phe Lys Ile Phe Gly
945                 950                 955                 960
Phe Ala Asn Glu Glu Lys Lys Ser Trp Gln Asp Ala Arg Gln Ala Cys
            965                 970                 975
Lys Gly Leu Lys Gly Asn Leu Val Ser Ile Glu Asn Ala Gln Glu Gln
            980                 985                 990
Ala Phe Val Thr Tyr His Met Arg Asp Ser Thr Phe Asn Ala Trp Thr
            995                 1000                1005
Gly Leu Asn Asp Ile Asn Ala Glu His Met Phe Leu Trp Thr Ala
            1010                1015                1020
Gly Gln Gly Val His Tyr Thr Asn Trp Gly Lys Gly Tyr Pro Gly
            1025                1030                1035
Gly Arg Arg Ser Ser Leu Ser Tyr Glu Asp Ala Asp Cys Val Val
            1040                1045                1050
Val Ile Gly Gly Asn Ser Arg Glu Ala Gly Thr Trp Met Asp Asp
            1055                1060                1065
Thr Cys Asp Ser Lys Gln Gly Tyr Ile Cys Gln Thr Gln Thr Asp
            1070                1075                1080
Pro Ser Leu Pro Val Ser Pro Thr Thr Thr Pro Lys Asp Gly Phe
            1085                1090                1095
Val Thr Tyr Gly Lys Ser Ser Tyr Ser Leu Met Lys Leu Lys Leu
            1100                1105                1110
Pro Trp His Glu Ala Glu Thr Tyr Cys Lys Asp His Thr Ser Leu
            1115                1120                1125
Leu Ala Ser Ile Leu Asp Pro Tyr Ser Asn Ala Phe Ala Trp Met
            1130                1135                1140
Lys Met His Pro Phe Asn Val Pro Ile Trp Ile Ala Leu Asn Ser
            1145                1150                1155
Asn Leu Thr Asn Asn Glu Tyr Thr Trp Thr Asp Arg Trp Arg Val
            1160                1165                1170
Arg Tyr Thr Asn Trp Gly Ala Asp Glu Pro Lys Leu Lys Ser Ala
            1175                1180                1185
Cys Val Tyr Met Asp Val Asp Gly Tyr Trp Arg Thr Ser Tyr Cys
            1190                1195                1200
Asn Glu Ser Phe Tyr Phe Leu Cys Lys Lys Ser Asp Glu Ile Pro
            1205                1210                1215
Ala Thr Glu Pro Pro Gln Leu Pro Gly Lys Cys Pro Glu Ser Glu
```

-continued

```
              1220                1225                1230

Gln Thr Ala Trp Ile Pro Phe Tyr Gly His Cys Tyr Tyr Phe Glu
        1235                1240                1245

Ser Ser Phe Thr Arg Ser Trp Gly Gln Ala Ser Leu Glu Cys Leu
    1250                1255                1260

Arg Met Gly Ala Ser Leu Val Ser Ile Glu Thr Ala Ala Glu Ser
1265                1270                1275

Ser Phe Leu Ser Tyr Arg Val Glu Pro Leu Lys Ser Lys Thr Asn
        1280                1285                1290

Phe Trp Ile Gly Met Phe Arg Asn Val Glu Gly Lys Trp Leu Trp
    1295                1300                1305

Leu Asn Asp Asn Pro Val Ser Phe Val Asn Trp Lys Thr Gly Asp
1310                1315                1320

Pro Ser Gly Glu Arg Asn Asp Cys Val Val Leu Ala Ser Ser Ser
        1325                1330                1335

Gly Leu Trp Asn Asn Ile His Cys Ser Ser Tyr Lys Gly Phe Ile
    1340                1345                1350

Cys Lys Met Pro Lys Ile Ile Asp Pro Val Thr Thr His Ser Ser
1355                1360                1365

Ile Thr Thr Lys Ala Asp Gln Arg Lys Met Asp Pro Gln Pro Lys
        1370                1375                1380

Gly Ser Ser Lys Ala Ala Gly Val Val Thr Val Val Leu Leu Ile
    1385                1390                1395

Val Ile Gly Ala Gly Val Ala Ala Tyr Phe Phe Tyr Lys Lys Arg
1400                1405                1410

His Ala Leu His Ile Pro Gln Glu Ala Thr Phe Glu Asn Thr Leu
        1415                1420                1425

Tyr Phe Asn Ser Asn Leu Ser Pro Gly Thr Ser Asp Thr Lys Asp
    1430                1435                1440

Leu Met Gly Asn Ile Glu Gln Asn Glu His Ala Ile Ile
1445                1450                1455

<210> SEQ ID NO 144
<211> LENGTH: 1376
<212> TYPE: PRT
<213> ORGANISM: Mus musculus

<400> SEQUENCE: 144

Leu Leu Asp Ala Arg Gln Phe Leu Ile Tyr Asn Glu Asp His Lys Arg
1               5                   10                  15

Cys Val Asp Ala Leu Ser Ala Ile Ser Val Gln Thr Ala Thr Cys Asn
                20                  25                  30

Pro Glu Ala Glu Ser Gln Lys Phe Arg Trp Val Ser Asp Ser Gln Ile
        35                  40                  45

Met Ser Val Ala Phe Lys Leu Cys Leu Gly Val Pro Ser Lys Thr Asp
    50                  55                  60

Trp Ala Ser Val Thr Leu Tyr Ala Cys Asp Ser Lys Ser Glu Tyr Gln
65                  70                  75                  80

Lys Trp Glu Cys Lys Asn Asp Thr Leu Phe Gly Ile Lys Gly Thr Glu
                85                  90                  95

Leu Tyr Phe Asn Tyr Gly Asn Arg Gln Glu Lys Asn Ile Lys Leu Tyr
                100                 105                 110

Lys Gly Ser Gly Leu Trp Ser Arg Trp Lys Val Tyr Gly Thr Thr Asp
        115                 120                 125
```

-continued

```
Asp Leu Cys Ser Arg Gly Tyr Glu Ala Met Tyr Ser Leu Leu Gly Asn
130                 135                 140

Ala Asn Gly Ala Val Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Lys Asp Lys Leu Phe Gly Phe Cys Pro
            180                 185                 190

Leu His Phe Glu Gly Ser Glu Arg Leu Trp Asn Lys Asp Pro Leu Thr
        195                 200                 205

Gly Ile Leu Tyr Gln Ile Asn Ser Lys Ser Ala Leu Thr Trp His Gln
210                 215                 220

Ala Arg Ala Ser Cys Lys Gln Gln Asn Ala Asp Leu Leu Ser Val Thr
225                 230                 235                 240

Glu Ile His Glu Gln Met Tyr Leu Thr Gly Leu Thr Ser Ser Leu Ser
                245                 250                 255

Ser Gly Leu Trp Ile Gly Leu Asn Ser Leu Ser Val Arg Ser Gly Trp
            260                 265                 270

Gln Trp Ala Gly Gly Ser Pro Phe Arg Tyr Leu Asn Trp Leu Pro Gly
        275                 280                 285

Ser Pro Ser Ser Glu Pro Gly Lys Ser Cys Val Ser Leu Asn Pro Gly
    290                 295                 300

Lys Asn Ala Lys Trp Glu Asn Leu Glu Cys Val Gln Lys Leu Gly Tyr
305                 310                 315                 320

Ile Cys Lys Lys Gly Asn Asn Thr Leu Asn Pro Phe Ile Ile Pro Ser
                325                 330                 335

Ala Ser Asp Val Pro Thr Gly Cys Pro Asn Gln Trp Trp Pro Tyr Ala
            340                 345                 350

Gly His Cys Tyr Arg Ile His Arg Glu Glu Lys Lys Ile Gln Lys Tyr
        355                 360                 365

Ala Leu Gln Ala Cys Arg Lys Glu Gly Gly Asp Leu Ala Ser Ile His
    370                 375                 380

Ser Ile Glu Glu Phe Asp Phe Ile Phe Ser Gln Leu Gly Tyr Glu Pro
385                 390                 395                 400

Asn Asp Glu Leu Trp Ile Gly Leu Asn Asp Ile Lys Ile Gln Met Tyr
                405                 410                 415

Phe Glu Trp Ser Asp Gly Thr Pro Val Thr Phe Thr Lys Trp Leu Pro
            420                 425                 430

Gly Glu Pro Ser His Glu Asn Asn Arg Gln Glu Asp Cys Val Val Met
        435                 440                 445

Lys Gly Lys Asp Gly Tyr Trp Ala Asp Arg Ala Cys Glu Gln Pro Leu
    450                 455                 460

Gly Tyr Ile Cys Lys Met Val Ser Gln Ser His Ala Val Val Pro Glu
465                 470                 475                 480

Gly Ala Asp Lys Gly Cys Arg Lys Gly Trp Lys Arg His Gly Phe Tyr
                485                 490                 495

Cys Tyr Leu Ile Gly Ser Thr Leu Ser Thr Phe Thr Asp Ala Asn His
            500                 505                 510

Thr Cys Thr Asn Glu Lys Ala Tyr Leu Thr Thr Val Glu Asp Arg Tyr
        515                 520                 525

Glu Gln Ala Phe Leu Thr Ser Leu Val Gly Leu Arg Pro Glu Lys Tyr
    530                 535                 540

Phe Trp Thr Gly Leu Ser Asp Val Gln Asn Lys Gly Thr Phe Arg Trp
```

```
            545                 550                 555                 560
        Thr Val Asp Glu Gln Val Gln Phe Thr His Trp Asn Ala Asp Met Pro
                        565                 570                 575
        Gly Arg Lys Ala Gly Cys Val Ala Met Lys Thr Gly Val Ala Gly Gly
                        580                 585                 590
        Leu Trp Asp Val Leu Ser Cys Glu Glu Lys Ala Lys Phe Val Cys Lys
                        595                 600                 605
        His Trp Ala Glu Gly Val Thr Arg Pro Pro Glu Pro Thr Thr Thr Pro
                        610                 615                 620
        Glu Pro Lys Cys Pro Glu Asn Trp Gly Thr Thr Ser Lys Thr Ser Met
        625                 630                 635                 640
        Cys Phe Lys Leu Tyr Ala Lys Gly Lys His Glu Lys Lys Thr Trp Phe
                        645                 650                 655
        Glu Ser Arg Asp Phe Cys Lys Ala Ile Gly Gly Glu Leu Ala Ser Ile
                        660                 665                 670
        Lys Ser Lys Asp Glu Gln Gln Val Ile Trp Arg Leu Ile Thr Ser Ser
                        675                 680                 685
        Gly Ser Tyr His Glu Leu Phe Trp Leu Gly Leu Thr Tyr Gly Ser Pro
                        690                 695                 700
        Ser Glu Gly Phe Thr Trp Ser Asp Gly Ser Pro Val Ser Tyr Glu Asn
        705                 710                 715                 720
        Trp Ala Tyr Gly Glu Pro Asn Asn Tyr Gln Asn Val Glu Tyr Cys Gly
                        725                 730                 735
        Glu Leu Lys Gly Asp Pro Gly Met Ser Trp Asn Asp Ile Asn Cys Glu
                        740                 745                 750
        His Leu Asn Asn Trp Ile Cys Gln Ile Gln Lys Gly Lys Thr Leu Leu
                        755                 760                 765
        Pro Glu Pro Thr Pro Ala Pro Gln Asp Asn Pro Pro Val Thr Ala Asp
                        770                 775                 780
        Gly Trp Val Ile Tyr Lys Asp Tyr Gln Tyr Tyr Phe Ser Lys Glu Lys
        785                 790                 795                 800
        Glu Thr Met Asp Asn Ala Arg Ala Phe Cys Lys Lys Asn Phe Gly Asp
                        805                 810                 815
        Leu Ala Thr Ile Lys Ser Glu Ser Glu Lys Lys Phe Leu Trp Lys Tyr
                        820                 825                 830
        Ile Asn Lys Asn Gly Gly Gln Ser Pro Tyr Phe Ile Gly Met Leu Ile
                        835                 840                 845
        Ser Met Asp Lys Lys Phe Ile Trp Met Asp Gly Ser Lys Val Asp Phe
        850                 855                 860
        Val Ala Trp Ala Thr Gly Glu Pro Asn Phe Ala Asn Asp Asp Glu Asn
        865                 870                 875                 880
        Cys Val Thr Met Tyr Thr Asn Ser Gly Phe Trp Asn Asp Ile Asn Cys
                        885                 890                 895
        Gly Tyr Pro Asn Asn Phe Ile Cys Gln Arg His Asn Ser Ser Ile Asn
                        900                 905                 910
        Ala Thr Ala Met Pro Thr Thr Pro Thr Thr Pro Gly Gly Cys Lys Glu
                        915                 920                 925
        Gly Trp His Leu Tyr Lys Asn Lys Cys Phe Lys Ile Phe Gly Phe Ala
                        930                 935                 940
        Asn Glu Glu Lys Lys Ser Trp Gln Asp Ala Arg Gln Ala Cys Lys Gly
        945                 950                 955                 960
        Leu Lys Gly Asn Leu Val Ser Ile Glu Asn Ala Gln Glu Gln Ala Phe
                        965                 970                 975
```

-continued

Val Thr Tyr His Met Arg Asp Ser Thr Phe Asn Ala Trp Thr Gly Leu
            980                 985                 990

Asn Asp Ile Asn Ala Glu His Met Phe Leu Trp Thr Ala Gly Gln Gly
            995                 1000                1005

Val His Tyr Thr Asn Trp Gly Lys Gly Tyr Pro Gly Gly Arg Arg
    1010                1015                1020

Ser Ser Leu Ser Tyr Glu Asp Ala Asp Cys Val Val Val Ile Gly
    1025                1030                1035

Gly Asn Ser Arg Glu Ala Gly Thr Trp Met Asp Asp Thr Cys Asp
    1040                1045                1050

Ser Lys Gln Gly Tyr Ile Cys Gln Thr Gln Thr Asp Pro Ser Leu
    1055                1060                1065

Pro Val Ser Pro Thr Thr Thr Pro Lys Asp Gly Phe Val Thr Tyr
    1070                1075                1080

Gly Lys Ser Ser Tyr Ser Leu Met Lys Leu Lys Leu Pro Trp His
    1085                1090                1095

Glu Ala Glu Thr Tyr Cys Lys Asp His Thr Ser Leu Leu Ala Ser
    1100                1105                1110

Ile Leu Asp Pro Tyr Ser Asn Ala Phe Ala Trp Met Lys Met His
    1115                1120                1125

Pro Phe Asn Val Pro Ile Trp Ile Ala Leu Asn Ser Asn Leu Thr
    1130                1135                1140

Asn Asn Glu Tyr Thr Trp Thr Asp Arg Trp Arg Val Arg Tyr Thr
    1145                1150                1155

Asn Trp Gly Ala Asp Glu Pro Lys Leu Lys Ser Ala Cys Val Tyr
    1160                1165                1170

Met Asp Val Asp Gly Tyr Trp Arg Thr Ser Tyr Cys Asn Glu Ser
    1175                1180                1185

Phe Tyr Phe Leu Cys Lys Lys Ser Asp Glu Ile Pro Ala Thr Glu
    1190                1195                1200

Pro Pro Gln Leu Pro Gly Lys Cys Pro Glu Ser Glu Gln Thr Ala
    1205                1210                1215

Trp Ile Pro Phe Tyr Gly His Cys Tyr Tyr Phe Glu Ser Ser Phe
    1220                1225                1230

Thr Arg Ser Trp Gly Gln Ala Ser Leu Glu Cys Leu Arg Met Gly
    1235                1240                1245

Ala Ser Leu Val Ser Ile Glu Thr Ala Ala Glu Ser Ser Phe Leu
    1250                1255                1260

Ser Tyr Arg Val Glu Pro Leu Lys Ser Lys Thr Asn Phe Trp Ile
    1265                1270                1275

Gly Met Phe Arg Asn Val Glu Gly Lys Trp Leu Trp Leu Asn Asp
    1280                1285                1290

Asn Pro Val Ser Phe Val Asn Trp Lys Thr Gly Asp Pro Ser Gly
    1295                1300                1305

Glu Arg Asn Asp Cys Val Val Leu Ala Ser Ser Ser Gly Leu Trp
    1310                1315                1320

Asn Asn Ile His Cys Ser Ser Tyr Lys Gly Phe Ile Cys Lys Met
    1325                1330                1335

Pro Lys Ile Ile Asp Pro Val Thr Thr His Ser Ser Ile Thr Thr
    1340                1345                1350

Lys Ala Asp Gln Arg Lys Met Asp Pro Gln Pro Lys Gly Ser Ser
    1355                1360                1365

```
Lys Ala His His His His His His
    1370            1375

<210> SEQ ID NO 145
<211> LENGTH: 1365
<212> TYPE: PRT
<213> ORGANISM: Homo sapiens

<400> SEQUENCE: 145

Leu Leu Asp Thr Arg Gln Phe Leu Ile Tyr Asn Glu Asp His Lys Arg
1               5                   10                  15

Cys Val Asp Ala Val Ser Pro Ser Ala Val Gln Thr Ala Ala Cys Asn
            20                  25                  30

Gln Asp Ala Glu Ser Gln Lys Phe Arg Trp Val Ser Glu Ser Gln Ile
        35                  40                  45

Met Ser Val Ala Phe Lys Leu Cys Leu Gly Val Pro Ser Lys Thr Asp
    50                  55                  60

Trp Val Ala Ile Thr Leu Tyr Ala Cys Asp Ser Lys Ser Glu Phe Gln
65                  70                  75                  80

Lys Trp Glu Cys Lys Asn Asp Thr Leu Leu Gly Ile Lys Gly Glu Asp
                85                  90                  95

Leu Phe Phe Asn Tyr Gly Asn Arg Gln Glu Lys Asn Ile Met Leu Tyr
            100                 105                 110

Lys Gly Ser Gly Leu Trp Ser Arg Trp Lys Ile Tyr Gly Thr Thr Asp
        115                 120                 125

Asn Leu Cys Ser Arg Gly Tyr Glu Ala Met Tyr Thr Leu Leu Gly Asn
    130                 135                 140

Ala Asn Gly Ala Thr Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Thr Asp Lys Leu Phe Gly Tyr Cys Pro
            180                 185                 190

Leu Lys Phe Glu Gly Ser Glu Ser Leu Trp Asn Lys Asp Pro Leu Thr
        195                 200                 205

Ser Val Ser Tyr Gln Ile Asn Ser Lys Ser Ala Leu Thr Trp His Gln
    210                 215                 220

Ala Arg Lys Ser Cys Gln Gln Asn Ala Glu Leu Leu Ser Ile Thr
225                 230                 235                 240

Glu Ile His Glu Gln Thr Tyr Leu Thr Gly Leu Thr Ser Ser Leu Thr
                245                 250                 255

Ser Gly Leu Trp Ile Gly Leu Asn Ser Leu Ser Phe Asn Ser Gly Trp
            260                 265                 270

Gln Trp Ser Asp Arg Ser Pro Phe Arg Tyr Leu Asn Trp Leu Pro Gly
        275                 280                 285

Ser Pro Ser Ala Glu Pro Gly Lys Ser Cys Val Ser Leu Asn Pro Gly
    290                 295                 300

Lys Asn Ala Lys Trp Glu Asn Leu Glu Cys Val Gln Lys Leu Gly Tyr
305                 310                 315                 320

Ile Cys Lys Lys Gly Asn Thr Thr Leu Asn Ser Phe Val Ile Pro Ser
                325                 330                 335

Glu Ser Asp Val Pro Thr His Cys Pro Ser Gln Trp Trp Pro Tyr Ala
            340                 345                 350

Gly His Cys Tyr Lys Ile His Arg Asp Glu Lys Lys Ile Gln Arg Asp
        355                 360                 365
```

```
Ala Leu Thr Thr Cys Arg Lys Glu Gly Gly Asp Leu Thr Ser Ile His
    370                 375                 380

Thr Ile Glu Glu Leu Asp Phe Ile Ile Ser Gln Leu Gly Tyr Glu Pro
385                 390                 395                 400

Asn Asp Glu Leu Trp Ile Gly Leu Asn Asp Ile Lys Ile Gln Met Tyr
                405                 410                 415

Phe Glu Trp Ser Asp Gly Thr Pro Val Thr Phe Thr Lys Trp Leu Arg
            420                 425                 430

Gly Glu Pro Ser His Glu Asn Asn Arg Gln Glu Asp Cys Val Val Met
        435                 440                 445

Lys Gly Lys Asp Gly Tyr Trp Ala Asp Arg Gly Cys Glu Trp Pro Leu
    450                 455                 460

Gly Tyr Ile Cys Lys Met Lys Ser Arg Ser Gln Gly Pro Glu Ile Val
465                 470                 475                 480

Glu Val Glu Lys Gly Cys Arg Lys Gly Trp Lys Lys His His Phe Tyr
                485                 490                 495

Cys Tyr Met Ile Gly His Thr Leu Ser Thr Phe Ala Glu Ala Asn Gln
            500                 505                 510

Thr Cys Asn Asn Glu Asn Ala Tyr Leu Thr Thr Ile Glu Asp Arg Tyr
        515                 520                 525

Glu Gln Ala Phe Leu Thr Ser Phe Val Gly Leu Arg Pro Glu Lys Tyr
    530                 535                 540

Phe Trp Thr Gly Leu Ser Asp Ile Gln Thr Lys Gly Thr Phe Gln Trp
545                 550                 555                 560

Thr Ile Glu Glu Glu Val Arg Phe Thr His Trp Asn Ser Asp Met Pro
                565                 570                 575

Gly Arg Lys Pro Gly Cys Val Ala Met Arg Thr Gly Ile Ala Gly Gly
            580                 585                 590

Leu Trp Asp Val Leu Lys Cys Asp Glu Lys Ala Lys Phe Val Cys Lys
        595                 600                 605

His Trp Ala Glu Gly Val Thr His Pro Pro Lys Pro Thr Thr Thr Pro
    610                 615                 620

Glu Pro Lys Cys Pro Glu Asp Trp Gly Ala Ser Ser Arg Thr Ser Leu
625                 630                 635                 640

Cys Phe Lys Leu Tyr Ala Lys Gly Lys His Glu Lys Lys Thr Trp Phe
                645                 650                 655

Glu Ser Arg Asp Phe Cys Arg Ala Leu Gly Gly Asp Leu Ala Ser Ile
            660                 665                 670

Asn Asn Lys Glu Glu Gln Gln Thr Ile Trp Arg Leu Ile Thr Ala Ser
        675                 680                 685

Gly Ser Tyr His Lys Leu Phe Trp Leu Gly Leu Thr Tyr Gly Ser Pro
    690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Thr Met Ser Trp Asn Asp Ile Asn Cys Glu
            740                 745                 750

His Leu Asn Asn Trp Ile Cys Gln Ile Gln Lys Gly Gln Thr Pro Lys
        755                 760                 765

Pro Glu Pro Thr Pro Ala Pro Gln Asp Asn Pro Pro Val Thr Glu Asp
    770                 775                 780
```

```
Gly Trp Val Ile Tyr Lys Asp Tyr Gln Tyr Tyr Phe Ser Lys Glu Lys
785                 790                 795                 800

Glu Thr Met Asp Asn Ala Arg Ala Phe Cys Lys Arg Asn Phe Gly Asp
            805                 810                 815

Leu Val Ser Ile Gln Ser Glu Ser Lys Lys Phe Leu Trp Lys Tyr
        820                 825                 830

Val Asn Arg Asn Asp Ala Gln Ser Ala Tyr Phe Ile Gly Leu Leu Ile
            835                 840                 845

Ser Leu Asp Lys Lys Phe Ala Trp Met Asp Gly Ser Lys Val Asp Tyr
    850                 855                 860

Val Ser Trp Ala Thr Gly Glu Pro Asn Phe Ala Asn Glu Asp Glu Asn
865                 870                 875                 880

Cys Val Thr Met Tyr Ser Asn Ser Gly Phe Trp Asn Asp Ile Asn Cys
                885                 890                 895

Gly Tyr Pro Asn Ala Phe Ile Cys Gln Arg His Asn Ser Ser Ile Asn
            900                 905                 910

Ala Thr Thr Val Met Pro Thr Met Pro Ser Val Pro Ser Gly Cys Lys
            915                 920                 925

Glu Gly Trp Asn Phe Tyr Ser Asn Lys Cys Phe Lys Ile Phe Gly Phe
            930                 935                 940

Met Glu Glu Glu Arg Lys Asn Trp Gln Glu Ala Arg Lys Ala Cys Ile
945                 950                 955                 960

Gly Phe Gly Gly Asn Leu Val Ser Ile Gln Asn Glu Lys Glu Gln Ala
                965                 970                 975

Phe Leu Thr Tyr His Met Lys Asp Ser Thr Phe Ser Ala Trp Thr Gly
            980                 985                 990

Leu Asn Asp Val Asn Ser Glu His Thr Phe Leu Trp Thr Asp Gly Arg
            995                 1000                1005

Gly Val His Tyr Thr Asn Trp Gly Lys Gly Tyr Pro Gly Gly Arg
    1010                1015                1020

Arg Ser Ser Leu Ser Tyr Glu Asp Ala Asp Cys Val Val Ile Ile
    1025                1030                1035

Gly Gly Ala Ser Asn Glu Ala Gly Lys Trp Met Asp Asp Thr Cys
    1040                1045                1050

Asp Ser Lys Arg Gly Tyr Ile Cys Gln Thr Arg Ser Asp Pro Ser
    1055                1060                1065

Leu Thr Asn Pro Pro Ala Thr Ile Gln Thr Asp Gly Phe Val Lys
    1070                1075                1080

Tyr Gly Lys Ser Ser Tyr Ser Leu Met Arg Gln Lys Phe Gln Trp
    1085                1090                1095

His Glu Ala Glu Thr Tyr Cys Lys Leu His Asn Ser Leu Ile Ala
    1100                1105                1110

Ser Ile Leu Asp Pro Tyr Ser Asn Ala Phe Ala Trp Leu Gln Met
    1115                1120                1125

Glu Thr Ser Asn Glu Arg Val Trp Ile Ala Leu Asn Ser Asn Leu
    1130                1135                1140

Thr Asp Asn Gln Tyr Thr Trp Thr Asp Lys Trp Arg Val Arg Tyr
    1145                1150                1155

Thr Asn Trp Ala Ala Asp Glu Pro Lys Leu Lys Ser Ala Cys Val
    1160                1165                1170

Tyr Leu Asp Leu Asp Gly Tyr Trp Lys Thr Ala His Cys Asn Glu
    1175                1180                1185

Ser Phe Tyr Phe Leu Cys Lys Arg Ser Asp Glu Ile Pro Ala Thr
```

```
            1190                1195                1200
Glu Pro Pro Gln Leu Pro Gly Arg Cys Pro Ser Asp His Thr
    1205                1210                1215
Ala Trp Ile Pro Phe His Gly His Cys Tyr Tyr Ile Glu Ser Ser
    1220                1225                1230
Tyr Thr Arg Asn Trp Gly Gln Ala Ser Leu Glu Cys Leu Arg Met
    1235                1240                1245
Gly Ser Ser Leu Val Ser Ile Glu Ser Ala Ala Glu Ser Ser Phe
    1250                1255                1260
Leu Ser Tyr Arg Val Glu Pro Leu Lys Ser Lys Thr Asn Phe Trp
    1265                1270                1275
Ile Gly Leu Phe Arg Asn Val Glu Gly Thr Trp Leu Trp Ile Asn
    1280                1285                1290
Asn Ser Pro Val Ser Phe Val Asn Trp Asn Thr Gly Asp Pro Ser
    1295                1300                1305
Gly Glu Arg Asn Asp Cys Val Ala Leu His Ala Ser Ser Gly Phe
    1310                1315                1320
Trp Ser Asn Ile His Cys Ser Ser Tyr Lys Gly Tyr Ile Cys Lys
    1325                1330                1335
Arg Pro Lys Ile Ile Asp Ala Lys Pro Thr His Glu Leu Leu Thr
    1340                1345                1350
Thr Lys Ala Asp Thr Arg Lys Met Asp Pro Ser Lys
    1355                1360                1365

<210> SEQ ID NO 146
<211> LENGTH: 1370
<212> TYPE: PRT
<213> ORGANISM: Mus musculus

<400> SEQUENCE: 146

Leu Leu Asp Ala Arg Gln Phe Leu Ile Tyr Asn Glu Asp His Lys Arg
1               5                   10                  15
Cys Val Asp Ala Leu Ser Ala Ile Ser Val Gln Thr Ala Thr Cys Asn
                20                  25                  30
Pro Glu Ala Glu Ser Gln Lys Phe Arg Trp Val Ser Asp Ser Gln Ile
        35                  40                  45
Met Ser Val Ala Phe Lys Leu Cys Leu Gly Val Pro Ser Lys Thr Asp
    50                  55                  60
Trp Ala Ser Val Thr Leu Tyr Ala Cys Asp Ser Lys Ser Glu Tyr Gln
65                  70                  75                  80
Lys Trp Glu Cys Lys Asn Asp Thr Leu Phe Gly Ile Lys Gly Thr Glu
                85                  90                  95
Leu Tyr Phe Asn Tyr Gly Asn Arg Gln Glu Lys Asn Ile Lys Leu Tyr
                100                 105                 110
Lys Gly Ser Gly Leu Trp Ser Arg Trp Lys Val Tyr Gly Thr Thr Asp
        115                 120                 125
Asp Leu Cys Ser Arg Gly Tyr Glu Ala Met Tyr Ser Leu Leu Gly Asn
    130                 135                 140
Ala Asn Gly Ala Val Cys Ala Phe Pro Phe Lys Phe Glu Asn Lys Trp
145                 150                 155                 160
Tyr Ala Asp Cys Thr Ser Ala Gly Arg Ser Asp Gly Trp Leu Trp Cys
                165                 170                 175
Gly Thr Thr Thr Asp Tyr Asp Lys Asp Lys Leu Phe Gly Phe Cys Pro
                180                 185                 190
```

```
Leu His Phe Glu Gly Ser Glu Arg Leu Trp Asn Lys Asp Pro Leu Thr
            195                 200                 205

Gly Ile Leu Tyr Gln Ile Asn Ser Lys Ser Ala Leu Thr Trp His Gln
210                 215                 220

Ala Arg Ala Ser Cys Lys Gln Gln Asn Ala Asp Leu Leu Ser Val Thr
225                 230                 235                 240

Glu Ile His Glu Gln Met Tyr Leu Thr Gly Leu Thr Ser Ser Leu Ser
                245                 250                 255

Ser Gly Leu Trp Ile Gly Leu Asn Ser Leu Ser Val Arg Ser Gly Trp
            260                 265                 270

Gln Trp Ala Gly Gly Ser Pro Phe Arg Tyr Leu Asn Trp Leu Pro Gly
        275                 280                 285

Ser Pro Ser Ser Glu Pro Gly Lys Ser Cys Val Ser Leu Asn Pro Gly
    290                 295                 300

Lys Asn Ala Lys Trp Glu Asn Leu Glu Cys Val Gln Lys Leu Gly Tyr
305                 310                 315                 320

Ile Cys Lys Lys Gly Asn Asn Thr Leu Asn Pro Phe Ile Ile Pro Ser
                325                 330                 335

Ala Ser Asp Val Pro Thr Gly Cys Pro Asn Gln Trp Trp Pro Tyr Ala
            340                 345                 350

Gly His Cys Tyr Arg Ile His Arg Glu Glu Lys Lys Ile Gln Lys Tyr
        355                 360                 365

Ala Leu Gln Ala Cys Arg Lys Glu Gly Gly Asp Leu Ala Ser Ile His
    370                 375                 380

Ser Ile Glu Glu Phe Asp Phe Ile Phe Ser Gln Leu Gly Tyr Glu Pro
385                 390                 395                 400

Asn Asp Glu Leu Trp Ile Gly Leu Asn Asp Ile Lys Ile Gln Met Tyr
                405                 410                 415

Phe Glu Trp Ser Asp Gly Thr Pro Val Thr Phe Thr Lys Trp Leu Pro
            420                 425                 430

Gly Glu Pro Ser His Glu Asn Asn Arg Gln Glu Asp Cys Val Val Met
        435                 440                 445

Lys Gly Lys Asp Gly Tyr Trp Ala Asp Arg Ala Cys Glu Gln Pro Leu
450                 455                 460

Gly Tyr Ile Cys Lys Met Val Ser Gln Ser His Ala Val Pro Glu
465                 470                 475                 480

Gly Ala Asp Lys Gly Cys Arg Lys Gly Trp Lys Arg His Gly Phe Tyr
                485                 490                 495

Cys Tyr Leu Ile Gly Ser Thr Leu Ser Thr Phe Thr Asp Ala Asn His
            500                 505                 510

Thr Cys Thr Asn Glu Lys Ala Tyr Leu Thr Thr Val Glu Asp Arg Tyr
        515                 520                 525

Glu Gln Ala Phe Leu Thr Ser Leu Val Gly Leu Arg Pro Glu Lys Tyr
    530                 535                 540

Phe Trp Thr Gly Leu Ser Asp Val Gln Asn Lys Gly Thr Phe Arg Trp
545                 550                 555                 560

Thr Val Asp Glu Gln Val Gln Phe Thr His Trp Asn Ala Asp Met Pro
                565                 570                 575

Gly Arg Lys Ala Gly Cys Val Ala Met Lys Thr Gly Val Ala Gly Gly
            580                 585                 590

Leu Trp Asp Val Leu Ser Cys Glu Glu Lys Ala Lys Phe Val Cys Lys
        595                 600                 605

His Trp Ala Glu Gly Val Thr Arg Pro Pro Glu Pro Thr Thr Thr Pro
```

```
              610              615              620
Glu Pro Lys Cys Pro Glu Asn Trp Gly Thr Thr Ser Lys Thr Ser Met
625              630              635              640

Cys Phe Lys Leu Tyr Ala Lys Gly Lys His Glu Lys Lys Thr Trp Phe
             645              650              655

Glu Ser Arg Asp Phe Cys Lys Ala Ile Gly Gly Glu Leu Ala Ser Ile
             660              665              670

Lys Ser Lys Asp Glu Gln Gln Val Ile Trp Arg Leu Ile Thr Ser Ser
             675              680              685

Gly Ser Tyr His Glu Leu Phe Trp Leu Gly Leu Thr Tyr Gly Ser Pro
             690              695              700

Ser Glu Gly Phe Thr Trp Ser Asp Gly Ser Pro Val Ser Tyr Glu Asn
705              710              715              720

Trp Ala Tyr Gly Glu Pro Asn Asn Tyr Gln Asn Val Glu Tyr Cys Gly
             725              730              735

Glu Leu Lys Gly Asp Pro Gly Met Ser Trp Asn Asp Ile Asn Cys Glu
             740              745              750

His Leu Asn Asn Trp Ile Cys Gln Ile Gln Lys Gly Lys Thr Leu Leu
             755              760              765

Pro Glu Pro Thr Pro Ala Pro Gln Asp Asn Pro Pro Val Thr Ala Asp
             770              775              780

Gly Trp Val Ile Tyr Lys Asp Tyr Gln Tyr Tyr Phe Ser Lys Glu Lys
785              790              795              800

Glu Thr Met Asp Asn Ala Arg Ala Phe Cys Lys Lys Asn Phe Gly Asp
             805              810              815

Leu Ala Thr Ile Lys Ser Glu Ser Glu Lys Lys Phe Leu Trp Lys Tyr
             820              825              830

Ile Asn Lys Asn Gly Gly Gln Ser Pro Tyr Phe Ile Gly Met Leu Ile
             835              840              845

Ser Met Asp Lys Lys Phe Ile Trp Met Asp Gly Ser Lys Val Asp Phe
             850              855              860

Val Ala Trp Ala Thr Gly Glu Pro Asn Phe Ala Asn Asp Asp Glu Asn
865              870              875              880

Cys Val Thr Met Tyr Thr Asn Ser Gly Phe Trp Asn Asp Ile Asn Cys
             885              890              895

Gly Tyr Pro Asn Asn Phe Ile Cys Gln Arg His Asn Ser Ser Ile Asn
             900              905              910

Ala Thr Ala Met Pro Thr Thr Pro Thr Thr Pro Gly Gly Cys Lys Glu
             915              920              925

Gly Trp His Leu Tyr Lys Asn Lys Cys Phe Lys Ile Phe Gly Phe Ala
930              935              940

Asn Glu Glu Lys Lys Ser Trp Gln Asp Ala Arg Gln Ala Cys Lys Gly
945              950              955              960

Leu Lys Gly Asn Leu Val Ser Ile Glu Asn Ala Gln Glu Gln Ala Phe
             965              970              975

Val Thr Tyr His Met Arg Asp Ser Thr Phe Asn Ala Trp Thr Gly Leu
             980              985              990

Asn Asp Ile Asn Ala Glu His Met Phe Leu Trp Thr Ala Gly Gln Gly
             995              1000             1005

Val His Tyr Thr Asn Trp Gly Lys Gly Tyr Pro Gly Gly Arg Arg
   1010             1015             1020

Ser Ser Leu Ser Tyr Glu Asp Ala Asp Cys Val Val Val Ile Gly
   1025             1030             1035
```

Gly Asn Ser Arg Glu Ala Gly Thr Trp Met Asp Asp Thr Cys Asp
1040                1045                1050

Ser Lys Gln Gly Tyr Ile Cys Gln Thr Gln Thr Asp Pro Ser Leu
    1055                1060                1065

Pro Val Ser Pro Thr Thr Thr Pro Lys Asp Gly Phe Val Thr Tyr
    1070                1075                1080

Gly Lys Ser Ser Tyr Ser Leu Met Lys Leu Lys Leu Pro Trp His
    1085                1090                1095

Glu Ala Glu Thr Tyr Cys Lys Asp His Thr Ser Leu Leu Ala Ser
    1100                1105                1110

Ile Leu Asp Pro Tyr Ser Asn Ala Phe Ala Trp Met Lys Met His
    1115                1120                1125

Pro Phe Asn Val Pro Ile Trp Ile Ala Leu Asn Ser Asn Leu Thr
    1130                1135                1140

Asn Asn Glu Tyr Thr Trp Thr Asp Arg Trp Arg Val Arg Tyr Thr
    1145                1150                1155

Asn Trp Gly Ala Asp Glu Pro Lys Leu Lys Ser Ala Cys Val Tyr
    1160                1165                1170

Met Asp Val Asp Gly Tyr Trp Arg Thr Ser Tyr Cys Asn Glu Ser
    1175                1180                1185

Phe Tyr Phe Leu Cys Lys Lys Ser Asp Glu Ile Pro Ala Thr Glu
    1190                1195                1200

Pro Pro Gln Leu Pro Gly Lys Cys Pro Glu Ser Glu Gln Thr Ala
    1205                1210                1215

Trp Ile Pro Phe Tyr Gly His Cys Tyr Tyr Phe Glu Ser Ser Phe
    1220                1225                1230

Thr Arg Ser Trp Gly Gln Ala Ser Leu Glu Cys Leu Arg Met Gly
    1235                1240                1245

Ala Ser Leu Val Ser Ile Glu Thr Ala Ala Glu Ser Ser Phe Leu
    1250                1255                1260

Ser Tyr Arg Val Glu Pro Leu Lys Ser Lys Thr Asn Phe Trp Ile
    1265                1270                1275

Gly Met Phe Arg Asn Val Glu Gly Lys Trp Leu Trp Leu Asn Asp
    1280                1285                1290

Asn Pro Val Ser Phe Val Asn Trp Lys Thr Gly Asp Pro Ser Gly
    1295                1300                1305

Glu Arg Asn Asp Cys Val Val Leu Ala Ser Ser Ser Gly Leu Trp
    1310                1315                1320

Asn Asn Ile His Cys Ser Ser Tyr Lys Gly Phe Ile Cys Lys Met
    1325                1330                1335

Pro Lys Ile Ile Asp Pro Val Thr Thr His Ser Ser Ile Thr Thr
    1340                1345                1350

Lys Ala Asp Gln Arg Lys Met Asp Pro Gln Pro Lys Gly Ser Ser
    1355                1360                1365

Lys Ala
    1370

<210> SEQ ID NO 147
<211> LENGTH: 1463
<212> TYPE: PRT
<213> ORGANISM: Rattus norvegicus

<400> SEQUENCE: 147

Met Glu His Thr Leu Trp Ala Met Arg Leu Pro Leu Leu Leu Ala Phe

-continued

```
1               5                   10                  15
Ile Ser Val Ile Pro Val Ala Val Gln Leu Leu Asp Ser Arg Gln Phe
             20                  25                  30
Leu Ile Tyr Asn Glu Asp His Lys Arg Cys Val Asp Ala Leu Ser Ala
             35                  40                  45
Ile Ser Val Gln Thr Ala Thr Cys Asn Pro Glu Ala Glu Ser Gln Lys
             50                  55                  60
Phe Arg Trp Val Ser Glu Ser Gln Ile Met Ser Val Ala Phe Lys Leu
65                   70                  75                  80
Cys Leu Gly Val Pro Ser Lys Thr Asp Trp Ala Ser Val Thr Leu Tyr
             85                  90                  95
Ala Cys Asp Ser Lys Ser Glu Phe Gln Lys Trp Glu Cys Lys Asn Asp
             100                 105                 110
Thr Leu Phe Gly Ile Lys Gly Thr Glu Leu Tyr Phe Asn Tyr Gly Asn
             115                 120                 125
Arg Gln Glu Lys Asn Ile Lys Leu Tyr Lys Gly Ser Gly Leu Trp Ser
             130                 135                 140
Arg Trp Lys Val Tyr Gly Thr Thr Asp Asp Leu Cys Ser Arg Gly Tyr
145                  150                 155                 160
Glu Ala Met Tyr Ser Leu Leu Gly Asn Ala Asn Gly Ala Val Cys Ala
             165                 170                 175
Phe Pro Phe Lys Phe Glu Asn Lys Trp Tyr Ala Asp Cys Thr Ser Ala
             180                 185                 190
Gly Arg Ser Asp Gly Trp Leu Trp Cys Gly Thr Thr Thr Asp Tyr Asp
             195                 200                 205
Thr Asp Lys Leu Phe Gly Phe Cys Pro Leu Gln Phe Glu Gly Ser Lys
             210                 215                 220
Arg Leu Trp Asn Thr Asp Pro Leu Thr Gly Ile Leu Tyr Gln Ile Asn
225                  230                 235                 240
Ser Lys Ser Ala Leu Thr Trp His Gln Ala Arg Ala Ser Cys Lys Gln
             245                 250                 255
Gln Asn Ala Glu Leu Leu Ser Val Thr Glu Ile His Glu Gln Met Tyr
             260                 265                 270
Leu Thr Gly Leu Thr Ser Ser Leu Thr Ser Gly Leu Trp Ile Gly Leu
             275                 280                 285
Asn Ser Leu Ser Leu Ser Thr Gly Trp Gln Trp Ala Gly Gly Ser Pro
             290                 295                 300
Phe Arg Tyr Leu Asn Trp Leu Pro Gly Ser Pro Ser Ser Glu Pro Gly
305                  310                 315                 320
Lys Ser Cys Val Ser Leu Asn Pro Gly Lys Asn Ala Lys Trp Glu Asn
             325                 330                 335
Leu Glu Cys Val Gln Lys Leu Gly Tyr Ile Cys Lys Lys Gly Asn Asn
             340                 345                 350
Thr Leu Asn Pro Phe Ile Ile Pro Ser Glu Ser Asp Val Pro Thr Ala
             355                 360                 365
Cys Pro Asn Gln Trp Trp Pro Tyr Ala Gly His Cys Tyr Arg Ile Tyr
             370                 375                 380
Arg Glu Glu Lys Lys Ile Gln Lys Tyr Ala Leu Gln Ala Cys Arg Lys
385                  390                 395                 400
Glu Gly Gly Asp Leu Ala Ser Ile His Ser Ile Glu Glu Phe Asp Phe
             405                 410                 415
Ile Phe Ser Gln Leu Gly Tyr Glu Pro Asn Asp Glu Leu Trp Ile Gly
             420                 425                 430
```

```
Leu Asn Asp Ile Lys Ile Gln Met Tyr Phe Glu Trp Ser Asp Gly Thr
        435                 440                 445

Pro Val Thr Phe Thr Lys Trp Leu Pro Gly Glu Pro Ser His Glu Asn
450                 455                 460

Asn Arg Gln Glu Asp Cys Val Val Met Lys Gly Lys Asp Gly Tyr Trp
465                 470                 475                 480

Ala Asp Arg Ala Cys Glu Gln Pro Leu Gly Tyr Ile Cys Lys Met Val
            485                 490                 495

Ser Gln Ile His Thr Val Ile Pro Glu Gly Ala Glu Lys Gly Cys Arg
        500                 505                 510

Lys Gly Trp Lys Arg His Gly Phe Tyr Cys Tyr Leu Ile Gly Ser Thr
        515                 520                 525

Leu Ser Thr Phe Ala Asp Ala Asn Gln Thr Cys Thr Asn Glu Lys Ala
530                 535                 540

Tyr Leu Thr Thr Val Glu Asp Arg Tyr Glu Gln Ala Phe Leu Thr Ser
545                 550                 555                 560

Leu Val Gly Leu Arg Pro Glu Lys Tyr Phe Trp Thr Gly Leu Ser Asp
            565                 570                 575

Val Gln Asn Lys Gly Thr Phe Arg Trp Thr Val Asp Glu Gln Val Gln
        580                 585                 590

Phe Thr His Trp Asn Ala Asp Met Pro Gly Arg Lys Ala Gly Cys Val
        595                 600                 605

Ala Met Lys Thr Gly Val Ala Gly Gly Leu Trp Asp Val Leu Ser Cys
610                 615                 620

Glu Glu Lys Ala Lys Phe Val Cys Lys His Trp Ala Glu Gly Val Thr
625                 630                 635                 640

Arg Pro Pro Glu Pro Thr Thr Pro Glu Pro Lys Cys Pro Glu Asp
            645                 650                 655

Trp Gly Thr Thr Ser Lys Thr Ser Met Cys Phe Lys Leu Tyr Ala Lys
            660                 665                 670

Gly Lys His Glu Lys Lys Thr Trp Phe Glu Ser Arg Asp Phe Cys Lys
        675                 680                 685

Ala Ile Gly Gly Glu Leu Ala Ser Ile Lys Ser Lys Asp Glu Gln Gln
        690                 695                 700

Val Ile Trp Arg Leu Ile Thr Ser Ser Gly Ser Tyr His Glu Leu Phe
705                 710                 715                 720

Trp Leu Gly Leu Thr Tyr Gly Ser Pro Ser Glu Gly Phe Thr Trp Ser
            725                 730                 735

Asp Gly Ser Pro Val Ser Tyr Glu Asn Trp Ala Tyr Gly Glu Pro Asn
            740                 745                 750

Asn Tyr Gln Asn Val Glu Tyr Cys Gly Glu Leu Lys Gly Asp Pro Gly
        755                 760                 765

Met Ser Trp Asn Asp Ile Asn Cys Glu His Leu Asn Asn Trp Ile Cys
770                 775                 780

Gln Ile Gln Lys Gly Lys Thr Leu Leu Pro Glu Pro Thr Pro Ala Pro
785                 790                 795                 800

Gln Asp Asn Pro Pro Val Thr Ala Asp Gly Trp Val Ile Tyr Lys Asp
            805                 810                 815

Tyr Gln Tyr Tyr Phe Ser Lys Glu Lys Glu Thr Met Asp Asn Ala Arg
        820                 825                 830

Ala Phe Cys Lys Lys Asn Phe Gly Asp Leu Ala Thr Ile Lys Ser Glu
        835                 840                 845
```

-continued

Ser Glu Lys Lys Phe Leu Trp Lys Tyr Ile Asn Lys Asn Gly Gly Gln
850             855                 860

Ser Pro Tyr Phe Ile Gly Leu Leu Ile Ser Leu Asp Lys Lys Phe Ile
865             870                 875                 880

Trp Met Asp Gly Ser Lys Val Asp Phe Val Ala Trp Ala Thr Gly Glu
            885                 890                 895

Pro Asn Phe Ala Asn Asp Asp Glu Asn Cys Val Thr Met Tyr Thr Asn
            900                 905                 910

Ser Gly Phe Trp Asn Asp Ile Asn Cys Gly Tyr Pro Asn Asn Phe Ile
            915                 920                 925

Cys Gln Arg His Asn Ser Ser Ile Asn Ala Thr Ala Met Pro Thr Thr
            930                 935                 940

Pro Pro Thr Pro Gly Gly Cys Lys Glu Gly Trp His Leu Tyr Asn Asn
945                 950                 955                 960

Lys Cys Phe Lys Ile Phe Gly Phe Ala Glu Glu Lys Lys Thr Trp
                965                 970                 975

Lys Glu Ala Arg Lys Ala Cys Ile Gly Leu Lys Gly Asn Leu Val Ser
            980                 985                 990

Ile Glu Asn Ala Lys Glu Gln Ala Phe Val Thr Tyr His Met Arg Asp
            995                 1000                1005

Ser Thr Phe Asn Ala Trp Thr Gly Leu Asn Asp Val Asn Ser Glu
    1010            1015                1020

His Thr Phe Leu Trp Thr Asp Gly Arg Gly Val His Tyr Thr Asn
    1025            1030                1035

Trp Gly Lys Gly Tyr Pro Gly Gly Arg Arg Ser Ser Leu Ser Tyr
    1040            1045                1050

Glu Asp Val Asp Cys Val Val Ile Gly Gly Asn Ser Arg Glu
    1055            1060                1065

Ala Gly Thr Trp Met Asp Ser Thr Cys Asp Ser Lys Gln Gly Tyr
    1070            1075                1080

Ile Cys Gln Thr Gln Thr Asp Pro Ser Val Pro Ile Ser Pro Thr
    1085            1090                1095

Thr Ala Pro Lys Asp Gly Phe Val Lys Tyr Gly Lys Ser Ser Tyr
    1100            1105                1110

Ala Leu Met Lys Leu Lys Ser Pro Trp His Glu Ala Glu Lys Tyr
    1115            1120                1125

Cys Lys Asp Arg Thr Ser Leu Leu Ala Ser Ile Leu Asp Pro Tyr
    1130            1135                1140

Ser Asn Ala Phe Ala Trp Met Lys Met His Pro Phe Asn Val Pro
    1145            1150                1155

Ile Trp Ile Ala Leu Asn Ser Asn Leu Thr Asn Asn Glu Tyr Thr
    1160            1165                1170

Trp Thr Asp Lys Trp Arg Val Arg Tyr Thr Asn Trp Gly Thr Asp
    1175            1180                1185

Glu Pro Lys Leu Lys Ser Ala Cys Val Tyr Met Asp Val Asp Gly
    1190            1195                1200

Tyr Trp Lys Thr Ser Tyr Cys Asn Glu Ser Phe Tyr Phe Leu Cys
    1205            1210                1215

Lys Lys Ser Asp Glu Ile Pro Ala Thr Glu Pro Pro Gln Leu Pro
    1220            1225                1230

Gly Lys Cys Pro Glu Ser Glu Gln Thr Ala Trp Ile Pro Phe His
    1235            1240                1245

Gly His Cys Tyr Tyr Ile Glu Ser Ser Phe Thr Arg Ser Trp Gly

```
              1250                1255                1260
Gln Ala Ser Leu Glu Cys Leu Arg Met Gly Ala Ser Leu Val Ser
         1265                1270                1275

Ile Glu Thr Ala Ala Glu Ser Ser Phe Leu Ser Tyr Arg Val Glu
     1280                1285                1290

Pro Leu Lys Ser Lys Thr Asn Phe Trp Ile Gly Met Phe Arg Asn
     1295                1300                1305

Val Glu Gly Lys Trp Leu Trp Leu Asn Asp Asn Pro Val Ser Phe
     1310                1315                1320

Val Asn Trp Lys Thr Gly Asp Pro Ser Gly Glu Arg Asn Asp Cys
     1325                1330                1335

Val Val Leu Ser Ser Ser Gly Leu Trp Asn Asn Ile His Cys
     1340                1345                1350

Thr Ser Tyr Lys Gly Phe Ile Cys Lys Met Pro Lys Ile Ile Asp
     1355                1360                1365

Pro Val Thr Thr His Ser Ser Ile Thr Thr Lys Ala Asp Gln Arg
     1370                1375                1380

Lys Met Asp Pro Gln Pro Lys Gly Ser Ser Lys Ala Ala Gly Val
     1385                1390                1395

Val Ile Val Val Leu Leu Ile Val Ile Gly Ala Gly Val Ala Ala
     1400                1405                1410

Tyr Phe Phe Tyr Lys Lys Arg Arg Val Leu His Ile Pro Gln Glu
     1415                1420                1425

Ala Thr Phe Glu Asn Thr Leu Tyr Phe Asn Ser Asn Pro Ser Pro
     1430                1435                1440

Gly Thr Ser Asp Thr Lys Asp Leu Val Gly Asn Ile Glu Gln Asn
     1445                1450                1455

Glu His Ala Val Ile
     1460

<210> SEQ ID NO 148
<211> LENGTH: 1455
<212> TYPE: PRT
<213> ORGANISM: Oryctolagus cuniculus

<400> SEQUENCE: 148

Met Lys Pro Ser Leu Leu Leu Ala Phe Val Ser Val Ile Pro Ala Ala
1               5                   10                  15

Val Gln Leu Leu Asp Thr Arg Gln Phe Leu Ile Tyr Asn Glu Asp His
                20                  25                  30

Lys Arg Cys Val Glu Ala Ile Ser Ser Ala Val Gln Thr Ala Val
            35                  40                  45

Cys Asn Pro Asp Ala Glu Ser Gln Arg Phe Arg Trp Val Ser Glu Phe
        50                  55                  60

His Val Met Ser Val Ala Phe Lys Leu Cys Leu Gly Val Pro Ser Lys
65                  70                  75                  80

Thr Asp Trp Val Ser Val Thr Leu Tyr Asn Cys Asp Ser Lys Ser Glu
                85                  90                  95

Phe Gln Lys Trp Glu Cys Lys Asn Asp Thr Leu Phe Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
    130                 135                 140
```

```
Thr Asp Asp Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Gln Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Ala Asp Lys Leu Phe Gly Phe
            195                 200                 205

Cys Pro Val Lys Phe Glu Gly Ser Glu Ser Leu Trp Asn Lys Asp Pro
        210                 215                 220

Leu Thr Ser Ile Ser Tyr Gln Ile Asn Ser Lys Ser Ala Leu Thr Trp
225                 230                 235                 240

His Gln Ala Arg Lys Ser Cys Gln Gln Asn Ala Glu Leu Leu Ser
                245                 250                 255

Ile Thr Glu Ile His Glu Gln Thr Tyr Leu Thr Gly Leu Thr Ser Ser
                260                 265                 270

Leu Thr Ser Gly Leu Trp Ile Gly Leu Asn Ser Leu Ser Phe Asn Ser
            275                 280                 285

Gly Trp Gln Trp Ser Gly Gly Ser Pro Phe Arg Tyr Leu Asn Trp Leu
        290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Ser Leu Asn Ser Phe Val Ile
            340                 345                 350

Pro Ser Glu Ser Asp Val Pro Thr Asn Cys Pro Ser Gln Trp Trp Pro
        355                 360                 365

Tyr Ala Gly His Cys Tyr Arg Ile His Arg Glu Glu Lys Lys Ile Gln
        370                 375                 380

Lys Asp Ala Leu Ile Ala Cys Arg Lys Glu Gly Gly Asp Leu Ala Ser
385                 390                 395                 400

Ile His Ser Ile Glu Glu Phe Asp Phe Ile Ile Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
        435                 440                 445

Phe Arg Gly Glu Pro Ser His Glu Asn Asn Arg Gln Glu Asp Cys Val
    450                 455                 460

Val Met Lys Gly Lys Asp Gly Tyr Trp Ala Asp Arg Ala Cys Glu Arg
465                 470                 475                 480

Pro Leu Asn Tyr Ile Cys Lys Met Thr Ser Arg Thr Gln Ala Thr Gly
                485                 490                 495

Ile Val Glu Val Glu Thr Gly Cys Arg Lys Gly Trp Lys Arg His Gly
            500                 505                 510

Phe Tyr Cys Tyr Leu Ile Gly His Thr Leu Ser Thr Phe Thr Glu Ala
        515                 520                 525

Asn Gln Thr Cys Glu Ser Glu Lys Ala Tyr Leu Thr Thr Val Glu Asp
        530                 535                 540

Arg Tyr Glu Gln Ala Phe Leu Thr Ser Leu Ile Gly Leu Arg Pro Glu
545                 550                 555                 560

Lys Tyr Phe Trp Thr Gly Leu Ser Asp Ile Gln Asn Lys Gly Thr Phe
```

-continued

```
                565                 570                 575
Gln Trp Thr Ile Glu Glu Val Gln Phe Thr His Trp Asn Ser Asp
                580                 585                 590
Met Pro Gly Arg Lys Ala Gly Cys Val Ala Met Arg Thr Gly Ile Ala
                595                 600                 605
Gly Gly Leu Trp Asp Ile Leu Lys Cys Asp Glu Lys Ala Lys Phe Val
                610                 615                 620
Cys Lys His Trp Ala Glu Gly Val Thr Arg Pro Glu Pro Thr Thr
625                 630                 635                 640
Thr Pro Glu Pro Arg Cys Pro Glu Asp Trp Gly Thr Ser Ser Lys Thr
                645                 650                 655
Ser Leu Cys Phe Lys Leu Phe Ala Lys Gly Lys His Glu Lys Lys Thr
                660                 665                 670
Trp Phe Glu Ser Arg Asp Phe Cys Arg Ala Val Gly Gly Glu Leu Ala
                675                 680                 685
Ser Ile Asn Asn Lys Glu Glu Gln Gln Ile Ile Trp Arg Leu Ile Thr
                690                 695                 700
Ala Gly Gly Ser Tyr His Glu Leu Phe Trp Leu Gly Leu Thr Tyr Gly
705                 710                 715                 720
Ser Pro Ser Glu Gly Phe Thr Trp Ser Asp Gly Ser Pro Val Ser Tyr
                725                 730                 735
Glu Asn Trp Ala Tyr Gly Glu Pro Asn Asn Tyr Gln Asn Val Glu Phe
                740                 745                 750
Cys Gly Glu Leu Lys Ala Asp Pro Gly Met Ser Trp Asn Asp Ile Asn
                755                 760                 765
Cys Glu His Leu Asn Asn Trp Ile Cys Gln Ile Gln Lys Gly Gln Thr
                770                 775                 780
Leu Lys Pro Glu Pro Thr Pro Ala Pro Gln Asp Asn Pro Pro Val Thr
785                 790                 795                 800
Glu Asp Gly Trp Val Ile Tyr Lys Asp Tyr Gln Tyr Tyr Phe Ser Lys
                805                 810                 815
Glu Lys Glu Thr Met Asp Asn Ala Arg Ala Phe Cys Lys Arg Asn Phe
                820                 825                 830
Gly Asp Leu Val Ser Ile Lys Ser Glu Ser Glu Lys Lys Phe Leu Trp
                835                 840                 845
Lys Tyr Val Asn Arg Asn Asp Ala Gln Thr Ala Tyr Phe Ile Gly Leu
                850                 855                 860
Leu Val Ser Leu Asp Lys Lys Phe Ala Trp Met Asp Gly Ser Lys Val
865                 870                 875                 880
Asp Tyr Val Ser Trp Ala Thr Gly Glu Pro Asn Phe Ala Asn Glu Asp
                885                 890                 895
Glu Asn Cys Val Thr Met Tyr Ala Asn Ser Gly Phe Trp Asn Asp Ile
                900                 905                 910
Asn Cys Gly Tyr Pro Asn Ala Phe Ile Cys Gln Arg His Asn Ser Ser
                915                 920                 925
Ile Asn Ala Thr Val Met Pro Thr Val Pro Gly Pro Arg Gly Cys
930                 935                 940
Lys Glu Gly Trp Asn Phe Tyr Asn Asn Lys Cys Phe Lys Ile Phe Gly
945                 950                 955                 960
Phe Val Glu Glu Glu Lys Lys Asn Trp Gln Asp Ala Arg Lys Ala Cys
                965                 970                 975
Ile Gly Phe Gly Gly Asn Leu Val Ser Ile His Asn Glu Lys Glu Gln
                980                 985                 990
```

-continued

```
Ala Phe Leu Ile Tyr His Met Lys Asp Ser Thr Phe Asn Ala Trp Thr
        995                 1000                1005
Gly Leu Asn Asp Val Asn Ser Glu His Thr Phe Leu Trp Thr Asp
    1010                1015                1020
Gly Arg Gly Val His Tyr Thr Asn Trp Gly Lys Gly Phe Pro Gly
    1025                1030                1035
Gly Arg Arg Ser Ser Leu Ser Tyr Glu Asp Ala Asp Cys Val Val
    1040                1045                1050
Ile Ile Gly Gly Lys Ser Arg Asp Ala Gly Lys Trp Met Asp Asp
    1055                1060                1065
Thr Cys Asp Ser Lys Gln Gly Tyr Ile Cys Gln Thr Pro Ser Asp
    1070                1075                1080
Pro Ser Leu Pro Ser Ser Arg Thr Thr Val Pro Thr Asp Gly Phe
    1085                1090                1095
Ile Arg Tyr Gly Lys Ser Ser Tyr Ser Leu Met Lys Leu Lys Leu
    1100                1105                1110
Gln Trp His Glu Ala Asp Lys Tyr Cys Lys Asp Asp Thr Ser Leu
    1115                1120                1125
Ile Ala Ser Ile Leu Asp Pro Tyr Ser Asn Ala Phe Val Trp Met
    1130                1135                1140
Gln Met Gln Thr Phe Asn Val Pro Val Trp Ile Ala Leu Asn Ser
    1145                1150                1155
Asn Leu Thr Asn Asn Glu Tyr Val Trp Thr Asp Arg Trp Arg Val
    1160                1165                1170
Arg Tyr Thr Asn Trp Ala Pro Asp Glu Pro Lys Leu Lys Ser Ala
    1175                1180                1185
Cys Val Tyr Leu Asp Leu Asp Gly Tyr Trp Lys Thr Ala Tyr Cys
    1190                1195                1200
Asn Glu Ser Phe Tyr Phe Leu Cys Lys Arg Ser Asp Glu Ile Pro
    1205                1210                1215
Ala Thr Glu Pro Pro Gln Leu Pro Gly Arg Cys Pro Glu Ser Glu
    1220                1225                1230
His Thr Ala Trp Ile Pro Phe His Gly His Cys Tyr Tyr Ile Glu
    1235                1240                1245
Ser Ser Tyr Thr Arg Asn Trp Gly Gln Ala Ser Leu Glu Cys Leu
    1250                1255                1260
Arg Met Gly Ser Ser Leu Val Ser Ile Glu Ser Ala Ser Glu Ser
    1265                1270                1275
Ser Phe Leu Ser Tyr Arg Val Glu Pro Leu Lys Ser Lys Thr Asn
    1280                1285                1290
Phe Trp Ile Gly Met Phe Arg Asn Val Glu Gly Met Trp Leu Trp
    1295                1300                1305
Val Asn Asn Asn Pro Val Ser Phe Val Asn Trp Asn Thr Gly Asp
    1310                1315                1320
Pro Ser Gly Glu Arg Asn Asp Cys Val Leu Leu Asp Ala Ser Ser
    1325                1330                1335
Gly Leu Trp Asn Asn Ile His Cys Ser Ser Tyr Lys Gly Tyr Ile
    1340                1345                1350
Cys Lys Arg Pro Lys Ile Val Asp Ala Glu Pro Thr Gln Thr Glu
    1355                1360                1365
Val Thr Thr Lys Ala Asp Ser Arg Lys Asp Ala Pro Ser Lys Lys
    1370                1375                1380
```

```
Ser Ser Ser Met Ala Gly Val Val Ile Ile Val Thr Leu Leu Ile
    1385                1390                1395

Leu Thr Gly Ala Gly Phe Ala Ala Tyr Phe Phe Tyr Lys Lys Arg
    1400                1405                1410

Arg Val His Ile Pro Gln Glu Gly Thr Phe Glu Asn Thr Leu Tyr
    1415                1420                1425

Phe Asn Ser Arg Ser Ser Pro Gly Thr Ser Asp Thr Lys Asp Leu
    1430                1435                1440

Met Gly Asn Ile Glu Gln Asn Glu His Ala Val Ile
    1445                1450                1455

<210> SEQ ID NO 149
<211> LENGTH: 10
<212> TYPE: PRT
<213> ORGANISM: Artificial Sequence
<220> FEATURE:
<223> OTHER INFORMATION: Linker sequence

<400> SEQUENCE: 149

Gly Ser Gly Ser Gly Ser Gly Ser Gly Ser
1               5                   10

<210> SEQ ID NO 150
<211> LENGTH: 20
<212> TYPE: PRT
<213> ORGANISM: Artificial Sequence
<220> FEATURE:
<223> OTHER INFORMATION: Linker sequence

<400> SEQUENCE: 150

Gly Ser Gly Ser Gly Ser Gly Ser Gly Ser Gly Ser Gly Ser Gly Ser
1               5                   10                  15

Gly Ser Gly Ser
            20

<210> SEQ ID NO 151
<211> LENGTH: 15
<212> TYPE: PRT
<213> ORGANISM: Artificial Sequence
<220> FEATURE:
<223> OTHER INFORMATION: Linker sequence

<400> SEQUENCE: 151

Gly Gly Gly Gly Ser Gly Gly Gly Ser Gly Gly Gly Gly Ser
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: Linker sequence

<400> SEQUENCE: 152

Ala His His Ser Glu Asp Pro Ser Ser Lys Ala Pro Lys Ala Pro Met
1               5                   10                  15

Ala

<210> SEQ ID NO 153
<211> LENGTH: 16
<212> TYPE: PRT
<213> ORGANISM: Artificial Sequence
<220> FEATURE:
<223> OTHER INFORMATION: Linker sequence
```

<400> SEQUENCE: 153

Ser Pro Ser Thr Pro Pro Thr Pro Ser Pro Ser Thr Pro Pro Ala Ser
1               5                   10                  15

<210> SEQ ID NO 154
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 154

Ile Glu Gly Arg
1

<210> SEQ ID NO 155
<211> LENGTH: 4
<212> TYPE: PRT
<213> ORGANISM: Artificial Sequence
<220> FEATURE:
<223> OTHER INFORMATION: thrombin cleavage site

<400> SEQUENCE: 155

Leu Val Pro Arg
1

<210> SEQ ID NO 156
<211> LENGTH: 5
<212> TYPE: PRT
<213> ORGANISM: Artificial Sequence
<220> FEATURE:
<223> OTHER INFORMATION: enterokinase cleaving site

<400> SEQUENCE: 156

Asp Asp Asp Asp Lys
1               5

<210> SEQ ID NO 157
<211> LENGTH: 8
<212> TYPE: PRT
<213> ORGANISM: Artificial Sequence
<220> FEATURE:
<223> OTHER INFORMATION: PreScission cleavage site

<400> SEQUENCE: 157

Leu Glu Val Leu Phe Gln Gly Pro
1               5

<210> SEQ ID NO 158
<211> LENGTH: 41
<212> TYPE: DNA
<213> ORGANISM: Artificial Sequence
<220> FEATURE:
<223> OTHER INFORMATION: Primer

<400> SEQUENCE: 158
ccggccatgg cccaggtgca gcttcaggag tctggaggag g          41

<210> SEQ ID NO 159
<211> LENGTH: 88
<212> TYPE: DNA
<213> ORGANISM: Artificial Sequence
<220> FEATURE:
<223> OTHER INFORMATION: Primer

<400> SEQUENCE: 159
tgattcctgc agctgcacct gactaccgcc gcctccagat ccacctccgc cactaccgcc        60
tccgcctgag agacggtga cctgggtc                                            88

<210> SEQ ID NO 160
<211> LENGTH: 94
<212> TYPE: DNA
<213> ORGANISM: Artificial Sequence
<220> FEATURE:
<223> OTHER INFORMATION: Primer

<400> SEQUENCE: 160
tgattcctgc agctgcacct gtgccattgg agctttggga gctttggagc tggggtcttc        60
gctgtggtgc gctgaggaga cggtgacctg ggtc                                    94

<210> SEQ ID NO 161
<211> LENGTH: 91
<212> TYPE: DNA
<213> ORGANISM: Artificial Sequence
<220> FEATURE:
<223> OTHER INFORMATION: Primer

<400> SEQUENCE: 161
tgattcctgc agctgcacct gacttgccgg tggtgtggat ggtgatggtg tgggaggtgt        60
agatgggctt gaggagacgg tgacctgggt c                                       91

<210> SEQ ID NO 162
<211> LENGTH: 15
<212> TYPE: PRT
<213> ORGANISM: Artificial Sequence
<220> FEATURE:
<223> OTHER INFORMATION: Linker

<400> SEQUENCE: 162

Gly Gly Gly Gly Ser Gly Gly Gly Gly Ser Gly Gly Gly Gly Ser
1               5                   10                  15

<210> SEQ ID NO 163
<211> LENGTH: 17
<212> TYPE: PRT
<213> ORGANISM: Artificial Sequence
<220> FEATURE:
<223> OTHER INFORMATION: Linker

<400> SEQUENCE: 163

Ala His His Ser Glu Asp Pro Ser Ser Lys Ala Pro Lys Ala Pro Met
1               5                   10                  15

Ala

<210> SEQ ID NO 164
<211> LENGTH: 16
<212> TYPE: PRT
<213> ORGANISM: Artificial Sequence
<220> FEATURE:
<223> OTHER INFORMATION: Linker

<400> SEQUENCE: 164

Ser Pro Ser Thr Pro Pro Thr Pro Ser Pro Ser Thr Pro Pro Ala Ser
1               5                   10                  15

<210> SEQ ID NO 165
<211> LENGTH: 22
<212> TYPE: DNA
<213> ORGANISM: Artificial Sequence

```
<220> FEATURE:
<223> OTHER INFORMATION: Primer

<400> SEQUENCE: 165
gtcctggctc tcttctacaa gg                                              22

<210> SEQ ID NO 166
<211> LENGTH: 23
<212> TYPE: DNA
<213> ORGANISM: Artificial Sequence
<220> FEATURE:
<223> OTHER INFORMATION: Primer

<400> SEQUENCE: 166
ggtacgtgct gttgaactgt tcc                                             23

<210> SEQ ID NO 167
<211> LENGTH: 29
<212> TYPE: DNA
<213> ORGANISM: Artificial Sequence
<220> FEATURE:
<223> OTHER INFORMATION: Primer

<400> SEQUENCE: 167
gatgtgcagc tgcaggagtc tggrggagg                                       29

<210> SEQ ID NO 168
<211> LENGTH: 34
<212> TYPE: DNA
<213> ORGANISM: Artificial Sequence
<220> FEATURE:
<223> OTHER INFORMATION: Primer

<400> SEQUENCE: 168
ctagtgcggc cgctgaggag acggtgacct gggt                                 34

<210> SEQ ID NO 169
<211> LENGTH: 10
<212> TYPE: PRT
<213> ORGANISM: Artificial Sequence
<220> FEATURE:
<223> OTHER INFORMATION: HA tag

<400> SEQUENCE: 169

Tyr Pro Tyr Asp Val Pro Asp Tyr Gly Ser
1               5                   10

<210> SEQ ID NO 170
<211> LENGTH: 19
<212> TYPE: PRT
<213> ORGANISM: Artificial Sequence
<220> FEATURE:
<223> OTHER INFORMATION: HA and 6xHis tag

<400> SEQUENCE: 170

Ala Ala Ala Tyr Pro Tyr Asp Val Pro Asp Tyr Gly Ser His His His
1               5                   10                  15

His His His
```